United States Patent
Tidwell et al.

(10) Patent No.: US 7,417,158 B2
(45) Date of Patent: Aug. 26, 2008

(54) CATIONIC SUBSTITUTED BENZOFURANS AS ANTIMICROBIAL AGENTS

(75) Inventors: Richard R. Tidwell, Pittsboro, NC (US); Karl Werbovetz, Worthington, OH (US); Scott Gary Franzblau, Chicago, IL (US); Svetlana Bakunova, Chapel Hill, NC (US); Stanislav Bakunov, Chapel HIll, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 421 days.

(21) Appl. No.: 11/005,524

(22) Filed: Dec. 6, 2004

(65) Prior Publication Data

US 2005/0197378 A1  Sep. 8, 2005

Related U.S. Application Data

(60) Provisional application No. 60/527,492, filed on Dec. 5, 2003.

(51) Int. Cl.
*C07D 307/00* (2006.01)
*A61K 31/415* (2006.01)
*A61K 31/34* (2006.01)

(52) U.S. Cl. .................. 549/471; 514/397; 514/469
(58) Field of Classification Search ............ 549/471; 514/397, 469
See application file for complete search history.

(56) References Cited

U.S. PATENT DOCUMENTS 3,652,591 A  3/1972  Dann et al.
3,689,506 A  9/1972  Dann

FOREIGN PATENT DOCUMENTS

WO  WO 96/40138  12/1996
WO  WO 2005/025565 A1  3/2005

OTHER PUBLICATIONS

International Search Report corresponding to PCT app. No. PCT/US04/40557 dated Jul. 14, 2005.
Written Opinion corresponding to PCT app. No. PCT/US04/40557 dated Jul. 14, 2005.
Verner et al. "Development of serine Protease Inhibitors displaying a Multicentered Short (<2.3 Å) Hydrogen Bond Binding Mode: Inhibitors of Urokinase-Type Plasminogen Activator and Factor Xa", *J. Med. Chem.*, 44: 2753-2771, 2001.
International Preliminary Report on Patentability corresponding to PCT application No. PCT/US2004/040557 dated Jun. 15, 2006.
Written Opinion of the International Searching Authority corresponding to PCT application No. PCT/US04/40557 dated Jul. 14, 2005.

*Primary Examiner*—D. Margaret Seaman
*Assistant Examiner*—Nizal S Chandrakumar
(74) *Attorney, Agent, or Firm*—Jenkins, Wilson, Taylor & Hunt, P.A.

(57) ABSTRACT

A method of treating a *Mycobacterium tuberculosis* infection in a subject in need thereof by administering to the subject an effective amount of a cationic substituted benzofuran compound. Methods of treating microbial infections, including infections from protozoan pathogens, such as *Leishmania donovani*, *Trypanosoma brucei rhodesiense*, a *Trypanosoma cruzi*, and *Plasmodium falciparum*, and fungal pathogens, such as *Candida albicans*, *Aspergillus fumigatus*, and *Cryptococcus neoformans*, in a subject in need thereof by administering to the subject an effective amount of a cationic substituted benzofuran compound. Methods of synthesizing novel cationic substituted benzofuran compounds and the novel compounds themselves.

21 Claims, No Drawings

CATIONIC SUBSTITUTED BENZOFURANS AS ANTIMICROBIAL AGENTS

CROSS REFERENCE TO RELATED APPLICATIONS

This application claims the benefit of and priority to U.S. Provisional patent application Ser. No. 60/527,492, filed Dec. 5, 2003, the disclosure of which is incorporated herein by reference in its entirety.

GOVERNMENT INTEREST

This invention was made with U.S. Government support under grant number AI46365 from the National Institutes of Health. Thus, the U.S. Government has certain rights in the invention.

TECHNICAL FIELD

The presently disclosed subject matter relates to methods of combating microbial infections with cationic substituted compounds and processes of synthesizing cationic substituted compounds. More particularly, the presently disclosed subject matter relates to methods of combating microbial infections with cationic substituted benzofurans, processes of synthesizing cationic substituted benzofurans, and to the novel compounds themselves.

| ABBREVIATIONS | |
|---|---|
| $\delta$ = | chemical shift |
| Ac = | acetyl |
| AcO = | acetoxyl |
| AcOH = | acetic acid |
| $Ac_2O$ = | acetic anhydride |
| Am = | amidine |
| AmOH = | amidoxime |
| Bu = | butyl |
| °C. = | degrees Celsius |
| calcd = | calculated |
| cm = | centimeters |
| dec = | decomposition point |
| DIBAL = | diisobutylaluminium hydride |
| DMF = | dimethylformamide |
| DMSO = | dimethylsulfoxide |
| $D_2O$ = | deuterium oxide |
| EtOAc = | ethyl acetate |
| EtOH = | ethanol |
| FAB = | fast atom bombardment |
| g = | grams |
| h = | hours |
| HCl = | hydrogen chloride |
| HPLC = | high-pressure liquid chromatography |
| Hz = | hertz |
| kg = | kilograms |
| KO-t-Bu = | potassium tert-butoxide |
| L. d. = | *Leishmania donovani* |
| M = | molar |
| Me = | methyl |
| MeO = | methoxyl |
| MHz = | megahertz |
| mL = | milliliters |
| mm = | millimeters |
| mM = | millimolar |
| m.p. = | melting point |
| MS = | mass spectroscopy |
| $Na_2CO_3$ = | sodium carbonate |
| $Na_2SO_4$ = | sodium sulfate |
| NBS = | N-bromosuccinimide |
| $NH_2OH \cdot HCl$ = | hydroxylamine hydrochloride |
| NMR = | nuclear magnetic resonance |
| p = | para |
| Pd—C = | 10% palladium on carbon |

| ABBREVIATIONS | |
|---|---|
| P. f. = | *Plasmodium falciparum* |
| psi = | pounds per square inch |
| spp. = | species |
| T. br. = | *Trypanosoma brucei rhodesiense* |
| T. cruzi = | *Trypanosoma cruzi* |
| THF = | tetrahydrofuran |
| TLC = | thin-layer chromatography |
| TMS = | trimethylsilyl |
| UV = | ultraviolet |

BACKGROUND

The incidence of microbial infections (e.g., mycobacterial, fungal, and protozoal infections) in the immunocompromised population has significantly increased over the past several years. In particular, Candida species, especially *Candida albicans*, are often significant pathogens in patients infected with human immunodeficiency virus (HIV). Another pathogen, *Pneumocystis carinii*, causes a form of pneumonia (PCP) that is believed to be one of the leading causes of death in patients suffering from AIDS. Further, Human African trypanosomiasis (HAT) has reemerged as a threat to over 60 million people. Current estimates are that between 350,000 and 450,000 people are infected. Other severe and life-threatening microbial infections are caused by *Mycobacterium tuberculosis*, *Aspergillus* spp., *Crypotosporidium parvum*, *Giardia lamblia*, *Plasmodium* spp., *Toxoplasma gondii*, *Fusarium solani*, and *Cryptococcus neoformans*.

The antimicrobial properties of dicationic molecules have been studied since the 1930's. Compounds of this type have typically utilized amidine groups as the cationic moieties, and their activities against a number of pathogens including *Cryptosporidium parvum*, *Giardia lamblia*, *Leishmania* spp., *Plasmodium* spp., *Pneumocystis carinii*, *Toxoplasma gondii*, *Trypanosoma* spp., *Candida albicans*, *Aspergillus* spp. and *Cryptococcus neoformans* have been reported. See, e.g., King, H. et al., *Ann. Trop. Med. Parasitol.* 1938, 32, 177-192; Blagburn, B. L. et al., *Antimicrob. Agents Chemother.* 1991, 35, 1520-1523; Bell, C. A. et al., *Antimicrob. Agents Chemother.* 1991, 35, 1099-1107; Bell, C. A. et al., *Antimicrob. Agents Chemother.* 1990, 34, 1381-1386; Kirk, R. et al., *Ann. Trop. Med. Parasitol.* 1940, 34, 181-197; Fulton, J. D. *Ann. Trop. Med. Parasitol.* 1940, 34, 53-66; Ivady, V. G. et al., *Monatschr. Kinderheilkd.* 1958, 106, 10-14; Boykin, D. W. et al., *J. Med. Chem.* 1995, 38, 912-916; Boykin, D. W. et al., *J. Med. Chem.* 1998, 41, 124-129; Francesconi, I. et al., *J. Med. Chem.* 1999, 42, 2260-2265; Lindsay, D. S. et al., *Antimicrob. Agents Chemother.* 1991, 35, 1914-1916; Lourie, E. M. et al., *Ann. Trop. Med. Parasitol.* 1939, 33, 289-304; Lourie, E. M. et al., *Ann. Trop. Med. Parasitol.* 1939, 33, 305-312; Das, B. P. et al., *J. Med. Chem.* 1976, 20, 531-536; Del Poeta, M. et al., *J. Antimicrob. Chemother.* 1999, 44, 223-228; Del Poeta, M. et al., *Antimicrob. Agents Chemother.* 1998, 42, 2495-2502; Del Poeta, M. et al., *Anitmicrob. Agents Chemother.* 1998, 42, 2503-2510.

Despite the broad range of activity exhibited by diamidines, only one compound of this chemical type, pentamidine, has seen significant clinical use. Pentiamidine has been used clinically against African trypanosomiasis, antimony-resistant leishmaniasis, and *P. carinii* pneumonia. See, e.g., Apted, F. I. C., *Pharmacol. Ther.* 1980, 11, 391-413; Bryceson, A. D. M. et al., *Trans. Roy. Soc. Trop. Med. Hyg.* 1985, 79, 705-714; Hughes, W. T. et al., *Antimicrob. Agents Chemother.* 1974, 5, 289-293.

Thus, there continues to be a need for improvement in the art for additional compounds having desirable anti-microbial activity, whether against the representative pathogens referenced above or against other pathogens.

SUMMARY

In some embodiments, the presently disclosed subject matter relates to a method of treating a *Mycobacterium tuberculosis* infection in a subject in need thereof, the method comprising administering to the subject an effective amount of a compound of Formula (I):

(I)

wherein:
  n is an integer from 1 to 8;
  p and q are integers from 0 to 3;
  $X_1$ and $X_2$ are each independently selected from the group consisting of O, S, and $NR_5$, wherein $R_5$ is selected from the group consisting of H, alkyl, aryl, alkoxyl, and aryloxyl;
  $R_1$ and $R_2$ are each independently selected from the group consisting of alkyl, halo, hydroxyl, alkoxyl, aryloxyl, and aralkyloxyl; and
  $R_3$ and $R_4$ are each independently selected from the group consisting of:

wherein:
  $R_6$, $R_7$, $R_8$, and $R_9$ are each independently selected from the group consisting of H, alkyl, cycloalkyl, aryl, aralkyl, hydroxyl, alkoxyl, hydroxyalkyl, hydroxycycloalkyl, alkoxycycloalkyl, aminoalkyl, acyloxyl, alkylaminoalkyl, and alkoxycarbonyl; or
  $R_6$ and $R_7$ together represent a $C_2$ to $C_{10}$ alkyl, $C_2$ to $C_{10}$ hydroxyalkyl, or $C_2$ to $C_{10}$ alkylene.

In some embodiments, the presently disclosed subject matter relates to a method of treating a *Mycobacterium tuberculosis* infection in a subject in need thereof, the method comprising administering to the subject an effective amount of a compound of Formula (II):

(II)

wherein:
  p and q are integers from 0 to 3;
  $R_1$ and $R_2$ are each independently selected from the group consisting of alkyl, halo, hydroxyl, alkoxyl, aryloxyl, and aralkyloxyl; and
  $R_3$ and $R_4$ are each independently selected from the group consisting of:

wherein:
  $R_6$, $R_7$, $R_8$, and $R_9$ are each independently selected from the group consisting of H, alkyl, cycloalkyl, aryl, aralkyl, hydroxyl, alkoxyl, hydroxyalkyl, hydroxycycloalkyl, alkoxycycloalkyl, aminoalkyl, acyloxyl, alkylaminoalkyl, and alkoxycarbonyl; or
  $R_6$ and $R_7$ together represent a $C_2$ to $C_{10}$ alkyl, $C_2$ to $C_{10}$ hydroxyalkyl, or $C_2$ to $C_{10}$ alkylene.

In some embodiments, the presently disclosed subject matter relates to a method of treating a *Mycobacterium tuberculosis* infection in a subject in need thereof, the method comprising administering to the subject an effective amount of a compounds of Formula (III):

(III)

wherein:
  n is an integer from 1 to 8;
  p and q are integers from 0 to 3;
  $R_1$ and $R_2$ are each independently selected from the group consisting of alkyl, halo, hydroxyl, alkoxyl, aryloxyl, and aralkyloxyl; and
  $R_3$ and $R_4$ are each independently selected from the group consisting of:

wherein:
  $R_6$, $R_7$, $R_8$, and $R_9$ are each independently selected from the group consisting of H, alkyl, cycloalkyl, aryl, aralkyl, hydroxyl, alkoxyl, hydroxyalkyl, hydroxycycloalkyl, alkoxycycloalkyl, aminoalkyl, acyloxyl, alkylaminoalkyl, and alkoxycarbonyl; or
  $R_6$ and $R_7$ together represent a $C_2$ to $C_{10}$ alkyl, $C_2$ to $C_{10}$ hydroxyalkyl, or $C_2$ to $C_{10}$ alkylene.

In some embodiments, the presently disclosed subject matter relates to a method of treating microbial infections, including infections from protozoan pathogens, such as *Leishmania donovani*, *Trypanosoma brucei rhodesiense*, a *Trypanosoma cruzi*, and *Plasmodium falciparum*, and fungal pathogens, such as *Candida albicans*, *Aspergillus fumigatus*, and *Cryptococcus neoformans*, in a subject in need thereof, the method comprising administering to the subject an effective amount of a compound of any of Formulae (I), (II), and (III).

In some embodiments, the presently disclosed subject matter relates to compounds of Formulae (I), (II), and (III).

In some embodiments, the presently disclosed subject matter relates to pharmaceutical formulations comprising a compound of any of Formula (I), (II), and (III) in a pharmaceutically acceptable carrier.

In some embodiments, the presently disclosed subject matter relates to a method of preparing a compound of any of Formula (I), (II), and (III).

In some embodiments, the presently disclosed subject matter relates to the use of an active compound as described above, (i.e., a compound of Formula (I), (II), or (III)), for the preparation of a medicament for treating a microbial infection.

Accordingly, in some embodiments, the presently disclosed subject matter provides methods for treating microbial infections. In some embodiments, the presently disclosed subject matter provides compounds that are useful in the treatment of microbial infections. In some embodiments, the presently disclosed subject matter provides pharmaceutical formulations for use in the treatment of microbial infections.

Certain aspects of the presently disclosed subject matter having been stated hereinabove, which are addressed in whole or in part by the presently disclosed subject matter, other aspects will become evident as the description proceeds when taken in connection with the accompanying Examples as best described herein below.

DETAILED DESCRIPTION

The presently disclosed subject matter will now be described more fully hereinafter with reference to the accompanying Examples, in which representative embodiments are shown. The presently disclosed subject matter can, however, be embodied in different forms and should not be construed as limited to the embodiments set forth herein. Rather, these embodiments are provided so that this disclosure will be thorough and complete, and will fully convey the scope of the embodiments to those skilled in the art.

Unless otherwise defined, all technical and scientific terms used herein have the same meaning as commonly understood by one of ordinary skill in the art to which this presently described subject matter belongs. All publications, patent applications, patents, and other references mentioned herein are incorporated by reference in their entirety.

Throughout the specification and claims, a given chemical formula or name shall encompass all optical and stereoisomers, as well as racemic mixtures where such isomers and mixtures exist.

I. Definitions

As used herein the term "alkyl" refers to $C_{1-20}$ inclusive, linear (i.e., "straight-chain"), branched, or cyclic, saturated or at least partially and in some cases fully unsaturated (i.e., alkenyl and alkynyl) hydrocarbon chains, including for example, methyl, ethyl, propyl, isopropyl, butyl, isobutyl, tert-butyl, pentyl, hexyl, octyl, ethenyl, propenyl, butenyl, pentenyl, hexenyl, octenyl, butadienyl, propynyl, butynyl, pentynyl, hexynyl, heptynyl, and allenyl groups. "Branched" refers to an alkyl group in which a lower alkyl group, such as methyl, ethyl or propyl, is attached to a linear alkyl chain.

"Lower alkyl" refers to an alkyl group having 1 to about 8 carbon atoms (i.e., a $C_{1-8}$ alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or 20 carbon atoms. In certain embodiments, "alkyl" refers, in particular, to $C_{1-8}$ straight-chain alkyls. In other embodiments, "alkyl" refers, in particular, to $C_{1-8}$ branched-chain alkyls.

Alkyl groups can optionally be substituted with one or more alkyl group substituents, which can be the same or different. The term "alkyl group substituent" includes but is not limited to alkyl, halo, arylamino, acyl, hydroxyl, aryloxyl, alkoxyl, alkylthio, arylthio, aralkyloxyl, aralkylthio, carboxyl, alkoxycarbonyl, oxo, and cycloalkyl. There can be optionally inserted along the alkyl chain one or more oxygen, sulfur or substituted or unsubstituted nitrogen atoms, wherein the nitrogen substituent is hydrogen, lower alkyl (also referred to herein as "alkylaminoalkyl"), or aryl.

The term "aryl" is used herein to refer to an aromatic substituent that can be a single aromatic ring, or multiple aromatic rings that are fused together, linked covalently, or linked to a common group such as a methylene or ethylene moiety. The common linking group also can be a carbonyl as in benzophenone or oxygen as in diphenylether or nitrogen as in diphenylamine. The term "aryl" specifically encompasses heterocyclic aromatic compounds. The aromatic ring(s) can comprise phenyl, naphthyl, biphenyl, diphenylether, diphenylamine and benzophenone, among others. In particular embodiments, the term "aryl" means a cyclic aromatic comprising about 5 to about 10 carbon atoms, e.g., 5, 6, 7, 8, 9, or 10 carbon atoms, and including 5- and 6-membered hydrocarbon and heterocyclic aromatic rings.

The aryl group can be optionally substituted with one or more aryl group substituents which can be the same or different, where "aryl group substituent" includes alkyl, aryl, aralkyl, hydroxyl, alkoxyl, aryloxyl, aralkyloxyl, carboxyl, acyl, halo, nitro, alkoxycarbonyl, aryloxycarbonyl, aralkoxycarbonyl, acyloxyl, acylamino, aroylamino, carbamoyl, alkylcarbamoyl, dialkylcarbamoyl, arylthio, alkylthio, alkylene, and —NR'R", where R' and R" can be each independently hydrogen, alkyl, aryl, and aralkyl.

Specific examples of aryl groups include but are not limited to cyclopentadienyl, phenyl, furan, thiophene, pyrrole, pyran, pyridine, imidazole, benzimidazole, isothiazole, isoxazole, pyrazole, pyrazine, triazine, pyrimidine, quinoline, isoquinoline, indole, carbazole, and the like.

A dashed line representing a bond in an aryl group indicates that the bond is either present or absent depending on the number of carbon atoms in the aromatic ring and, in the case of a heterocyclic aromatic ring, the identity of the heteroatom.

When a names atom of an aromatic ring or a heterocyclic aromatic ring is defined as being "absent," the named atom is replaced by a direct bond.

As used herein, the terms "substituted alkyl" and "substituted aryl"0 include alkyl and aryl groups, as defined herein, in which one or more atoms or functional groups of the aryl or alkyl group are replaced with another atom or functional group, including for example, halogen, aryl, alkyl, alkoxyl, hydroxyl nitro, amino, alkylamino, dialkylamino, sulfate, and mercapto.

As used herein, the term "acyl" refers to an organic acid group wherein the —OH of the carboxyl group has been replaced with another substituent (i.e., as represented by RCO—, wherein R is an alkyl or an aryl group as defined herein). As such, the term "acyl" specifically includes arylacyl groups. Specific examples of acyl groups include acetyl and benzoyl.

"Cyclic" and "cycloalkyl" refer to a non-aromatic mono- or multicyclic ring system of about 3 to about 10 carbon atoms, e.g., 3, 4, 5, 6, 7, 8, 9, or 10 carbon atoms. The cycloalkyl group can be optionally partially unsaturated. The cycloalkyl group can be also optionally substituted with an alkyl group substituent as defined herein, oxo, and/or alkylene. There can be optionally inserted along the cyclic alkyl chain one or more oxygen, sulfur or substituted or unsubstituted nitrogen atoms, wherein the nitrogen substituent is hydrogen, lower alkyl, or aryl, thus providing a heterocyclic group. Representative monocyclic cycloalkyl rings include cyclopentyl, cyclohexyl, and cycloheptyl. Multicyclic cycloalkyl rings include adamantyl, octahydronaphthyl, decalin, camphor, camphane, and noradamantyl.

"Alkoxyl" or "alkoxyalkyl" refer to an alkyl-O— group wherein alkyl is as previously described. The term "alkoxyl" as used herein can refer to $C_{1-20}$ inclusive, linear, branched, or cyclic, saturated or unsaturated oxo-hydrocarbon chains, including, for example, methoxyl, ethoxyl, propoxyl, isopropoxyl, butoxyl, t-butoxyl, and pentoxyl.

"Aryloxyl" refers to an aryl-O— group wherein the aryl group is as previously described. The term "aryloxyl" as used herein can refer to phenyloxyl or hexyloxyl, and alkyl, halo, or alkoxyl substituted phenyloxyl or hexyloxyl.

"Aralkyl" refers to an aryl-alkyl- group wherein aryl and alkyl are as previously described. Exemplary aralkyl groups include, but are not limited to, benzyl, phenylethy, and naphthylmethyl.

"Aralkyloxyl" refers to an aralkyl-O— group wherein the aralkyl group is as previously described. An exemplary aralkyloxyl group is benzyloxyl.

"Dialkylamino" refers to an —NRR' group wherein each of R and R' is independently an alkyl group as previously described. Exemplary alkylamino groups include, but are not limited to, ethylmethylamino, dimethylamino, and diethylamino.

"Alkoxycarbonyl" refers to an alkyl-O—CO— group. Exemplary alkoxycarbonyl groups include, but are not limited to, methoxycarbonyl, ethoxycarbonyl, butyloxycarbonyl, and t-butyloxycarbonyl.

"Alkoxycarbonyl" refers to an aryl-O—CO— group. Exemplary aryloxycrabonyl groups include, but are not limited to, phenoxy- and naphthoxy-carbonyl.

"Aralkoxycarbonyl" refers to an aralkyl-O—CO— group. An exemplary aralkoxycarbonyl group is benzyloxycarbonyl.

"Carbamoyl" refers to an $H_2N$—CO— group.

"Alkylcarbamoyl" refers to R'RN—CO— group wherein one of R and R' is hydrogen and the other of R and R' is alkyl as previously described.

"Dialkylcarbamoyl" refers to R'RN—CO— group wherein each of R and R' is independently alkyl as previously described.

"Acyloxyl" refers to an acyl-O— group wherein acyl is as previously described.

"Acylamino" refers to an acyl-NH— group wherein acyl is as previously described.

"Aroylamino" refers to an aroyl-NH— group wherein aroyl is as previously described.

"Alkylene" refers to a straight or branched bivalent aliphatic hydrocarbon group having from 1 to about 20 carbon atoms, e.g., 1, 2, 3, 4, 5, 6, 7, 8, 9, 10, 11, 12, 13, 14, 15, 16, 17, 18, 19, or 20 carbon atoms. The alkylene group can be straight, branched or cyclic. The alkylene group can be also optionally unsaturated and/or substituted with one or more "alkyl group substituents." There can be optionally inserted along the alkylene group one or more oxygen, sulfur or substituted or unsubstituted nitrogen atoms (also referred to herein as "alkylaminoalkyl"), wherein the nitrogen substituent is alkyl as previously described. Exemplary alkylene groups include methylene (—$CH_2$—); ethylene (—$CH_2$—$CH_2$—); propylene (—$(CH_2)_3$—); cyclohexylene (—$C_6H_{10}$—); —CH=CH—CH=CH—; —CH=CH—$CH_2$—; —$(CH_2)_q$—N(R)—$(CH_2)_r$—, wherein each of q and r is independently an integer from 0 to about 20, e.g., 0, 1, 2, 3, 4, 5, 6, 7, 8, 9, 10, 11, 12, 13, 14, 15, 16, 17, 18, 19, or 20, and R is hydrogen or lower alkyl; methylenedioxyl (—O—$CH_2$—O—); and ethylenedioxyl (—O—$(CH_2)_2$—O—). An alkylene group can have about 2 to about 3 carbon atoms and can further have 6-20 carbons.

The term "amino" refers to the —$NH_2$ group.

The term "carbonyl" refers to the —(C=O)— group.

The term "carboxyl" refers to the —COOH group.

The terms "halo", "halide", or "halogen" as used herein refer to fluoro, chloro, bromo, and iodo groups.

The term "hydroxyl" refers to the —OH group.

The term "hydroxyalkyl" refers to an alkyl group substituted with an —OH group.

The term "mercapto" refers to the —SH group.

The term "oxo" refers to a compound described previously herein wherein a carbon atom is replaced by an oxygen atom.

The term "nitro" refers to the —$NO_2$ group.

The term "thio" refers to a compound described previously herein wherein a carbon or oxygen atom is replaced by a sulfur atom.

The term "sulfate" refers to the —$SO_4$ group.

When the term "independently selected" is used, the substituents being referred to (i.e., R groups, such as groups $R_1$ and $R_2$, or groups X and Y), can be identical or different. For example, both $R_1$ and $R_2$ can be substituted alkyls, or $R_1$ can be hydrogen and $R_2$ can be a substituted alkyl, etc.

A named "R", "R'," "X," "Y," "Y'", "A," "A'", "B'", "L," or "Z" group will generally have the structure that is recognized in the art as corresponding to a group having that name, unless specified otherwise herein. For the purposes of illustration, certain representative "R," "X," "Y", and "A" groups as set forth above are defined below. These definitions are intended to supplement and illustrate, not preclude, the definitions that would be apparent to one of ordinary skill in the art upon review of the present disclosure.

The term "reflux" and grammatical derivations thereof refer to boiling a liquid, such as a solvent, in a container, such as a reaction flask, with which a condenser is associated, thereby facilitating continuous boiling without loss of liquid, due to the condensation of vapors on the interior wall of the condenser.

The term "aprotic solvent" refers to a solvent molecule which can neither accept nor donate a proton. Typical aprotic solvents include, but are not limited to, acetone, acetonitrile, benzene, butanone, butyronitrile, carbontetrachloride, chlorobenzene, chloroform, 1,2-dichloroethane, dichloromethane, diethyl ether, dimethylacetamide, N,N-dimethylformamide (DMF), dimethylsulfoxide (DMSO), 1,4-dioxane, ethyl acetate, ethylene glycol dimethyl ether, hexane, n-methylpyrrolidone, pyridine, tetrahydrofuran (THF), and toluene. Certain aprotic solvents are polar solvents. Examples of polar aprotic solvents include, but are not limited to, acetone, acetonitrile, butanone, N,N-dimethylformamide, and dimethylsulfoxide. Certain aprotic solvents are non-polar solvents. Examples of nonpolar, aprotic solvents include, but are not limited to, diethyl ether, aliphatic hydrocarbons, such as hexane, aromatic hydrocarbons, such as benzene and toluene, and symmetrical halogenated hydrocarbons, such as carbon tetrachloride.

The term "protic solvent" refers to a solvent molecule which contains a hydrogen atom bonded to an electronegative atom, such as an oxygen atom or a nitrogen atom. Typical protic solvents include, but are not limited to, carboxylic acids, such as acetic acid, alcohols, such as methanol and ethanol, amines, amides, and water.

The term "metal alkyl" refers to a compound of the general formula $MR_n$, wherein M is a metal atom, including, but not limited to aluminum, boron, magnesium, zinc, gallium, indium, antimony and related metals, R is an alkyl group as defined herein, and n is an integer. A representative metal alkyl is trimethylaluminum, abbreviated as Al(CH$_3$)$_3$ or AlMe$_3$.

The term "alkali metal alcoholate" refers to an alkali metal derivative of an alcohol having the general formula M$_a$OR$_n$, wherein M$_a$ is an alkali metal, such as lithium, sodium, or potassium, O is oxygen, R is an alkyl group as defined herein, and n is an integer. Representative alkali metal alcoholates include, but are not limited to, sodium methanolate, abbreviated as NaOCH$_3$ or NaOMe, and potassium butoxide, abbreviated as KOC(CH$_3$)$_3$.

The term "acid anhydride" refers to an anhydride of an organic acid and includes, but is not limited to, acetic anhydride ((CH$_3$C=O)$_2$O or Ac$_2$O) and benzonic anhydride ((C$_6$H$_5$C=O)$_2$O).

II. Methods of Treating Microbial Infections

Subjects with microbial infections can be treated by methods described herein. These infections can be caused by a variety of microbes, including fungi, algae, protozoa, bacteria, and viruses. Exemplary microbial infections that can be treated by the method of the presently disclosed subject matter include, but are not limited to, infections caused by *Mycobacterium tuberculosis*, *Trypanosoma* species (e.g., *Trypanosoma brucei rhodesiense* and *Trypanosoma cruzi*), *Pneumocytsis carnii*, *Giardia lamblia*, *Cryptosporidium parvum*, *Cryptococcus neoformans*, *Candida albicans*, *Candida tropicalis*, *Salmonella typhimurium*, *Plasmodium falciparum*, *Leishmania donovani*, and *Leishmania mexicana amazonensis*. The methods of the presently disclosed subject matter are useful for treating these conditions in that they inhibit the onset, growth, or spread of the condition, cause regression of the condition, cure the condition, or otherwise improve the general well-being of a subject afflicted with, or at risk of contracting the condition.

Methods of treating microbial infections comprise administering to a subject in need of treatment an active compound as described herein. These active compounds, as set forth above, include compounds of Formulae (I), (II), and (III), their corresponding prodrugs, and pharmaceutically acceptable salts of the compounds and prodrugs.

With regard to the presently described method embodiments, compounds of Formula (I) are defined as having a structure as follow:

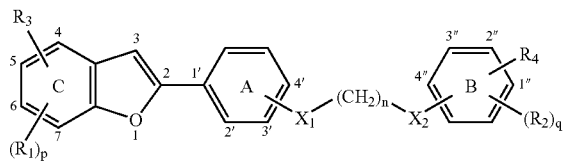

(I)

wherein:
n is an integer from 1 to 8;
p and q are integers from 0 to 3;
X$_1$ and X$_2$ are each independently selected from the group consisting of O, S, and NR$_5$, wherein R$_5$ is selected from the group consisting of H, alkyl, aryl, alkoxyl, and aryloxyl;
R$_1$ and R$_2$ are each independently selected from the group consisting of alkyl, halo, hydroxyl, alkoxyl, aryloxyl, and aralkyloxyl; and
R$_3$ and R$_4$ are each independently selected from the group consisting of:

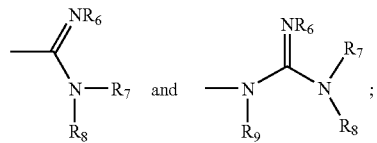

wherein:
R$_6$, R$_7$, R$_8$, and R$_9$ are each independently selected from the group consisting of H, alkyl, cycloalkyl, aryl, aralkyl, hydroxyl, alkoxyl, hydroxyalkyl, hydroxycycloalkyl, alkoxycycloalkyl, aminoalkyl, acyloxyl, alkylaminoalkyl, and alkoxycarbonyl; or
R$_6$ and R$_7$ together represent a C$_2$ to C$_{10}$ alkyl, C$_2$ to C$_{10}$ hydroxyalkyl, or C$_2$ to C$_{10}$ alkylene.

In some of the presently described method embodiments comprising compounds of Formula (I), X$_1$ and X$_2$ are both O. In some embodiments, X$_1$ is at one of the 3'-position and 4'-position of ring A and X$_2$ is at one of the 3'-position and 4'-position of ring B. In some embodiments, n is an integer from 3 to 6.

In some embodiments of compounds of Formula (I), R$_3$ and R$_4$ are selected from the group consisting of:

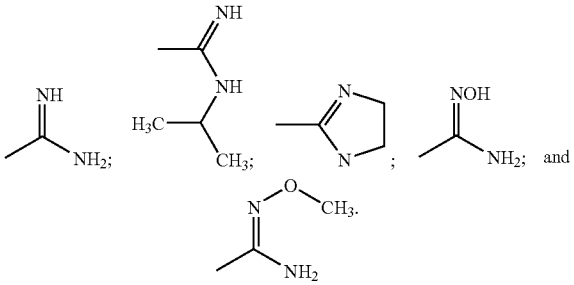

In some embodiments, R$_3$ is at one of the 5-position and 6-position of ring C, e.g., the benzofuran ring; and R$_4$ is at one of the 1"-position and 2"-position of ring B.

Particular compounds of Formula (I) include but are not limited to:

2-(3-(3-(4-Carbamimidoylphenoxy)propoxy)phenyl)benzofuran-5-carboxamidine (32);

2-(3-(3-(4-(N-Isopropylcarbamimidoyl)phenoxy)propoxy)phenyl)-N-isopropylbenzofuran-5-carboxamidine (33);

2-(2-(3-(3-(4-(4,5-Dihydro-1H-imidazol-2-yl)phenoxy) propoxy)phenyl)benzofuran-5-yl)-4,5-dihydro-1H-imidazole (34);

2-(3-(4-(4-Carbamimidoylphenoxy)butoxy)phenyl)benzofuran-5-carboxamidine (35);

2-(3-(4-(4-(N-Isopropylcarbamimidoyl)phenoxy)butoxy) phenyl)-N-isopropylbenzofuran-5-carboxamidine (36);

2-(2-(3-(4-(4-(4,5-Dihydro-1H-imidazol-2-yl)phenoxy) butoxy)phenyl)benzofuran-5-yl)-4,5-dihydro-1H-imidazole (37);

2-(3-(5-(4-Carbamimidoylphenoxy)pentyloxy)phenyl) benzofuran-5-carboxamidine (38);

2-(3-(5-(4-(N-Isopropylcarbamimidoyl)phenoxy)pentyloxy)phenyl)-N-isopropylbenzofuran-5-carboxamidine (39);

2-(2-(3-(5-(4-(4,5-Dihydro-1H-imidazol-2-yl)phenoxy) pentyloxy)phenyl)benzofuran-5-yl)-4,5-dihydro-1H-imidazole (40);

2-(3-(6-(4-Carbamimidoylphenoxy)hexyloxy)phenyl) benzofuran-5-carboxamidine (41);

2-(3-(6-(4-(N-Isopropylcarbamimidoyl)phenoxy)hexyloxy)phenyl)-N-isopropylbenzofuran-5-carboxamidine (42);

2-(2-(3-(6-(4-(4,5-Dihydro-1H-imidazol-2-yl)phenoxy) hexyloxy)phenyl)benzofuran-5-yl)-4,5-dihydro-1H-imidazole (43);

2-(4-(3-(4-Carbamimidoylphenoxy)propoxy)phenyl)benzofuran-5-carboxamidine (44);

2-(4-(3-(4-(N-Isopropylcarbamimidoyl)phenoxy)propoxy)phenyl)-N-isopropylbenzofuran-5-carboxamidine (45);

2-(2-(4-(3-(4-(4,5-Dihydro-1H-imidazol-2-yl)phenoxy) propoxy)phenyl)benzofuran-5-yl)-4,5-dihydro-1H-imidazole (46);

2-(4-(4-(4-Carbamimidoylphenoxy)butoxy)phenyl)benzofuran-5-carboxamidine (47);

2-(4-(4-(4-(N-Isopropylcarbamimidoyl)phenoxy)butoxy) phenyl)-N-isopropylbenzofuran-5-carboxamidine (48);

2-(2-(4-(4-(4-(4,5-Dihydro-1H-imidazol-2-yl)phenoxy) butoxy)phenyl)benzofuran-5-yl)-4,5-dihydro-1H-imidazole (49);

2-(4-(5-(4-Carbamimidoylphenoxy)pentyloxy)phenyl) benzofuran-5-carboxamidine (50);

2-(4-(5-(4-(N-Isopropylcarbamimidoyl)phenoxy)pentyloxy)phenyl)-N-isopropylbenzofuran-5-carboxamidine (51);

2-(2-(4-(5-(4-(4,5-Dihydro-1H-imidazol-2-yl)phenoxy) pentyloxy)phenyl)benzofuran-5-yl)-4,5-dihydro-1H-imidazole (52);

2-(4-(6-(4-Carbamimidoylphenoxy)hexyloxy)phenyl) benzofuran-5-carboxamidine (53);

2-(4-(6-(4-(N-Isopropylcarbamimidoyl)phenoxy)hexyloxy)phenyl)-N-isopropylbenzofuran-5-carboxamidine (54);

2-(2-(4-(6-(4-(4,5-Dihydro-1H-imidazol-2-yl)phenoxy) hexyloxy)phenyl)benzofuran-5-yl)-4,5-dihydro-1H-imidazole (55);

2-(3-(3-(4-Carbamimidoylphenoxy)propoxy)phenyl)benzofuran-6-carboxamidine (56);

2-(3-(3-(4-(N-Isopropylcarbamimidoyl)phenoxy)propoxy)phenyl)-N-isopropylbenzofuran-6-carboxamidine (57);

2-(2-(3-(3-(4-(4,5-Dihydro-1H-imidazole-2-yl)phenoxy) propoxy)phenyl)benzofuran-6-yl)-4,5-dihydro-1H-imidazole (58);

2-(3-(4-(4-Carbamimidoylphenoxy)butoxy)phenyl)benzofuran-6-carboxamidine (59);

2-(3-(4-(4-(N-Isopropylcarbamimidoyl)phenoxy)butoxy) phenyl)-N-isopropylbenzofuran-6-carboxamidine (60);

2-(2-(3-(4-(4-(4,5-Dihydro-1H-imidazol-2-yl)phenoxy) butoxy)phenyl)benzofuran-6-yl)-4,5-dihydro-1H-imidazole (61);

2-(3-(5-(4-Carbamimidoylphenoxy)pentyloxy)phenyl) benzofuran-6-carboxamidine (62);

2-(3-(5-(4-(N-Isopropylcarbamimidoyl)phenoxy)pentyloxy)phenyl)-N-isopropylbenzofuran-6-carboxamidine (63);

2-(2-(3-(5-(4-(4,5-Dihydro-1H-imidazol-2-yl)phenoxy) pentyloxy)phenyl)benzofuran-6-yl)-4,5-dihydro-1H-imidazole (64);

2-(3-(6-(4-Carbamimidoylphenoxy)hexyloxy)phenyl) benzofuran-6-carboxamidine (65);

2-(3-(6-(4-(N-Isopropylcarbamimidoyl)phenoxy)hexyloxy)phenyl)-N-isopropylbenzofuran-6-carboxamidine (66);

2-(2-(3-(6-(4-(4,5-Dihydro-1H-imidazol-2-yl)phenoxy) hexyloxy)phenyl)benzofuran-6-yl)-4,5-dihydro-1H-imidazole (67);

2-(4-(3-(4-Carbamimidoylphenoxy)propoxy)phenyl)benzofuran-6-carboxamidine (68);

2-(4-(3-(4-(N-Isopropylcarbamimidoyl)phenoxy)propoxy)phenyl)-N-isopropylbenzofuran-6-carboxamidine (69);

2-(2-(4-(3-(4-(4,5-Dihydro-1H-imidazole-2-yl)phenoxy) propoxy)phenyl)benzofuran-6-yl)-4,5-dihydro-1H-imidazole (70);

2-(4-(4-(4-Carbamimidoylphenoxy)butoxy)phenyl)benzofuran-6-carboxamidine (71);

2-(4-(4-(4-(N-Isopropylcarbamimidoyl)phenoxy)butoxy) phenyl)-N-isopropylbenzofuran-6-carboxamidine (72);

2-(2-(4-(4-(4-(4,5-Dihydro-1H-imidazol-2-yl)phenoxy) butoxy)phenyl)benzofuran-6-yl)-4,5-dihydro-1H-imidazole (73);

2-(4-(5-(4-Carbamimidoylphenoxy)pentyloxy)phenyl) benzofuran-6-carboxamidine (74);

2-(4-(5-(4-(N-Isopropylcarbamimidoyl)phenoxy)pentyloxy)phenyl)-N-isopropylbenzofuran-6-carboxamidine (75);

2-(2-(4-(5-(4-(4,5-Dihydro-1H-imidazol-2-yl)phenoxy) pentyloxy)phenyl)benzofuran-6-yl)-4,5-dihydro-1H-imidazole (76);

2-(4-(6-(4-Carbamimidoylphenoxy)hexyloxy)phenyl) benzofuran-6-carboxamidine (77);

2-(4-(6-(4-(N-Isopropylcarbamimidoyl)phenoxy)hexyloxy)phenyl)-N-isopropylbenzofuran-6-carboxamidine (78);

2-(2-(4-(6-(4-(4,5-Dihydro-1H-imidazol-2-yl)phenoxy) hexyloxy)phenyl)benzofuran-6-yl)-4,5-dihydro-1H-imidazole (79);

2-(4-(3-(4-(N-hydroxycarbamimidoyl)phenoxy)propoxy) phenyl)-N-hydroxybenzofuran-5-carboxamidine (182); and 2-(4-(5-(4-(N-hydroxycarbamimidoyl)phenoxy)pentyloxy)phenyl)-N-hydroxybenzofuran-5-carboxamidine (183).

With regard to the presently described method embodiments, compounds of Formula (II) are defined as having a structure as follows:

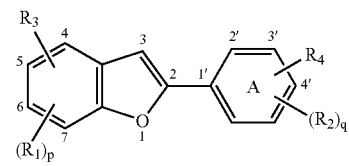

(II)

wherein:

p and q are integers from 0 to 3;

$R_1$ and $R_2$ are each independently selected from the group consisting of alkyl, halo, hydroxyl, alkoxyl, aryloxyl, and aralkyloxyl; and $R_3$ and $R_4$ are each independently selected from the group consisting of:

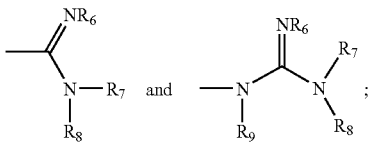

wherein:
$R_6$, $R_7$, $R_8$, and $R_9$ are each independently selected from the group consisting of H, alkyl, cycloalkyl, aryl, aralkyl, hydroxyl, alkoxyl, hydroxyalkyl, hydroxycycloalkyl, alkoxycycloalkyl, aminoalkyl, acyloxyl, alkylaminoalkyl, and alkoxycarbonyl; or
$R_6$ and $R_7$ together represent a $C_2$ to $C_{10}$ alkyl, $C_2$ to $C_{10}$ hydroxyalkyl, or $C_2$ or $C_{10}$ alkylene.

In some of the presently descried method embodiments comprising compounds of Formula (II), $R_3$ and $R_4$ are selected from the group consisting of:

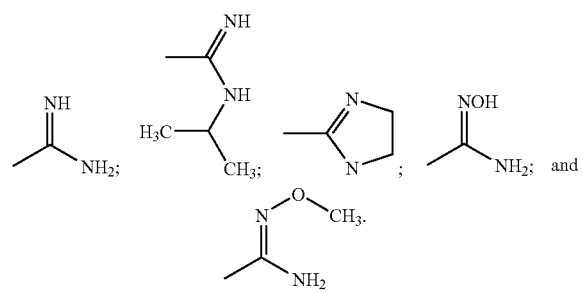

In some embodiments, $R_3$ is at one of the 5-position and 6-position of ring C, and $R_4$ is at one of the 3'-position and 4'-position of ring A. In some embodiments, p is 1 and $R_1$ is —OCH$_3$. In some embodiments, $R_1$ is in the 7-position of ring C.

Particular compounds of Formula (II) include, but are not limited to:

2-(4-carbamimidoylphenyl)benzofuran-5-carboxamidine (163);

2-(4-(N-isopropylcarbamimidoyl)phenyl)-N-isopropyl-benzofuran-5-carboxamidine (164);

2-(4-(5-(4,5-dihydro-1H-imidazol-2-yl)benzofuran-2-yl)phenyl)-4,5-dihydro-1H-imidazole (165);

2-(3-carbamimidoylphenyl)benzofuran-5-carboxamidine (166);

2-(3-(N-isopropylcarbamimidoyl)phenyl)-N-isopropyl-benzofuran-5-carboxamidine (167);

2-(3-(5-(4,5-dihydro-1H-imidazol-2-yl)benzofuran-2-yl)phenyl)-4,5-dihydro-1H-imidazole (168);

2-(3-carbamimidoylphenyl)benzofuran-6-carboxamidine (169);

2-(3-(N-isopropylcarbamimidoyl)phenyl)-N-isopropyl-benzofuran-6-carboxamidine (170);

2-(3-(6-(4,5-dihydro-1H-imidazol-2-yl)benzofuran-2-yl)phenyl)-4,5-dihydro-1H-imidazole (171);

2-(4-carbamimidoylphenyl)benzofuran-6-carboxamidine (172);

2-(4-(N-isopropylcarbamimidoyl)phenyl)-N-isopropyl-benzofuran-6-carboxamidine (173);

2-(4-(6-(4,5-dihydro-1H-imidazol-2-yl)benzofuran-2-yl)phenyl)-4,5-dihydro-1H-imidazole (174);

2-(4-carbamimidoylphenyl)-7-methoxybenzofuran-5-carboxamidine (175);

2-(4-(N-isopropylcarbamimidoyl)phenyl)-N-isopropyl-7-methoxybenzofuran-5-carboxamidine (176);

2-(4-(5-(4,5-dihydro-1H-imidazol-2-yl)-7-methoxybenzofuran-2-yl)phenyl)-4,5-dihydro-1H-imidazole (177);

2-(4-(N-hydroxycarbamimidoyl)phenyl)-N-hydroxybenzofuran-5-carboxamidine (178);

2-(4-(N-methoxycarbamimidoyl)phenyl)-N-methoxybenzofuran-5-carboxamidine (179);

2-(3-(N-hydroxycarbamimidoyl)phenyl)-N-hydroxybenzofuran-6-carboxamidine (180); and 2-(4-(N-hydroxycarbamimidoyl)phenyl)-N-hydroxybenzofuran-6-carboxamidine (181).

With regard to the presently described method embodiments, compounds of Formula (III) are defined as having a structure as follows:

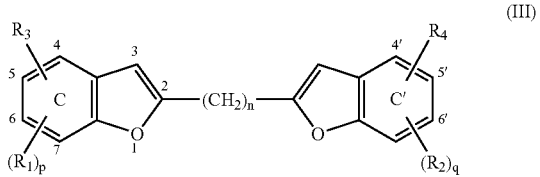

wherein:
n is an integer from 1 to 8;
p and q are integers from 0 to 3;
$R_1$ and $R_2$ are each independently selected from the group consisting of alkyl, halo, hydroxyl, alkoxyl, aryloxyl, and aralkyloxyl; and
$R_3$ and $R_4$ are each independently selected from the group consisting of:

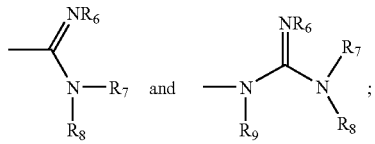

wherein:
$R_6$, $R_7$, $R_8$, $R_9$ are each independently selected from the group consisting of H, alkyl, cycloalkyl, aryl, aralkyl, hydroxyl, alkoxyl, hydroxyalkyl, hydroxycycloalkyl, alkoxycycloalkyl, aminoalkyl, acyloxyl, alkylaminoalkyl, and alkoxycarbonyl; or
$R_6$ and $R_7$ together represent a $C_2$ to $C_{10}$ alkyl, $C_2$ to $C_{10}$ hydroxyalkyl, or $C_2$ or $C_{10}$ alkylene.

In some of the presently described method embodiments comprising compounds of Formula (III), $R_3$ and $R_4$ are selected from the group consisting of:

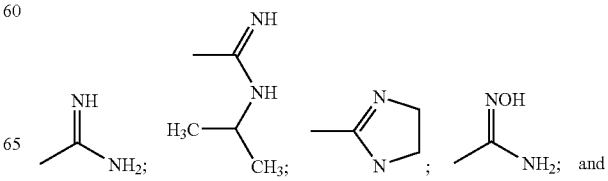

-continued

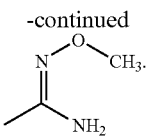

In some embodiments, $R_3$ is at one of the 4-position, 5-position, and 6-position or ring C. In some embodiments, $R_4$ is at one of the 4'-position, 5'-position, and 6'-position of ring C. In some embodiments, n is an integer from 1 to 5.

Particular compounds of Formula (III) include, but are not limited to:

2-((4-Amidinobenzofuran-2-yl)methyl)benzofuran-4-carboxamidine (1);
2-((4-Amidinobenzofuran-2-yl)methyl)-N-isopropylbenzofuran-4-carboxamidine (2);
Bis(4-(4,5-dihydro-1H-imidazol-2-yl)benzofuran-2-yl)methane (3);
2-((5-Amidinobenzofuran-2-yl)methyl)benzofuran-5-carboxamidine (4);
2-((5-Amidinobenzofuran-2-yl)methyl)-N-isopropylbenzofuran-5-carboxamidine (5);
Bis(5-(4,5-dihydro-1H-imidazol-2-yl)benzofuran-2)methane (6);
Bis(6-(4,5-dihydro-1H-imidazol-2-yl)benzofuran-2-yl)methane (7);
2-(2-(5-Amidinobenzofuran-2-yl)ethyl)benzofuran-5-carboxamidine (8);
2-(2-(5-Amidinobenzofuran-2-yl)ethyl)-N-isopropylbenzofuran-5-carboxamidine (9);
4,5-Dihydro-2-(2-(2-(5-(4,5-dihydro-1H-imidazol-2-yl)benzofuran-2-yl)ethyl)benzofuran-5-yl)-1H-imidazole (10);
2-(2-(6-Amidinobenzofuran-2-yl)ethyl)benzofuran-6-carboxamidine (11);
2-(2-(6-Amidinobenzofuran-2-yl)ethyl)-N-isopropylbenzofuran-6-carboxamidine (12);
4,5-dihydro-2-(2-(2-(6-(4,5-dihydro-1H-imidazol-2-yl)benzofuran-2-yl)ethyl)benzofuran-6-yl)-1H-imidazole (13);
2-(3-(5-Amidinobenzofuran-2-yl)propyl)benzofuran-5-carboxamidine (14);
2-(3-(5-Amidinobenzofuran-2-yl)propyl)-N-isopropylbenzofuran-5-carboxamidine (15);
4,5-Dihydro-2-(2-(3-(5-(4,5-dihydro-1H-imidazol-2-yl)benzofuran-2-yl)propyl)benzofuran-5-yl)-1H-imidazole (16);
2-(3-(6-Amidinobenzofuran-2-yl)propyl)benzofuran-6-carboxamidine (17);
2-(3-(6-Amidinobenzofuran-2-yl)propyl)-N-isopropylbenzofuran-6-carboxamidine (18);
4,5-Dihydro-2-(2-(3-(6-(4,5-dihydro-1H-imidazol-2-yl)benzofuran-2-yl)propyl)benzofuran-6-yl)-1H-imidazole (19);
2-(4-(5-Amidinobenzofuran-2-yl)butyl)benzofuran-5-carboxamidine (20);
2-(4-(5-Amidinobenzofuran-2-yl)butyl)-N-isopropylbenzofuran-5-carboxamidine (21);
4,5-Dihydro-2-(2-(4-(5-(4,5-dihydro-1H-imidazol-2-yl)benzofuran-2-yl)butyl)benzofuran-5-yl)-1H-imidazole (22);
2-(4-(6-Amidinobenzofuran-2-yl)butyl)benzofuran-6-carboxamidine (23);
2-(4-(6-Amidinobenzofuran-2-yl)butyl)-N-isopropylbenzofuran-6-carboxamidine (24);
4,5-Dihydro-2-(2-(4-(6-(4,5-dihydro-1H-imidazol-2-yl)benzofuran-2-yl)butyl)benzofuran-6-yl)-1H-imidazole (25);
2-(5-(5-Amidinobenzofuran-2-yl)pentyl)benzofuran-5-carboxamidine (26);
2-(5-(5-Amidinobenzofuran-2-yl)pentyl)-N-isopropyl-benzofuran-5-carboxamidine (27);
4,5-Dihydro-2-(2-(5-(5-(4,5-dihydro-1H-imidazol-2-yl)benzofuran-2-yl)pentyl)benzofuran-5-yl)-1H-imidazole (28);
2-(5-(6-Amidinobenzofuran-2-yl)pentyl)benzofuran-6-carboxamidine (29);
2-(5-(6-Amidinobenzofuran-2-yl)pentyl)-N-isopropyl-benzofuran-6-carboxamidine (30);
4,5-Dihydro-2-(2-(5-(6-(4,5-dihydro-1H-imidazol-2-yl)benzofuran-2-yl)pentyl)benzofuran-6-yl)-1H-imidazole (31);
2-(5-(6-(N-hydroxycarbamimidoyl)benzofuran-2-yl)pentyl)-N-hydroxybenzofuran-6-carboxamidine (184);
2-(3-(5-(N-hydroxycarbamimidoyl)benzofuran-2-yl)propyl)-N-hydroxybenzofuran-5-carboxamidine (185);
2-(4-(5-(N-hydroxycarbamimidoyl)benzofuran-2-yl)butyl)-N-hydroxybenzofuran-5-carboxamidine (186);
2-(5-(6-(N-methoxycarbamimidoyl)benzofuran-2-yl)pentyl)-N-methoxybenzofuran-6-carboxamidine (187);
2-(3-(5-(N-methoxycarbamimidoyl)benzofuran-2-yl)propyl)-N-methoxybenzofuran-5-carboxamidine (188);
2-(4-(5-(N-methoxycarbamimidoyl)benzofuran-2-yl)butyl)-N-methoxybenzofuran-5-carboxamidine (189);
2-(2-(5-(N-hydroxycarbamimidoyl)benzofuran-2-yl)ethyl)-N-hydroxybenzofuran-5-carboxamidine (190);
2-(2-(5-(N-methoxycarbamimidoyl)benzofuran-2-yl)ethyl)-N-methoxybenzofuran-5-carboxamidine (191);
2-(5-(5-(N-hydroxycarbamimidoyl)benzofuran-2-yl)pentyl)-N-hydroxybenzofuran-5-carboxamidine (192); and
2-(5-(5-(N-methoxycarbamimidoyl)benzofuran-2-yl)pentyl)-N-methoxybenzofuran-5-carboxamidine (193).

The subject treated in the presently disclosed subject matter in its many embodiments is desirably a human subject, although it is to be understood the methods described herein are effective with respect to all vertebrate species, which are intended to be included in the term "subject". The methods described herein are particularly useful in the treatment and/or prevention of infections diseases in warm-blooded vertebrates. Thus, the methods can be used as treatment for mammals and birds.

More particularly, provided herein is the treatment of mammals such as humans, as well as those mammals of importance due to being endangered (such as Siberian tigers), of economical importance (animals raised on farms for consumption by humans) and/or social importance (animals kept as pets or in zoos) to humans, for instance, carnivores other than humans (such as cats and dogs), swine (pigs, hogs, and wild boars), ruminants (such as cattle, oxen, sheep, giraffes, deer, goats, bison, and camels), and horses. Also provides herein is the treatment of birds, including the treatment of those kinds of birds that are endangered, kept in zoos, as well as fowl, and more particularly domesticated fowl, i.e., poultry, such as turkeys, chickens, ducks, geese, guinea fowl, and the like, as they also are of economical importance to humans. Thus, embodiments of the methods described herein include the treatment of livestock, including, but not limited to, domesticated swine (pigs and hogs), ruminants, horses, poultry, and the like.

III. General Processes for the Synthesis of Cationic Substituted Benzofurans of Formulae (I-III)

The synthetic procedures presented below represent novel methods of producing the presently disclosed compounds. The method are outlined in the Schemes presented below and details are described in the Examples. Descriptions and analysis of novel compounds also are described in the text.

In some embodiments of the presently described subject matter, a process for the synthesis of unsymmetrical benzofuran diamidines of Formula (I) is disclosed. In some embodiments of the presently described subject matter, a process for the synthesis of 2-aryl benzofuran-containing dications of Formula (II) is disclosed. In some embodiments of the presently described subject matter, a process for the synthesis of bis-benzofuran diamidines of Formula (III) is disclosed.

A. General Process for the Synthesis of Bis-Benzofuran Diamidines (1-7) of Formula (III) with a Methylene Linking Group (i) Process for the Synthesis of Bis-Benzofuranmethanones (82, 83)

Referring now to Scheme 1, bis-benzofuranmethanones (82, 83) are synthesized by: (a) dissolving the appropriate brominated hydroxybenzaldehyde (80, 81) in dry butanone to form a first reaction mixture; (b) refluxing the first reaction mixture for 30 min; (c) cooling the first reaction mixture; (d) adding a solution of 1,3-dichloroacetone in dry butanone to the first reaction mixture to form a second reaction mixture; (e) refluxing the second reaction mixture for four hrs; (f) cooling the second reaction mixture; (g) filtering the second reaction mixture; (h) concentrating the second reaction mixture to form a residue; and (i) recrystallizing the residue from $CHCl_3$ to form the desired bis-benzofuranmethanone (82, 83).

(ii) Process for the Synthesis of Bis-Benzofuranmethanes (84, 85)

Referring again to Scheme 1, bis-benzofuranmethanes (84, 85) are synthesized by: (a) dissolving aluminum chloride in dry diethyl ether to form a first reaction mixture; (b) adding the first reaction mixture under an inert gas to a stirred suspension of lithium aluminum hydride in dry diethyl ether to form a second reaction mixture; (c) adding the appropriate bis-benzofuranmethanone (82, 83) to the second reaction mixture to form a third reaction mixture; (d) stirring the third reaction mixture for one hr; (e) adding aqueous HCl to the third reaction mixture to form a fourth reaction mixture; (f) extracting the fourth reaction mixture with diethyl ether to form an ether solution; (g) drying the ether solution; and (h) concentrating the ether solution to form the desired bis-benzofuranmethane (84, 85).

(iii) Process for the Synthesis of Bis-Benzofuranmethane Carbodinitriles (86, 87)

Referring again to Scheme 1, bis-benzofuranmethane carbodinitriles (86, 87) are synthesized by: (a) mixing the appropriate bis-benzofuranmethane (84, 85) and CuCN in dry quinoline to form a first reaction mixture; (b) refluxing the first reaction mixture for two hrs; (c) pouring the first reaction mixture into a 2 M HCl solution to form a second reaction mixture; (d) stirring the second reaction mixture for one hr to form a precipitate; (e) filtering the precipitate; (f) drying the precipitate; (g) suspending the precipitate in chlorobenzene to form a third reaction mixture; (h) stirring the third reaction mixture for one hr; (i) separating the insoluble material to form a filtrate; (j) concentrating the filtrate to form a residue; and (k) purifying the residue by column chromatography to form the desired bis-benzofuranmethane carbodinitrile (86, 87).

(iv) Process for the Synthesis of Bis-Benzofuran Diamidines (1-7) of Formula (III) with a Methylene Linking Group Referring again to Scheme 1, bis-benzofuran diamidines (1-7) of Formula (III) with a methylene linking group are synthesized from the appropriate bis-benzofuranmethane carbodinitriles (86-88) by: (a) mixing dry 1,4-dioxane and dry ethanol to form a first reaction mixture; (b) saturating the first reaction mixture with anhydrous gaseous HCl to form a second reaction mixture; (c) adding the appropriate bis-benzofuranmethane carbodinitrile (86-88) to the second reaction mixture to form a third reaction mixture; (d) diluting the third reaction mixture with dry ether to form a diimidate; (e) collecting the diimidate under an inert has; (f) washing the diimidate with diethyl ether; (g) drying the diimidate; (h) suspending the diimidate in dry ethanol to form a fourth reaction mixture; (i) saturating the fourth reaction mixture with the appropriate amine to form a fifth reaction mixture; (j) diluting the fifth reaction mixture with diethyl ether; (k) cooling the diluted reaction mixture to form a precipitate; (l) collecting the precipitate; (m) washing the precipitate with diethyl ether; (n) drying the precipitate; and (o) recrystallizing the precipitate from aqueous HCl to form the dihydrochloride salt of the desired bis-benzofuran diamidine (1-7).

B. General Process for the Synthesis of Bis-Benzofuran Diamidines (8-13) of Formula (III) with an Ethylene Linking Group (i) Process for the Synthesis of Benzofuran Carboxylates (95-102)

Referring now to Scheme 2, methyl-(hydroxypropyl)benzofuran carboxylates (95-96) are synthesized by: (a) mixing the appropriate methyl-hydroxy iodobenzoate (93, 94) with 4-pentyn-1-ol and copper (I) oxide in dry pyridine to form a first reaction mixture; (b) stirring the first reaction mixture overnight; (c) cooling the first reaction mixture to room temperature; (d) diluting the cooled first reaction mixture with EtOAc to form a second reaction mixture; (e) filtering the second reaction mixture; (f) concentrating the second reaction mixture to form a residue; (g) dissolving the residue in EtOAc to form a solution; (h) washing the solution with HCl to form a washed solution; (i) washing the washed solution with brine to form a second washed solution; (j) drying the second washed solution over $Na_2SO_4$; (k) filtering the dried second washed solution; (l) concentrating the filtered second washed solution; (m) purifying the concentrated second washed solution by column chromatography; and (n) recrystallizing the purified second washed solution in hexanes/diethyl ether to form the desired methyl-(hydroxypropyl)benzofuran carboxylate (95, 96).

Referring again to Scheme 2, methyl-(formylethyl)benzofuran carboxylates (97, 98) are synthesized by: (a) placing a solution of oxalyl chloride in $CH_2Cl_2$ under argon into a reaction flask to form a first reaction mixture; (b) cooling the first reaction mixture to −70° C.; (c) adding dropwise a mixture of DMSO and dry $CH_2Cl_2$ to form a second reaction mixture; (d) adding a solution of the appropriate methyl-(hydroxypropyl)benzofuran carboxylate (95, 96) in $CH_2Cl_2$ to form a third reaction mixture; (e) stirring the third reaction mixture at −70° C. for 60 min; (f) adding triethylamine dropwise to the third reaction mixture at −60° C. to form a fourth reaction mixture; (g) allowing the fourth reaction mixture to warm to room temperature; (h) adding water to the fourth reaction mixture to form a fifth reaction mixture; (i) stirring the fifth reaction mixture; (j) separating the organic layer of the fifth reaction mixture to form a first organic fraction; (k) extracting the aqueous layer of the fifth reaction mixture with $CH_2Cl_2$ to form a second organic fraction; (l) combining the first and the second organic fractions to form a combined organic fraction; (m) washing the combined organic fraction with 2 M HCl to form a washed combined organic fraction; (n) drying the washed combined organic fraction over Na₂SO₄ to form a dried combined organic fraction; (o) concentrating the dried combined organic fraction to form a concentrated combined organic fraction; (p) purifying the concentrated combined organic fraction by column chromatography to form a purified combined organic fraction; and (q) recrystallizing the purified combined organic fraction in EtOAc/hexanes to form the desired methyl-(formylethyl) benzofuran carboxylate (97, 98).

Referring again to Scheme 2, methyl-(but-3-ynyl)benzofuran carboxylates (99, 100) are synthesized by: (a) mixing dimethyl-1-diazo-2-oxopropylphosphonate and dry methanol to form a first reaction mixture; (b) adding the first reaction mixture to a solution of K₂CO₃ in dry methanol to form a second reaction mixture; (c) stirring the second reaction mixture until complete conversion was obtained; (d) concentrating the second reaction mixture to form a residue; (e) diluting the residue with diethyl ether to form a diluted residue; (f) washing the diluted residue with water to form a washed residue; (g) drying the washed residue over CaCl₂ to form a dried residue; (h) removing the solvent to form a residue; and (i) recrystallizing the residue in EtOAc/hexanes to form the appropriate methyl-(but-3-ynyl)benzofuran carboxylates (99, 100).

Referring again to Scheme 2, methyl-(methoxycarbonyl) benzofuran-2-yl)ethyl)benzofuran carboxylates (101, 102) are synthesized by: (a) mixing the appropriate methyl-hydroxy iodobenzoate (93, 94) with the appropriate methyl-(but-3-ynyl)benzofuran carboxylate (99, 100) and copper (I) oxide in dry pyridine to form a first reaction mixture; (b) stirring the first reaction mixture overnight; (c) cooling the first reaction mixture to room temperature; (d) diluting the cooled first reaction mixture with EtOAc to form a second reaction mixture; (e) filtering the second reaction mixture; (f) concentrating the second reaction mixture to form a residue; (g) dissolving the residue in EtOAc to form a solution; (h) washing the solution with HCl to form a washed solution; (i) washing the washed solution with brine to form a second washed solution; (j) drying the second washed solution over Na₂SO₄; (k) filtering the dried second washed solution; (l) concentrating the filtered second washed solution; (m) purifying the concentrated second washed solution by column chromatography; and (n) recrystallizing the purified second washed solution in hexanes/diethyl ether to form the desired methyl-(methoxycarbonyl)benzofuran-2-yl)ethyl)benzofuran carboxylate (101, 102).

(ii) Process for the Syntheses of Bis-Benzofuran Carbodinitriles (103, 104)

Referring again to Scheme 2, ((cyanobenzofuran-2-yl) ethyl)benzofuran carbonitriles (103, 104) are synthesized by: (a) bubbling anhydrous NH₃ through dry o-xylene for 20 min at 0° C. to form a first reaction mixture; (b) adding a 2.0 M solution of AlMe₃ in toluene to the first reaction mixture to form a second reaction mixture; (c) passing NH₃ through the second reaction mixture for 20 min to form a third reaction mixture; (d) stirring the third reaction mixture at room temperature for one hr; (e) adding the appropriate methyl-(methoxycarbonyl)benzofuran-2-yl)ethyl)benzofuran carboxylate (101, 102) to the third reaction mixture to form a fourth reaction mixture; (f) allowing the fourth reaction mixture to cool to room temperature; (g) diluting the fourth reaction mixture with CHCl₃ to form a diluted fourth reaction mixture; (h) adding water dropwise to the diluted fourth reaction mixture with vigorous stirring to form a fifth reaction mixture; (i) filtering off inorganic solids from the fifth reaction mixture to form an organic filtrate; (j) separating and concentrating the organic filtrate to form a residue; and (k) purifying the residue by column chromatography to form the desired ((cyanobenzofuran-2-yl)ethyl)benzofuran carbonitrile (103, 104).

(iii) Process for the Synthesis of Bis-Benzofuran Diamidines (8-13) of Formula (III) with an Ethylene Linking Group Referring again to Scheme 2, bis-benzofuran diamidines (8-13) of Formula (III) with an ethylene linking group are synthesized from the appropriate bis-benzofuran carbodinitriles (103, 104) by: (a) mixing dry 1,4-dioxane and dry ethanol to form a first ration mixture; (b) saturating the first reaction mixture with anhydrous gaseous HCl to form a second reaction mixture; (c) adding the appropriate bis-benzofuran carbodinitrile (103, 104) to the second reaction mixture to form a third reaction mixture; (d) diluting the third reaction mixture with dry ether to form a diimidate; (e) collecting the diimidate under an inert gas; (f) washing the diimidate with diethyl ether; (g) drying the diimidate; (h) suspending the diimidate in dry ethanol to form a fourth reaction mixture; (i) saturating the fourth reaction mixture with the appropriate amine to form a fifth reaction mixture; (j) diluting the fifth reaction mixture with diethyl ether; (k) cooling the diluted reaction mixture to form a precipitate; (l) collecting the precipitate; (m) washing the precipitate with diethyl ether; (n) drying the precipitate; and (o) recrystallizing the precipitate from aqueous HCl to form the dihydrochloride salt of the desired bis-benzofuran diamidine (8-13).

C. General Process for the Synthesis of Bis-Benzofuran Diamidines (14-31) of Formula (III) with a —(CH₂)— Linking Group (i) Process for the Synthesis of methyl-((methoxycarbonyl)benzofuran-2-yl)alkyl)benzofuran carboxylates (105-110)

Referring now to Scheme 3, methyl-((methoxycarbonyl) benzofuran-2-yl)alkyl)benzofuran carboxylates (105-110) are synthesized by: (a) mixing the appropriate methyl-hydroxy iodobenzoate (93, 94) with the appropriate alkadiyne, e.g., 1,6-heptadiyne; 1,7-octadiyne; or 1,8-nonadiyne, and copper (I) oxide in dry pyridine to form a first reaction mixture, or mixing the appropriate methyl-hydroxy iodobenzoate (93, 94) with the appropriate alkadiyne, e.g., 1,6-heptadiyne; 1,7-octadiyne; or 1,8-nonadiyne, with PdCl₂(PPH₃)₂, CuI and 1,1,3,3-tetramethylguanidine in N,N'-dimethylformamide to form a first reaction mixture; (b) stirring the first reaction mixture overnight; (c) cooling the first reaction mixture to room temperature; (d) diluting the cooled first reaction mixture with EtOAc to form a second reaction mixture; (e) filtering the second reaction mixture; (f) concentrating the second reaction mixture to form a residue; (g) dissolving the residue in EtOAc to form a solution; (h) washing the solution with HCl to form a washed solution; (i) washing the washed solution with brine to form a second washed solution; (j) drying the second washed solution over Na₂SO₄; (k) filtering the dried second washed solution; (l) concentrating the filtered second washed solution; (m) purifying the concentrated second washed solution by column chromatography; and (n) recrystallizing the purified second washed solution in hexanes/diethyl ether to form the desired methyl-((methoxycarbonyl)benzofuran-2-yl)alkyl)benzofuran carboxylate (105-110).

(ii) Process for the Synthesis of ((cyanobenzofuran-2-yl) alkyl)benzofuran carbonitriles (111-116)

Referring again to Scheme 3, ((cyanobenzofuran-2-yl) alkyl)benzofuran carbonitriles (111-116) are synthesized by: (a) bubbling anhydrous NH₃ through dry o-xylene for 20 min at 0° C. to form a first reaction mixture; (b) adding a 2.0 M solution of AlMe₃ in toluene to the first reaction mixture to form a second reaction mixture; (c) passing NH$_3$ through the second reaction mixture for 20 min to form a third reaction mixture; (d) stirring the third reaction mixture at room temperature for one hr; (e) adding the appropriate methyl-((methoxycarbonyl)benzofuran-2-yl)alkyl)benzofuran carboxylate (105-110) to the third reaction mixture to form a fourth reaction mixture; (f) allowing th fourth reaction mixture to cool to room temperature; (g) diluting the fourth reaction mixture with CHCl$_3$ to form a diluted fourth reaction mixture; (h) adding water dropwise to the diluted fourth reaction mixture with vigorous stirring to form a fifth reaction mixture; (i) filtering off inorganic solids from the fifth reaction mixture to form an organic filtrate; (j) separating and concentrating the organic filtrate to form a residue; and (k) purifying the residue by column chromatography to form the desired ((cyanobenzofuran-2-yl)alkyl)benzofuran carbonitrile (111-116).

(iii) Process for the Synthesis of Bis-Benzofuran Diamidines (14-31) of Formula (III) with a —(CH$_2$)— Linking Group Referring again to Scheme 3, bis-benzofuran diamidines (14-31) of Formula (III) with a —(CH$_2$)— linking group are synthesized from the appropriate bis-benzofuran carbodinitriles (111-116) by: (a) mixing dry 1,4-dioxane and dry ethanol to form a first reaction mixture; (b) saturating the first reaction mixture with anhydrous gaseous HCl to form a second reaction mixture; (c) adding the appropriate bis-benzofuran carbodinitrile (111-116) to the second reaction mixture to form a third reaction mixture; (d) diluting the third reaction mixture with dry ether to form a diimidate; (e) collecting the diimidate under an inert gas; (f) washing the diimidate with diethyl ether; (g) drying the diimidate; (h) suspending the diimidate in dry ethanol to form a fourth reaction mixture; (i) saturating the fourth reaction mixture with the appropriate amine to form a fifth reaction mixture; (j) diluting the fifth reaction mixture with diethyl ether; (k) cooling the diluted reaction mixture to form a precipitate; (l) collecting the precipitate; (m) washing the precipitate with diethyl ether; (n) drying the precipitate; and (o) recrystallizing the precipitate from aqueous HCl to form the dihydrochloride salt of the desired bis-benzofuran diamidine (14-31).

D. General Process for the Synthesis of Unsymmetrical Benzofuran Diamidines (32-79) of Formula (I)

(i) Process for the Synthesis of (methoxyphenyl)benzofuran carbonitriles (120, 123, 124) and (methoxyphenyl)benzofuran carboxylates (121, 122)

Referring now to Scheme 4, (methoxyphenyl)benzofuran carbonitriles (120, 123, 124) and (methoxyphenyl)benzofuran carboxylates (121, 122) are synthesized by: (a) mixing the appropriate hydroxy-iodo benzoate (94) or the appropriate hydroxy-iodo benzonitrile (117) and the appropriate methoxyphenylacetylene (118, 119) with copper (I) oxide in dry pyridine to form a first reaction mixture; (b) stirring the first reaction mixture overnight; (c) cooling the first reaction mixture to room temperature; (d) diluting the cooled first reaction mixture with EtOAc to form a second reaction mixture; (e) filtering the second reaction mixture; (f) concentrating the second reaction mixture to form a residue; (g) dissolving the residue in EtOAc to form a solution; (h) washing the solution with HCl to form a washed solution; (i) washing the washed solution with brine to form a second washed solution; (j) drying the second washed solution over Na$_2$SO$_4$; (k) filtering the dried second washed solution; (l) concentrating the filtered second washed solution; (m) purifying the concentrated second washed solution by column chromatography; and (n) recrystallizing the purified second washed solution in hexanes/diethyl ether to form the desired (methoxyphenyl)benzofuran carbonitrile (120) and (methoxyphenyl)benzofuran carboxylate (121, 122).

Referring again to Scheme4, (methoxyphenyl)benzofuran carbonitriles (123, 124) are synthesized by: (a) bubbling anhydrous NH$_3$ through dry o-xylene for 20 min at 0° C. to form a first reaction mixture; (b) adding a 2.0 M solution of AlMe$_3$ in toluene to the first reaction mixture to form a second reaction mixture; (c) passing NH$_3$ through the second reaction mixture for 20 min to form a third reaction mixture; (d) stirring the third reaction mixture at room temperature for one hr; (e) adding the appropriate (methoxyphenyl)benzofuran carboxylate (121, 122) to the third reaction mixture to form a fourth reaction mixture; (f) allowing the fourth reaction mixture to cool to room temperature; (g) diluting the fourth reaction mixture with CHCl$_3$ to form a diluted fourth reaction mixture; (h) adding water dropwise to the diluted fourth reaction mixture with vigorous stirring to form a fifth reaction mixture; (i) filtering off inorganic solids from the fifth reaction mixture to form an organic filtrate; (j) separating and concentrating the organic filtrate to form a residue; and (k) purifying the residue by column chromatography to form the desired (methoxyphenyl)benzofuran carbonitrile (123, 124).

(ii) Process for the Synthesis of 2-(hydroxyphenyl)benzofuran carbonitriles (125, 127, 128)

Referring again to Scheme 4, 2-(hydroxyphenyl)benzofuran carbonitriles (125, 127, 128) are synthesized by: (a) adding the appropriate (methoxyphenyl)benzofuran carbonitrile (120, 123, 124) to a melted pyridine hydrochloride at 160-180° C. to form a first reaction mixture; (b) stirring the first reaction mixture at 180° C. for 2.5 hr; (c) cooling the first reaction mixture; (d) diluting the first reaction mixture with water and 1 M HCl to form a diluted first reaction mixture; (e) stirring the diluted first reaction mixture for 30 min to form a precipitate; (f) separating the precipitate; (g) washing the precipitate with 1 M HCl and water; (h) drying the washed precipitate to form a residue; (i) purifying the residue by flash chromatography to form a purified residue; and (j) recrystallizing the purified residue to form the desired 2-(hydroxyphenyl)benzofuran carbonitrile (125, 127, 128).

(iii) Process for the synthesis of (4-cyanophenoxy)alkoxy)phenyl)benzofuran carbonitriles (133-148)

Referring now to Scheme 5, (4-cyanophenoxy)alkoxy)phenyl)benzofuran carbonitriles (133-148) are synthesized by: (a) mixing the appropriate 2-(hydroxyphenyl)benzofuran carbonitrile (125-128) with K$_2$CO$_3$ in dry DMF to form the first reaction mixture; (b) heating the first reaction mixture to 60° C.; (c) adding the appropriate (bromoalkoxy)benzonitrile (129-132) to the first reaction mixture to form a second reaction mixture; (d) maintaining the second reaction mixture at 80-100° C. overnight; (e) cooling the second reaction mixture to room temperature; (f) pouring the second reaction mixture into iced water and stirring for 30 min to form a precipitate; (g) separating the precipitate by filtration; (h) washing the separated precipitate with water and ethanol; (i) drying the washed precipitate; and (j) recrystallizing the washed precipitate from a mixture of DMF and ethanol to form the desired (4-cyanophenoxy)alkoxy)phenyl)benzofuran carbonitrile (133-148).

(iv) Process for the Synthesis of Unsymmetrical Benzofuran Diamidines (32-79) of Formula (I)

Referring now to Scheme 5, unsymmetrical benzofuran diamidines (32-79) of Formula I are synthesized from the appropriate bis-benzofuran carbodinitriles by: (a) mixing dry 1,4-dioxane and dry ethanol to form a first reaction mixture; (b) saturating the first reaction mixture with anhydrous gaseous HCl to form a second reaction mixture; (c) adding the appropriate (4-cyanophenoxy)alkoxy)phenyl)benzofuran carbonitrile (133-148) to the second reaction mixture to form a third reaction mixture; (d) diluting the third reaction mixture with dry ether to form a diimidate; (e) collecting the diimidate under an inert gas; (f) washing the diimidate with diethyl ether; (g) drying the diimidate; (h) suspending the diimidate in dry ethanol to form a fourth reaction mixture; (i) saturating the fourth reaction mixture with the appropriate amine to form a fifth reaction mixture; (j) diluting the fifth reaction mixture with diethyl ether; (k) cooling the diluted reaction mixture to form a precipitate; (l) collecting the precipitate; (m) washing the precipitate with diethyl ether; (n) drying the precipitate; and (o) recrystallizing the precipitate from aqueous HCl to form the dihydrochloride salt of the desired unsymmetrical benzofuran diamidine (32-79) of Formula (I).

E. General Process for the Synthesis of 2-aryl Benzofuran-Containing Dications (163-177) of Formula (II)

(i) Process for the Synthesis of (cyanophenyl)benzofuran carbonitriles (151, 152), (methyl-oxycarbonylphenyl)benzofuran carboxylates (155, 156), and ((cyanophenyl)methoxy) benzofurancarbaldehydes (160)

Referring now to Scheme 6, (cyanophenyl)benzofuran carbonitriles (151, 152), (methyl-oxycarbonylphenyl)benzofuran carboxylates (155, 156), and ((cyanophenyl)methoxy) benzofurancarbaldehydes (160) are synthesized by: (a) mixing the appropriate hydroxy-iodo benzoate (94), the appropriate hydroxy-iodo benzonitrile (117), or the appropriate hydroxymethoxyiodobenzaldehyde (159) and the appropriate cyanophenylacetylene (149, 150) or the appropriate ethynylbenzoate (153, 154) with copper (I) oxide in dry pyridine to form a first reaction mixture; (b) stirring the first reaction mixture overnight; (c) cooling the first reaction mixture to room temperature; (d) diluting the cooled first reaction mixture with EtOAc to form a second reaction mixture; (e) filtering the second reaction mixture; (f) concentrating the second reaction mixture to form a residue; (g) dissolving the residue in EtOAc to form a solution; (h) washing the solution with HCl to form a washed solution; (i) washing the washed solution with brine to form a second washed solution; (j) drying the second washed solution over $Na_2SO_4$; (k) filtering the dried second washed solution; (l) concentration the filtered second washed solution; (m) purifying the concentrated second washed solution by column chromatography; and (n) recrystallizing the purified second washed solution in hexanes/diethyl ether to form the desired (cyanophenyl)benzofuran carbonitrile (151, 152), (methyl-oxycarbonylphenyl) benzofuran carboxylate (155, 156), or ((cyanophenyl)methoxy)benzofurancarbaldehyde (160).

(ii) Process for the Synthesis of (cyanophenyl)benzofuran carbonitriles (157, 158)

Referring again to Scheme 6, (cyanophenyl)benzofuran carbonitriles (157, 158) are synthesize from the appropriate (methyl-oxycarbonylphenyl)benzofuran carboxylates (155, 156) by: (a) bubbling anhydrous $NH_3$ through dry o-xylene for 20 min at 0° C. to form a first reaction mixture; (b) adding a 2.0 M solution of $AlMe_3$ in toluene to the first reaction mixture to form a second reaction mixture; (c) passing $NH_3$ through the second reaction mixture for 20 min to form a third reaction mixture; (d) stirring the third reaction mixture at room temperature for one hr; (e) adding the appropriate (methyl-oxycarbonylphenyl)benzofuran carboxylate (155, 156) to the third reaction mixture to form a fourth reaction mixture; (f) allowing the fourth reaction mixture to cool to room temperature; (g) diluting the fourth reaction mixture with $CHCl_3$ to form a diluted fourth reaction mixture; (h) adding water dropwise to the diluted fourth reaction mixture with vigorous stirring to form a fifth reaction mixture; (i) filtering off inorganic solids from the fifth reaction mixture to form an organic filtrate; (j) separating and concentrating the organic filtrate to form a residue; and (k) purifying the residue by column chromatography to form the desired (cyanophenyl)benzofuran carbonitrile (157, 158).

(iii) Process for the Synthesis of ((cyanophenyl)methoxy) benzofuran carbonitrile (162)

Referring again to Scheme 6, the ((cyanophenyl)methoxy) benzofuran carbonitrile (162) is synthesized by: (a) adding the appropriate ((cyanophenyl)methoxy)benzofurancarbaldehyde (160) and hydroxylamine to a melted pyridine hydrochloride at 160-180° C. to form a first reaction mixture; (b) stirring the first reaction mixture at 180° C. for 3 hr; (c) cooling the first reaction mixture; (d) diluting the first reaction mixture with water and 1 M HCl to form a diluted first reaction mixture; (e) stirring the diluted first reaction mixture for 30 min to form a precipitate; (f) separating the precipitate; (g) washing the precipitate with 1 M HCl and water; (h) drying the washed precipitate to form a residue; (i) purifying the residue by flash chromatography to form a purified residue; and (j) recrystallizing the purified residue to form the appropriate formaldehyde oxime (161). The formaldehyde oxime (161) is then added to a solution of $AC_2O$ and refluxed overnight to form the ((cyanophenyl)methoxy)benzofuran carbonitrile (162).

(iv) Process for the Synthesis of 2-aryl Benzofuran-Containing Dications (163-177) of Formula (II)

Referring again to Scheme 6, 2-aryl benzofuran-containing dications (163-177) of Formula (II) are synthesized from the appropriate (cyanophenyl)benzofuran carbonitrile (151, 152, 157, 158, 162) by: (a) mixing dry 1,4-dioxane and dry ethanol to form a first reaction mixture; (b) saturating the first reaction mixture with anhydrous gaseous HCl to form a second reaction mixture; (c) adding the appropriate (cyanophenyl)benzofuran carbonitrile (151, 152, 157, 158, 162) to the second reaction mixture to form a third reaction mixture; (d) diluting the third reaction mixture with dry ether to form a diimidate; (e) collecting the diimidate under an inert gas; (f) washing the diimidate with diethyl ether; (g) drying the diimidate; (h) suspending the diimidate in dry ethanol to form a fourth reaction mixture; (i) saturating the fourth reaction mixture with the appropriate amine to form a fifth reaction mixture; (j) diluting the fifth reaction mixture with diethyl ether; (k) cooling the diluted reaction mixture to form a precipitate; (l) collecting the precipitate; (m) washing the precipitate with diethyl ether; (n) drying the precipitate; and (o) recrystallizing the precipitate from aqueous HCl to form the dihydrochloride salt of the desired 2-aryl benzofuran-containing dication (163-177) of Formula (II).

E. General Process for the Synthesis of Bis-Amidoximes (178, 180, 182, 183, 184-186) of Formulae (I-III)

Referring now to Scheme 7, bis-amidoximes (178, 180, 182, 183, 184-186) are synthesized from the appropriate benzofuran carbodinitrile by: (a) adding potassium tert-butoxide to a solution of $NH_2OH$ HCl in dry DMSO to form a first reaction mixture; (b) stirring the first reaction mixture for a period of time; (c) adding the appropriate benzofuran carbodinitrile to the first reaction mixture to form a second reaction mixture; (d) stirring the second reaction mixture at room temperature for four days; (e) pouring the second reaction mixture into ice water and stirring for one hr to form a precipitate; (f) filtering the precipitate; (g) washing the precipitate with water and ethanol; (h) drying the washed precipitate; and (i) recrystallizing the washed precipitate from DMF- EtOH-aq HCl mixture to form the desired bis-amidoxime (178, 180, 182, 183, 184-186).

G. General Process for the Synthesis of Bis-Methylamidoximes (179, 181, 187-189) of Formulae (I-III)

Referring again to Scheme 7, bis-mehtylamidoximes (179, 181, 187-189) are synthesized from the appropriate benzofuran carboxamidine by: (a) adding an aqueous NaOH solution to a stirred solution of the appropriate benzofuran carboxamidine in DMSO to form a first reaction mixture; (b) cooling the first reaction mixture; (c) adding dimethyl sulfate to the cooled first reaction mixture to form a second reaction mixture; (d) stirring the second reaction mixture at 0° C. for four hrs and then overnight at room temperature; (e) diluting the second reaction mixture with water to form a residue; (f) separating the residue; (g) purifying the residue by column chromatography; and (h) recrystallizing the residue from aqueous HCl to form the desired bis-methylamidoxime (179, 181, 187-189).

H. Process for the Synthesis of Bis-Amidoximes (190) and Bis-Methylamidoximes (191, 193) of Formula (III) via the Pinner Procedure Referring again to Scheme 7, bis-amidoximes (190) and bis-methylamidoximes (191, 193) are synthesized from the appropriate benzofuran carbodinitrile (103, 115) by: (a) saturating a mixture of freshly distilled ethanol and 1,4-dioxane with anhydrous HCl gas at 0° C. to form a first reaction mixture; (b) adding the appropriate benzofuran carbodinitrile (103, 115) to the first reaction mixture to form a second reaction mixture; (c) stirring the second reaction mixture at room temperature for two days; (d) diluting the stirred second reaction mixture with anhydrous diethyl ether to form a diluted second reaction mixture; (e) placing the diluted second reaction mixture in a freezer for three hrs to form an imidate precipitate; (f) filtering the imidate precipitate to form an imidate residue; (g) drying the imidate residue; and (h) separating the dried imidate residue into two parts.

The bis-amidoxime (190) and bis-methylamidoximes (191, 193) are synthesized from the imidate residue by reacting the imidate residue with hydroxylamine and methylhydroxylamine immediately by: (a) dissolving the appropriate hydroxylamine hydrochloride in a solution of NaOMe in MeOH to form a first reaction mixture; (b) adding the crude imidate to the first reaction mixture to form a second reaction mixture; (c) stirring the second reaction mixture at room temperature for two days to form a reaction product; (d) purifying the reaction product with prep-HPLC; and (e) converting the purified reaction product into the HCl salt with aqueous HCl to form the salts of the desired bis-amidoxime (190) and bis-methylamidoxime (191, 193).

IV. Novel Compounds

A. Compounds of Formula (I)

Described herein is a compound of Formula (I):

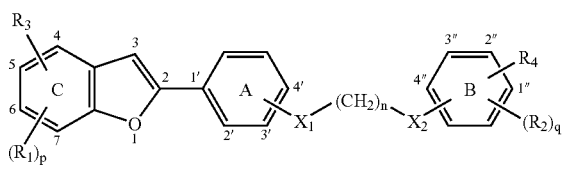

(I)

wherein:
n is an integer from 1 to 8;
p and q are integers from 0 to 3;
$X_1$ and $X_2$ are each independently selected from the group consisting of O, S, and $NR_5$, wherein $R_5$ is selected from the group consisting of H, alkyl, aryl, alkoxyl, and aryloxyl;
$R_1$ and $R_2$ are each independently selected from the group consisting of alkyl, halo, hydroxyl, alkoxyl, aryloxyl, and aralkyloxyl; and
$R_3$ and $R_4$ are each independently selected from the group consisting of:

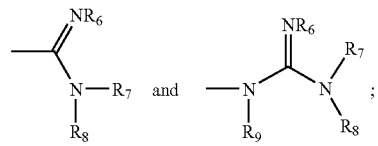

wherein:
$R_6$, $R_7$, $R_8$, and $R_9$ are each independently selected from the group consisting of H, alkyl, cycloalkyl, aryl, aralkyl, hydroxyl, alkoxyl, hydroxyalkyl, hydroxycycloalkyl, alkoxycycloalkyl, aminoalkyl, acyloxyl, alkylaminoalkyl, and alkoxycarbonyl; or
$R_6$ and $R_7$ together represent a $C_2$ to $C_{10}$ alkyl, $C_2$ to $C_{10}$ hydroxyalkyl, or $C_2$ to $C_{10}$ alkylene.

B. Compounds of Formula (II)

Described herein is a compound of Formula (II):

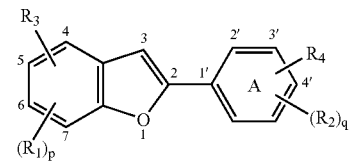

(II)

wherein:
p and q are integers from 0 to 3;
$R_1$ and $R_2$ are each independently selected from the group consisting of alkyl, halo, hydroxyl, alkoxyl, aryloxyl, and aralkyloxyl; and
$R_3$ and $R_4$ are each independently selected from the group consisting of:

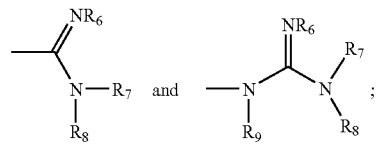

wherein:
$R_6$, $R_7$, $R_8$, $R_9$ are each independently selected from the group consisting of H, alkyl, cycloalkyl, aryl, aralkyl, hydroxyl, alkoxyl, hydroxyalkyl, hydroxycycloalkyl, alkoxycycloalkyl; aminoalkyl, acyloxyl, alkylaminoalkyl, and alkoxycarbonyl; or
$R_6$ and $R_7$ together represent a $C_2$ to $C_{10}$ alkyl, $C_2$ to $C_{10}$ hydroxyalkyl, or $C_2$ to $C_{10}$ alkylene.

C. Compounds of Formula (III)

Described herein is a compound of Formula (III):

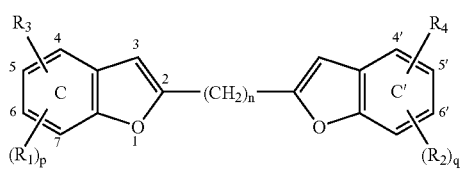

wherein:
n is an integer from 1 to 8;
p and q are integers from 0 to 3;
$R_1$ and $R_2$ are each independently selected from the group consisting of alkyl, halo, hydroxyl, alkoxyl, aryloxyl, and aralkyloxyl; and
$R_3$ and $R_4$ are each independently selected from the group consisting of:

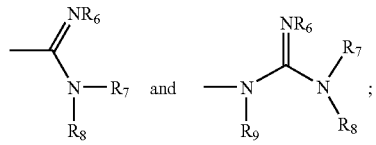

wherein:
$R_6$, $R_7$, $R_8$, and $R_9$ are each independently selected from the group consisting of H, alkyl, cycloalkyl, aryl, aralkyl, hydroxyl, alkoxyl, hydroxyalkyl, hydroxycycloalkyl, alkoxycycloalkyl, aminoalkyl, acyloxyl, alkylaminoalkyl, and alkoxycarbonyl; or
$R_6$ and $R_7$ together represent a $C_2$ to $C_{10}$ alkyl, $C_2$ to $C_{10}$ hydroxyalkyl, or $C_2$ to $C_{10}$ alkylene.

D. Prodrugs

In representative embodiments, compounds disclosed herein are prodrugs. A produrg means a compound that, upon administration to a recipient, is capable of providing (directly or indirectly) a compound of this presently disclosed subject matter or an inhibitorily active metabolite or residue thereof. Prodrugs can increase the bioavailability of the compounds of this presently disclosed subject matter when such compounds are administered to a subject (e.g., by allowing an orally administered compound to be more readily absorbed into the blood) or can enhance delivery of the parent compound to a biological compartment (e.g., the brain or lymphatic system) relative to a metabolite species, for example. A number of the compounds (e.g., Compounds 178-193) provided in the Examples are prodrugs.

E. Pharmaceutically Acceptable Salts

Additionally, the active compounds can be administered as pharmaceutically acceptable salts. Such salts include the gluconate, lactate, acetate, tartarate, citrate, phosphate, borate, nitrate, sulfate, and hydrochloride salts. The salts of the compounds described herein can be prepared, in general, by reacting two equivalents of the base compound with the desired acid, in solution. After the reaction is complete, the salts are crystallized from solution by the addition of an appropriate amount of solvent in which the salt is insoluble. In a particular embodiment, the pharmaceutically acceptable salt is a hydrochloride salt.

V. Pharmaceutical Formulations

The compounds of Formulae (I), (II), and (III), the pharmaceutically acceptable salts thereof, prodrugs corresponding to compounds of Formulae (I), (II), and (III), and the pharmaceutically acceptable salts thereof, are all referred to herein as "active compounds." Pharmaceutical formulations comprising the aforementioned active compounds also are provided herein. These pharmaceutical formulations comprise active compounds as described herein, in a pharmaceutically acceptable carrier. Pharmaceutical formulations can be prepared for oral, intravenous, or aerosol administration as discussed in greater detail below. Also, the presently disclosed subject matter provides such active compounds that have been lyophilized and that can be reconstituted to form pharmaceutically acceptable formulations for administration, as by intravenous or intramuscular injection.

The therapeutically effective dosage of any specific active compound, the use of which is within the scope of embodiments described herein, will vary somewhat from compound to compound, and patient to patient, and will depend upon the condition of the patient and the route of delivery. As a general proposition, a dosage from about 0.1 to about 50 mg/kg will have therapeutic efficacy, with all weights being calculated based upon the weight of the active compound, including the cases where a salt is employed. Toxicity concerns at the higher level can restrict intravenous dosages to a lower level such as up to about 10 mg/kg, with all weights being calculated based upon the weight of the active base, including the cases where a salt is employed. A dosage from about 10 mg/kg to about 50 mg/kg can be employed for oral administration. Typically, a dosage from about 0.5 mg/kg to 5 mg/kg can be employed for intramuscular injection. In some embodiments, dosages are 1 μmol/kg to 50 μmol/kg. In some embodiments, dosages are 22 μmol/kg and 33 μmol/kg of the compound for intravenous or oral administration. The duration of the treatment is usually once per day for a period of two to three weeks or until the condition is essentially controlled. Lower doses given less frequently can be used prophylactically to prevent or reduce the incidence of recurrence of the infection.

In accordance with the present methods, pharmaceutically active compounds as described herein can be administered orally are a solid or a liquid, or can be administered intramuscularly or intravenously as a solution, suspension, or emulsion. Alternatively, the compounds or salts can also be administered by inhalation, intravenously or intramuscularly as a liposomal suspension. When administered through inhalation the active compound or slat should be in the form of a plurality of solid particles or droplets having a particle size from about 0.5 to about 5 microns, and preferably from about 1 to about 2 microns.

Pharmaceutical formulations suitable for intravenous or intramuscular injection are further embodiments provided herein. The pharmaceutical formulations comprise a compound of Formulae (I), (II), and (III) described herein, a prodrug as described herein, or a pharmaceutically acceptable salt thereof, in any pharmaceutically acceptable carrier. If a solution is desired, water is the carrier of choice with respect to water-soluble compounds or salts. With respect to the water-soluble compounds or salts, an organic vehicle, such as glycerol, propylene glycol, polyethylene glycol, or mixtures thereof, can be suitable. In the latter instance, the organic vehicle can contain a substantial amount of water. The solution is either instance can then be sterilized in a suitable manner known to those in the art, and typically by filtration through a 0.22-micron filter. Subsequent to sterilization, the solution can be dispensed into appropriate receptacles, such as depyrogenated glass vials. Of course, the dispensing is preferably done by an aseptic method. Sterilized closures can then be placed on the vials and, if desired, the vial contents can be lyophilized.

In addition to compounds of Formulae (I), (II), and (III) or their salts or prodrugs, the pharmaceutical formulations can contain other additives, such as pH-adjusting additives. In particular, useful pH-adjusting agents include acids, such as hydrochloric acid, bases or buffers, such as sodium lactate, sodium acetate, sodium phosphate, sodium citrate, sodium borate, or sodium gluconate. Further, the formulations can contain anti-microbial preservatives. Useful anti-microbial preservatives include methylparaben, proplyparaben, and benzyl alcohol. The anti-microbial preservative is typically employed when the formulation is placed in a vial designed for multi-dose use. The pharmaceutical formulations described herein can be lyophilized using techniques well known in the art.

In yet another aspect of the subject matter described herein, there is provided an injectable, stable, sterile formulation comprising a compound of Formulae (I), (II), and (III), or a salt thereof, in a unit dosage form in a sealed container. The compound or salt is provided in the form of a lyophilizate, which is capable of being reconstituted with a suitable pharmaceutically acceptable carrier to form a liquid formulation suitable for injection thereof into the subject. The unit dosage form typically comprises from about 10 mg to about 10 grams of the compound salt. When the compound or salt is substantially water-insoluble, a sufficient amount of emulsifying agent, which is physiologically acceptable, can be employed in sufficient quantity to emulsify the compound or salt in an aqueous carrier. One such useful emulsifying agent is phosphatidyl choline.

Other pharmaceutical formulations can be prepared from the water-insoluble compounds disclosed herein, or salts thereof, such as aqueous base emulsions. In such an instance, the formulation will contain a sufficient amount of pharmaceutically acceptable emulsifying agent to emulsify the desired amount of the compound or salt thereof. Particularly useful emulsifying agents include phosphatidyl cholines, and lecithin.

Additional embodiments provided herein include liposomal formulations of the active compounds disclosed herein. The technology for forming liposomal suspensions is well known in the art. When the compound is an aqueous-soluble salt, using conventional liposome technology, the same can be incorporated into lipid vesicles. In such an instance, due to the water solubility of the active compound, the active compound will be substantially entrained within the hydrophilic center or core of the liposomes. The lipid layer employed can be of any conventional composition and can either contain cholesterol or can be cholesterol-free. When the active compound of interest is water-insoluble, again employing conventional liposome formation technology, the salt can be substantially entrained within the hydrophobic lipid bilayer that forms the structure of the liposomes. In either instance, the liposomes that are produced can be reduced in size, as through the use of standard sonication and homogenization techniques.

The liposomal formulations containing the active compounds disclosed herein can be lyophilized to produce a lyophilizate, which can be reconstituted with a pharmaceutically acceptable carrier, such as water, to regenerate a liposomal suspension.

Pharmaceutical formulations also are provided which are suitable for administration as an aerosol, by inhalation. These formulations comprise a solution or suspension of a desired compound described herein or a salt thereof, or a plurality of solid particles of the compound or salt. The desired formulation can be placed in a small chamber and nebulized. Nebulizaton can be accomplished by compressed air or by ultrasonic energy to form a plurality of liquid droplets or solid particles comprising the compounds or salts. The liquid droplets or solid particles should have a particle size in the range of about 0.5 to about 10 microns, more preferably from about 0.5 to about 5 microns. The solid particles can be obtained by processing the solid compound or a salt thereof, in any appropriate manner known in the art, such as by micronization. Most preferably, the size of the solid particles or droplets will be from about 1 to about 2 microns. In this respect, commercial nebulizers are available to achieve this purpose. The compounds can be administered via an aerosol suspension of respirable particles in a manner set forth in U.S. Pat. No. 5,628,964, the disclosure of which is incorporated herein by reference in its entirety.

When the pharmaceutical formulation suitable for administration as an aerosol is in the form of a liquid, the formulation will comprise a water-soluble active compound in a carrier that comprises water. A surfactant can be present, which lowers the surface tension of the formulation sufficiently to result in the formation of droplets within the desired size range when subjected to nebulization.

As indicated, both water-soluble and water-insoluble active compounds are provided. As used in the present specification, the term "water-soluble" is meant to define any composition that is soluble in water in an amount of about 50 mg/mL, or greater. Also, as used in the present specification, the term "water-insoluble" is meant to define any composition that has solubility in water of less than about 20 mg/mL. For certain applications, water-soluble compounds or salts can be desirable whereas for other applications water-insoluble compounds or salts likewise can be desirable.

EXAMPLES

The following Examples have been included to illustrate modes of the presently disclosed subject matter. Certain aspects of the following Examples are described in terms of techniques and procedures found or contemplated to work well in the practice of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter.

Methods and Materials For Examples 1-8

All commercial chemicals and solvents are reagent grade and were used without further purification unless otherwise stated. Anhydrous ethanol was distilled over Mg immediately prior to use. Reactions were monitored by TLC on 0.25 mm silica gel plates (Whatman $UV_{254}$ silica) or by analytical reverse phase HPLC using a Hewlett-Packard Series 1090, equipped with a Zorbax SB C8 4.6×75 mm 3.5 micron column as a stationary phase. A binary solvent system where phase A consisted to formic acid (80 mM), ammonium formate (20 mM) and triethylamine 15 (mM) in 100% of water and phase B consisted of formic acid (80 mM), ammonium formate (20 mM) and triethylamine (15 mM) in 75% acetonitrile and 25% of water was used. The programs employed ran as follows. Method A: linear gradient 0-30% solvent B in 6 min, then 30-75% of solvent B in 10 min, 4 min, hold for 1 min. Method B: linear gradient 30-75% solvent B in 10 min, hold for 2 min. The flow rate was maintained at 1.5 mL/min. Column and flash chromatography was carried out using Fisher Davisil® 60A (200-425 mesh). Melting points were determined on a Thomas Hoover (Uni-Melt) capillary melting point apparatus and are uncorrected. $^1$H NMR spectra were recorded on a Varian Gemini2000 NMR spectrometer (300 MHz) and are reported in ppm (δ) relative to tetramethylsilane (TMS) as an internal standard. Unless otherwise stated, DMSO-$d_6$ was used as solvent and the following abbreviations are used: singlet (s), dublet (d), dublet dublet (dd), triplet (t), multiplet (m), broad (br). Coupling constants (J values) are given in hertz (Hz). Elemental analyses were obtained from Atlantic Microlab Inc. (Norcross, Ga.) and are within 0.4% of the theoretical values unless otherwise noted. Low-resolution mass spectra were obtained on Aligent 1100 MS using electrospray ionization. The compound was determined to be "consistent" with the chemical formula if the mass measurement was within 0.5 pm relative M+H of exact monoisotopic mass.

The purity of isolated final compounds (1-79) was greater then 95% on analytical reverse phase HPLC and was achieved by recrystallization from 1.5 M aqueous HCl/EtOH mixtures. When necessary, preparative reverse phase HPLC was performed on an automated Varian ProStar Chromatography Workstation, equipped with PS-701 fraction collector, solvent pumps PS-215, head size 50 mL, UV-VIS ProStar 320 Detector (λ=254 nm) and Dynamax®-60A° (41×250 mm) preparative column. The eluents employed were phase A: formic acid (40 mM) and ammonium formate (10 mM) in 100% of water and phase B: formic acid (40 mM), ammonium formate (10 mM) in 75% acetonitrile and 25% of water. The program ran as follows. Method C: linear gradient 0-100% solvent B in 35 min, hold for 5 min. The flow rate was held constant at 40 mL/min. The purified fractions were evaporated to dryness. The residue was dissolved in water, the solution was frozen at −78° C. and lyophilized twice on VirTisBenchTop 2K lyophilizer at −52° C. and 45-70 millitorr. Acquired bis-amidines, as free bases, were dissolved in ethanol and converted into their HCl salts with 3 M aqueous HCl.

All chemicals and solvents were purchased from Aldrich chemical Co., Fisher Scientific, or Acros organics.

Example 1

Scheme 1

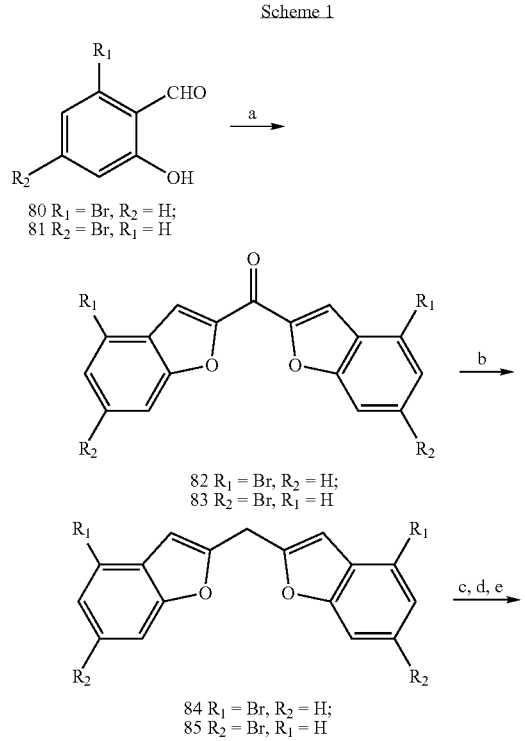

Example 2

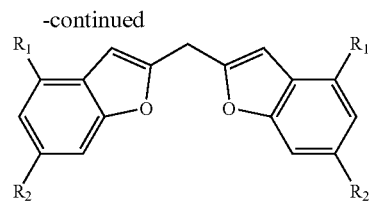

1 $R_1$ = Am, $R_2$ = H;
86 $R_1$ = CN, $R_2$ = H ⟶ 2 $R_1$ = i-PrAm, $R_2$ = H;
3 $R_1$ = im, $R_2$ = H

87 $R_2$ = CN, $R_1$ = H ⟶ 7 $R_2$ = im, $R_1$ = H

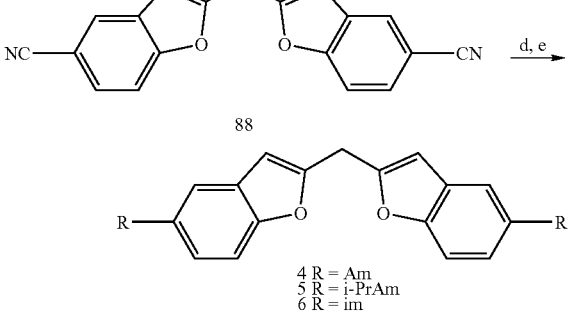

4 R = Am
5 R = i-PrAm
6 R = im

Reagents and conditions for Scheme 1: (a) 1,3-Dichloroacetone, $K_2CO_3$, 2-butanone, reflux, 4 h; (b) $AlCl_3$, $LiAlH_4$, EtOEt, rt, 1 h, then 2N HCl; (c) CuCN, quinoline, reflux, 3 h; (d) 1,4-dioxane, EtOH, HCl, 1-3 days; (e) appropriate amine, EtOH, 1-4 days.

Scheme 2

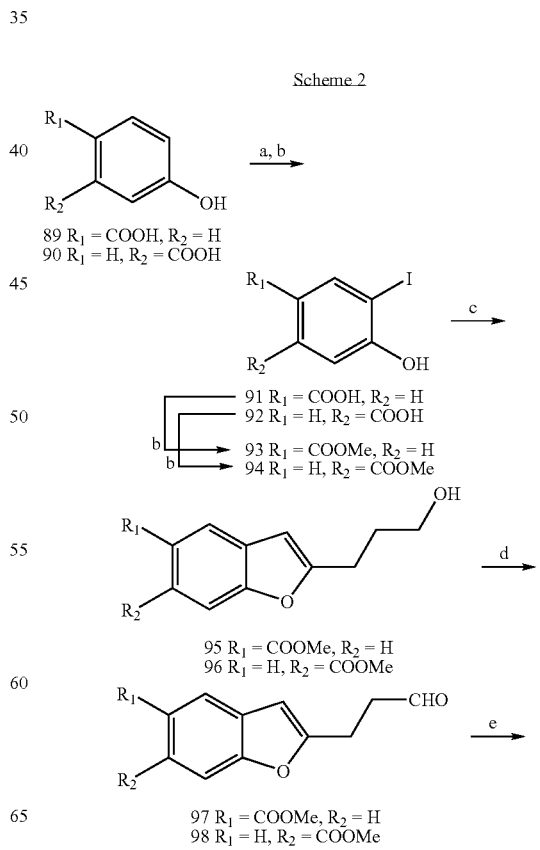

-continued

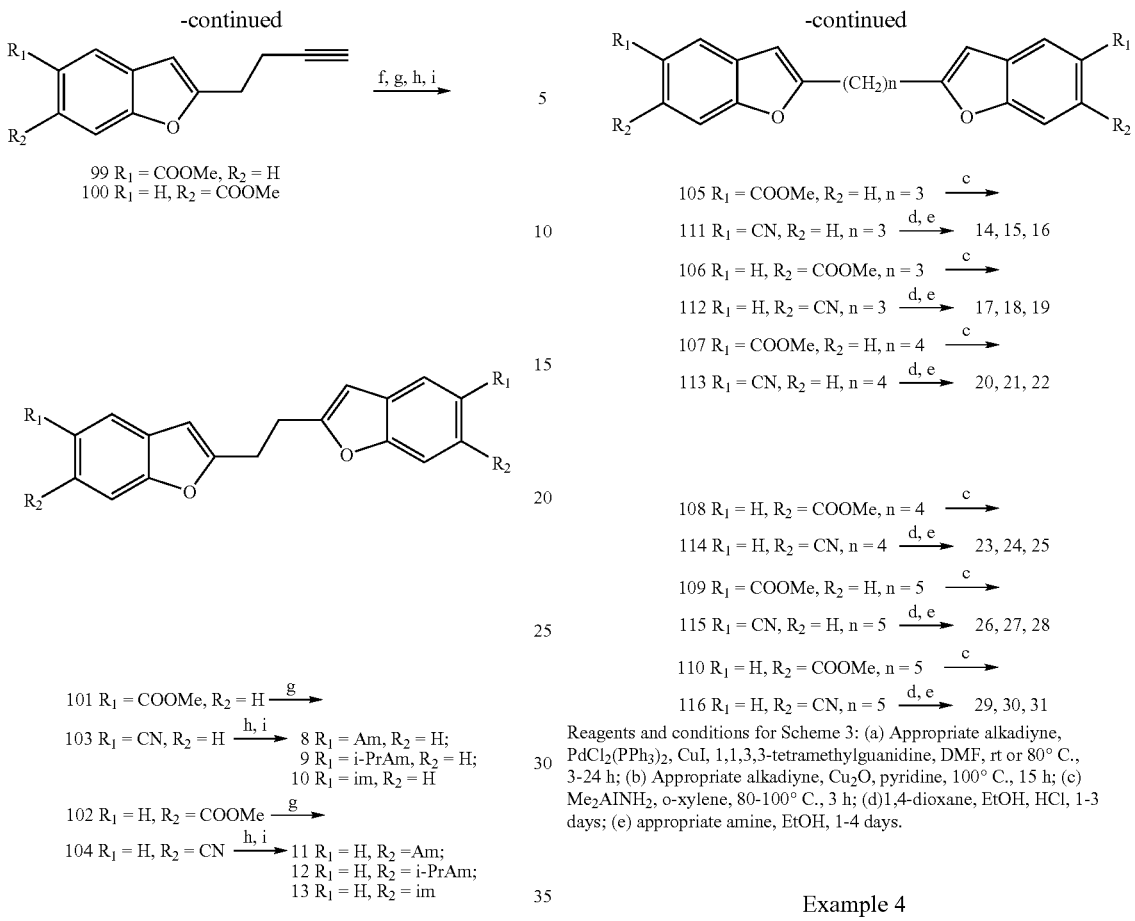

99 R₁ = COOMe, R₂ = H
100 R₁ = H, R₂ = COOMe

101 R₁ = COOMe, R₂ = H $\xrightarrow{g}$
103 R₁ = CN, R₂ = H $\xrightarrow{h, i}$ 8 R₁ = Am, R₂ = H;
9 R₁ = i-PrAm, R₂ = H;
10 R₁ = im, R₂ = H 102 R₁ = H, R₂ = COOMe $\xrightarrow{g}$
104 R₁ = H, R₂ = CN $\xrightarrow{h, i}$ 11 R₁ = H, R₂ = Am;
12 R₁ = H, R₂ = i-PrAm;
13 R₁ = H, R₂ = im 105 R₁ = COOMe, R₂ = H, n = 3 $\xrightarrow{c}$
111 R₁ = CN, R₂ = H, n = 3 $\xrightarrow{d, e}$ 14, 15, 16
106 R₁ = H, R₂ = COOMe, n = 3 $\xrightarrow{c}$
112 R₁ = H, R₂ = CN, n = 3 $\xrightarrow{d, e}$ 17, 18, 19
107 R₁ = COOMe, R₂ = H, n = 4 $\xrightarrow{c}$
113 R₁ = CN, R₂ = H, n = 4 $\xrightarrow{d, e}$ 20, 21, 22
108 R₁ = H, R₂ = COOMe, n = 4 $\xrightarrow{c}$
114 R₁ = H, R₂ = CN, n = 4 $\xrightarrow{d, e}$ 23, 24, 25
109 R₁ = COOMe, R₂ = H, n = 5 $\xrightarrow{c}$
115 R₁ = CN, R₂ = H, n = 5 $\xrightarrow{d, e}$ 26, 27, 28
110 R₁ = H, R₂ = COOMe, n = 5 $\xrightarrow{c}$
116 R₁ = H, R₂ = CN, n = 5 $\xrightarrow{d, e}$ 29, 30, 31

Reagents and conditions for Scheme 3: (a) Appropriate alkadiyne, PdCl₂(PPh₃)₂, CuI, 1,1,3,3-tetramethylguanidine, DMF, rt or 80° C., 3-24 h; (b) Appropriate alkadiyne, Cu₂O, pyridine, 100° C., 15 h; (c) Me₂AlNH₂, o-xylene, 80-100° C., 3 h; (d) 1,4-dioxane, EtOH, HCl, 1-3 days; (e) appropriate amine, EtOH, 1-4 days.

Reagents and conditions for Scheme 2: (a) NaI, NaOH, MeOH, NaOCl aq (4%), then Na₂S₂O₃ aq (10%); (b) H₂SO₄, MeOH; (c) 4-Pentyn-1-ol, Cu₂O, pyridine, 100° C., 15 h; (d) 2 M Oxalyl chloride in CH₂Cl₂, DMSO, CH₂Cl₂, -70° C., 1 h, then NEt₃; (e) Dimethyl-1-diazo-2-oxopropylphosphonate, K₂CO₃, MeOH; (f) 93 or 94, Cu₂O, pyridine, 100° C., 15 h; (g) Me₂AlNH₂, o-xylene, 80-100° C., 3 h; (h) 1,4-dioxane, EtOH, HCl, 1-3 days; (i) appropriate amine, EtOH, 1-4 days.

Example 3

Scheme 3

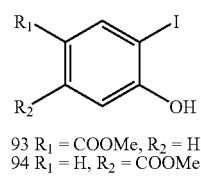

93 R₁ = COOMe, R₂ = H
94 R₁ = H, R₂ = COOMe

Example 4

Scheme 4

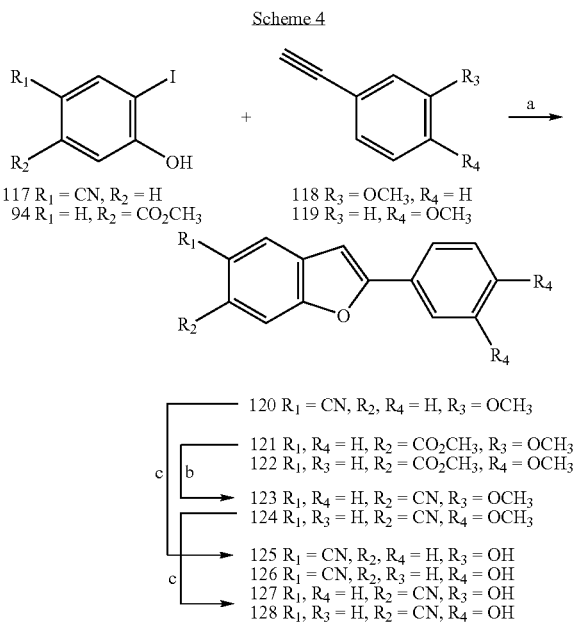

117 R₁ = CN, R₂ = H
94 R₁ = H, R₂ = CO₂CH₃

118 R₃ = OCH₃, R₄ = H
119 R₃ = H, R₄ = OCH₃

120 R₁ = CN, R₂ = R₄ = H, R₃ = OCH₃
121 R₁, R₄ = H, R₂ = CO₂CH₃, R₃ = OCH₃
122 R₁, R₃ = H, R₂ = CO₂CH₃, R₄ = OCH₃
123 R₁, R₄ = H, R₂ = CN, R₃ = OCH₃
124 R₁, R₃ = H, R₂ = CN, R₄ = OCH₃
125 R₁ = CN, R₂, R₄ = H, R₃ = OH
126 R₁ = CN, R₂, R₃ = H, R₄ = OH
127 R₁, R₄ = H, R₂ = CN, R₃ = OH
128 R₁, R₃ = H, R₂ = CN, R₄ = OH

Reagents and conditions for Scheme 4: (a) Cu₂O, pyridine, 100° C., overnight; (b) Me₂AlNH₂, o-xylene, 110-120° C., 3 h; (c) PyxHCl, 170-180° C., 3 h.

Example 5
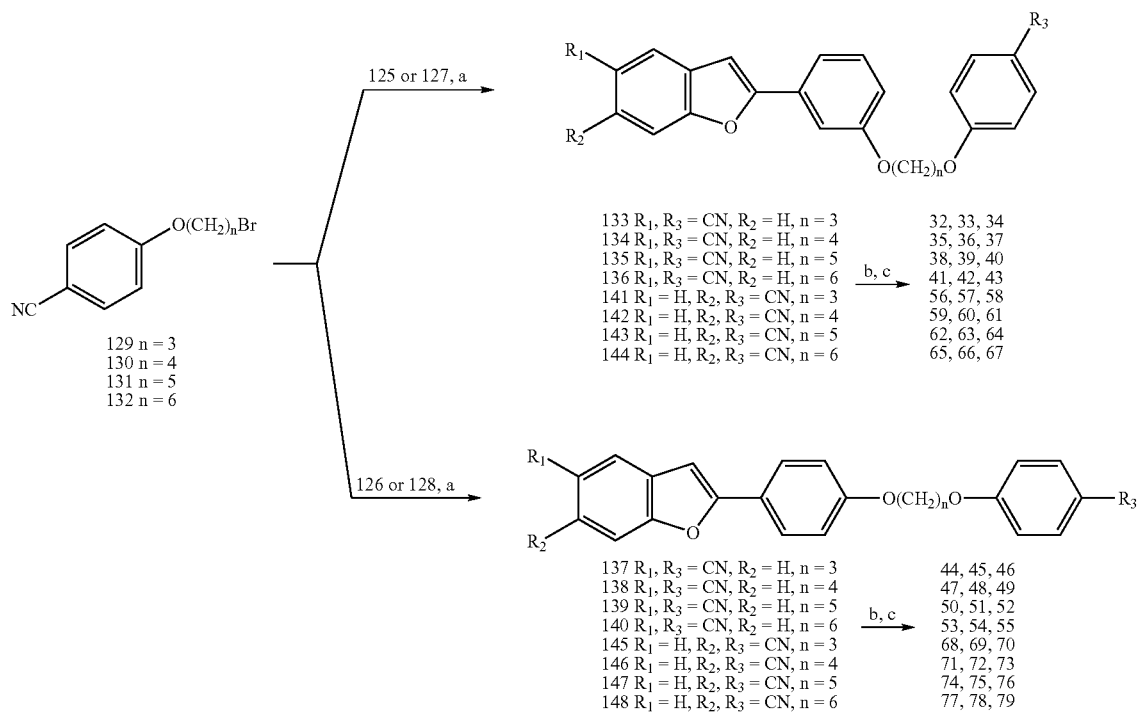
Reagents and conditions for Scheme 5: (a) 125-128, K$_2$CO$_3$, DMF, 80° C., overnight; (b) 1,4-dioxane, EtOH, HCl(gas); (c) appropriate amine, EtOH.
Example 6
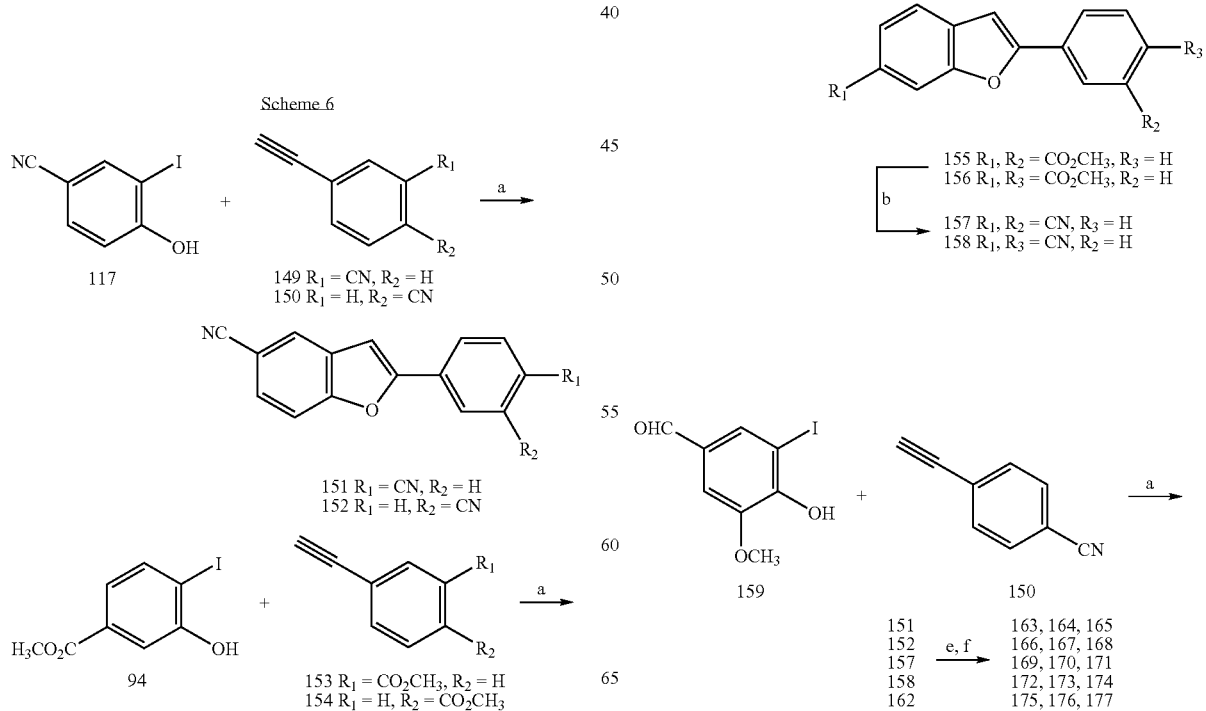

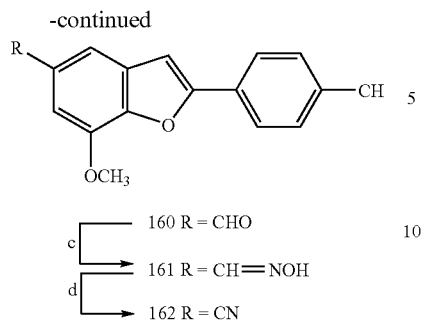

160 R = CHO
c ↓
161 R = CH=NOH
d ↓
162 R = CN

Reagents and conditions for Scheme 6: (a) Cu₂O, pyridine, 100° C., overnight; (b) Me₂AlNH₂, o-xylene, 110-120° C., 3 h; (c) NH₂OH×HCl, pyridine, 3 h; (d) Ac₂O, reflux, overnight; (e) 1,4-dioxane, EtOH, HCl(gas); (f) appropriate amine, EtOH.

Example 7

Scheme 7

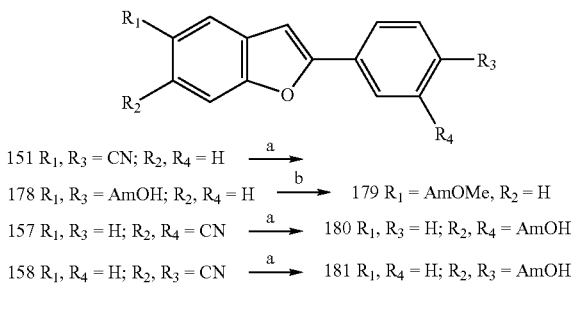

151 R₁, R₃ = CN; R₂, R₄ = H  —a→
178 R₁, R₃ = AmOH; R₂, R₄ = H  —b→  179 R₁ = AmOMe, R₂ = H
157 R₁, R₃ = H; R₂, R₄ = CN  —a→  180 R₁, R₃ = H; R₂, R₄ = AmOH
158 R₁, R₄ = H; R₂, R₃ = CN  —a→  181 R₁, R₄ = H; R₂, R₃ = AmOH

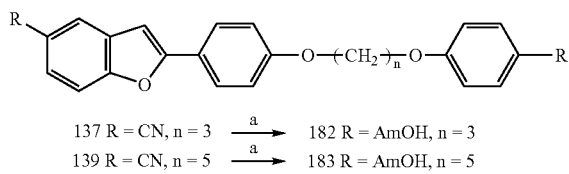

137 R = CN, n = 3  —a→  182 R = AmOH, n = 3
139 R = CN, n = 5  —a→  183 R = AmOH, n = 5

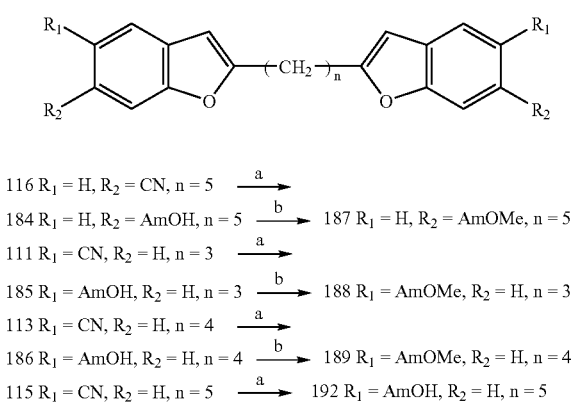

116 R₁ = H, R₂ = CN, n = 5  —a→
184 R₁ = H, R₂ = AmOH, n = 5  —b→  187 R₁ = H, R₂ = AmOMe, n = 5
111 R₁ = CN, R₂ = H, n = 3  —a→
185 R₁ = AmOH, R₂ = H, n = 3  —b→  188 R₁ = AmOMe, R₂ = H, n = 3
113 R₁ = CN, R₂ = H, n = 4  —a→
186 R₁ = AmOH, R₂ = H, n = 4  —b→  189 R₁ = AmOMe, R₂ = H, n = 4
115 R₁ = CN, R₂ = H, n = 5  —a→  192 R₁ = AmOH, R₂ = H, n = 5

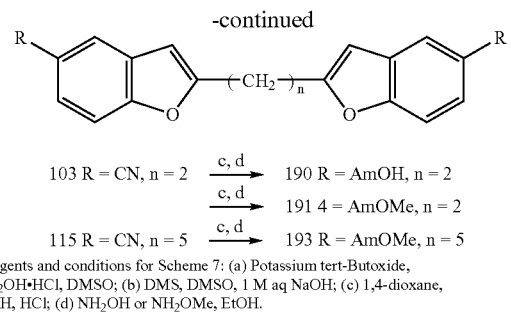

103 R = CN, n = 2  —c,d→  190 R = AmOH, n = 2
                          191 4 = AmOMe, n = 2
115 R = CN, n = 5  —c,d→  193 R = AmOMe, n = 5

Reagents and conditions for Scheme 7: (a) Potassium tert-Butoxide, NH₂OH·HCl, DMSO; (b) DMS, DMSO, 1 M aq NaOH; (c) 1,4-dioxane, EtOH, HCl; (d) NH₂OH or NH₂OMe, EtOH.

General Procedure for Syntheses of Bisamidines (1-79)

2-((4-Amidinobenzofuran-2-yl)methyl)benzofuran-4-carboxamidine dihydrochloride (1). Representative procedure. A mixture of dry 1,4-dioxane (40 mL) and dry EtOH (10 mL) in a 3-neck 250 mL flask equipped with a gas inlet tube, a thermometer, and a drying tube, was saturated with gaseous HCl at 0° C. 2-((4-Cyanobenzofuran-2-yl)methyl)benzofuran-4-carbonitrile (86) (1.42 g, 4.8 mmol) was added in one portion, the flask was sealed, and the mixture was stirred at room temperature until the starting material was no longer detectable by HPLC (1 day). The reaction mixture was diluted with dry ether and the diimidate was filtered off under argon, washed with diethyl ether and dried under high vacuum to give 2.11 g (96%), which was reacted immediately with appropriate amines.

The diimidate (0.70 g, 1.5 mmol) was suspended in dry EtOH saturated with gaseous ammonia (19 mL). The sealed reaction mixture was stirred at room temperature. The progress of the reaction was monitored by HPLC. After 4 days the reaction mixture was diluted with diethyl ether (50 mL) and placed in a freezer overnight. The resulting precipitate was collected by vacuum filtration, washed with diethyl ether and dried under high vacuum to give 0.45 g (89%) of crude material, which was recrystallized from 1.5 M HCl to afford 1, as a brown solid (0.14 g, 21%): mp 310-311° C. $^1$H NMR (DMSO-d₆) δ9.44 (s, 4H), 9.39 (s, 4H), 7.91 (d, J=8,2 Hz, 2H), 7.61 (d, J=7.7 Hz, 2H), 7.50 (dd, J=8.2, 7.7 Hz, 4H), 7.00 (s, 2H), 4.65 (s, 2H). HPLC (method A) $t_R$ 4.67 min (96.58 area %). Anal. ($C_{19}H_{16}N_4O_2$·2.2HCl·1.3H₂O) C, H, N, Cl.

2-((4-Amidinobenzofuran-2-yl)methyl)-N-isopropylbenzofuran-4-carboxamidine dihydrochloride (2). Brown solid (0.06 g, 8%): mp 210° C. (dec) (HCl/EtOH/diethyl ether (1/1)). $^1$H NMR (DMSO-d6) δ9.77 (d, J=8,6 Hz, 2H), 9.55 (s, 2H), 9.41 (s, 2H), 7.87 (d, J=7.7 Hz, 2H), 7.55 (d, J=7.1 Hz, 2H), 7.48 (dd, J=7.7, 7.1 Hz, 4H), 6.96 (s, 2H), 4.66 (s, 2H), 4.18 (h, J=6.0 Hz, 2H), 1.31 (d, J=6.0 Hz, 12H). M/Z 417.2 (MH$^+$ of free base). HPLC (method A) $t_R$ 6.29 min (96.37 area %). Anal. ($C_{25}H_{28}N_4O_2$·2HCl·1.5H₂O·0.5C₂H₅OH) C, H, N, Cl.

Bis(4-(4,5-dihydro-1H-imidazol-2-yl)benzofuran-2-yl)methane dihydrochloride (3). Light yellow solid (0.48 g, 69.9%): mp 333-335° C. (1.5 M HCl). $^1$H NMR (DMSO-d₆) δ10.69 (s, 4H), 7.98 (d, J=8,2 Hz, 2H), 7.79 (d, J=7.7 Hz, 2H), 7.52 (dd, J=8.2, 7.7 Hz, 4H), 7.25 (s, 2H), 4.67 (s, 2H), 4.04 (s, 8H). HPLC (method A) $t_R$ 4.67 min (98.19 area %). Anal. ($C_{23}H_{20}N_4O_2$·2HCl·0.5H₂O) C, H, N, Cl.

2-((5-Amidinobenzofuran-2-yl)methyl)benzofuran-5-carboxamidine dihydrochloride (4). See Dann, O.; Volz, G.; Demant, E.; Pfeifer, W.; Bergen, G.; Fick, H.; Walkenhorst, E.; Trypanocide Diamidine mit vier Ringen in einem oder zwei Ringsystemen. *Liebigs Ann. Chem.* 1973, 1112-1140. Yellow solid (0.18 g, 18.8%): mp 212-214° C. (lit. 201-206° C.). $^1$H NMR (DMSO-$d_6$) δ9.40 (s, 4H), 9.16 (s, 4H), 8.15 (d, J=1.6 Hz, 2H), 7.80 (d, J=8.8 Hz, 2H), 7.73 (dd, J=8.8, 1.6 Hz, 2H), 7.02 (s, 2H), 4.59 (s, 2H). HPLC (method A) $t_R$ 4.93 min (95.38 area %). Anal. ($C_{19}H_{16}N_4O_2 \cdot 2HCl \cdot 0.6H_2O$) C, H, N, Cl.

2-((5-Amidinobenzofuran-2-yl)methyl)-N-isopropylbenzofuran-5-carboxamidine dihydrochloride (5). White solid (0.75 g, 64.7%): mp 238-240° C. $^1$H NMR (DMSO-$d_6$) δ9.58 (d, J=7.8 Hz, 2H), 9.44 (s, 2H), 9.09 (s, 2H), 8.03 (d, J=1.6 Hz, 2H), 7.78 (d, J=8.8 Hz, 2H), 7.63 (dd, J=8.8, 1.6 Hz, 2H), 7.00 (s, 2H), 4.59 (s, 2H), 4.08 (h, J=6.0 Hz, 2H), 1.29 (d, J=6.0 Hz, 12H). HPLC (method B) $t_R$ 1.49 min (97.45 area %). Anal. ($C_{25}H_{28}N_4O_2 \cdot 2HCl \cdot 1.5H_2O$) C, H, N, Cl.

Bis(5-(4,5-dihydro-1H-imidazol-2-yl)benzofuran-2-yl) methane dihydrochloride (6). Light yellow solid (0.27 g, 25%): mp 233-235° C. $^1$H NMR (DMSO-$d_6$) δ10.80 (s, 4H), 8.38 (s, 2H), 7.96 (d, J=8.8 Hz, 2H), 7.85 (d, J=8.8 Hz, 2H), 7.06 (s, 2H), 4.60 (s, 2H), 4.01 (s, 8H). HPLC (method A) $t_R$ 5.83 min (99.63 area %). Anal. ($C_{23}H_{20}N_4O_2 \cdot 2HCl \cdot 1.1H_2O$) C, H, N, Cl.

Bis(6-(4,5-dihydro-1H-imidazol-2-yl)benzofuran-2-yl) methane dihydrochloride (7). Light brown solid (0.13 g, 50%): mp 341-343° C. $^1$H NMR (DMSO-$d_6$) δ10.82 (s, 4H), 8.40 (s, 2H), 7.96 (d, J=8.2 Hz, 2H), 7.88 (d, J=8.2 Hz, 2H), 7.03 (s, 2H), 4.66 (s, 2H), 4.01 (s, 8H). HPLC (method A) $t_R$ 5.83 min (100.00 area %). Anal. ($C_{23}H_{20}N_4O_2 \cdot 2HCl \cdot 2H_2O$) C, H, N, Cl.

2-(2-(5-Amidinobenzofuran-2-yl)ethyl)benzofuran-5-carboxamidine dihydrochloride (8). Yellow solid (0.17 g, 32%): mp 356° C. (dec). $^1$H NMR (DMSO-$d_6$) δ9.35 (s, 4H), 9.10 (s, 4H), 8.06 (s, 2H), 7.77 (d, J=8.8 Hz, 2H), 7.68 (d, J=8.8 Hz, 2H), 6.87 (s, 2H), 3.34 (s, 4H). HPLC (method A) $t_R$ 5.89 min (100.00 area %). Anal. ($C_{20}H_{18}N_4O_2 \cdot 2HCl \cdot 1.3H_2O$) C, H, N, Cl.

2-(2-(5-Amidinobenzofuran-2-yl)ethyl)-N-isopropylbenzofuran-5-carboxamidine dihydrochloride (9). White solid (0.18 g, 29%): mp 350° C. (dec) (1.5 M HCl). $^1$H NMR (DMSO-$d_6$) δ9.54 (d, J=8.0 Hz, 2H), 9.41 (s, 2H), 9.06 (s, 2H), 7.95 (d, J=1.6 Hz, 2H), 7.75 (d, J=8.8 Hz, 2H), 7.59 (dd, J=8.8, 1.6 Hz, 2H), 6.85 (s, 2H), 4.07 (h, J=6.0 Hz, 2H), 3.34 (s, 4H), 1.27 (d, J=6.0 Hz, 12H). HPLC (method A) $t_R$ 5.41 min (100.00 area %). Anal. ($C_{26}H_{30}N_4O_2 \cdot 2HCl$) C, H, N, Cl.

4,5-Dihydro-2-(2-(2-(5-(4,5-dihydro-1H-imidazol-2-yl) benzofuran-2-yl)ethyl)benzofuran-5-yl)-1H-imidazole dihydrochloride (10). Light beige solid (0.25 g, 42.1%): mp 366° C. (dec) (1.5 M HCl). $^1$H NMR (DMSO-$d_6$) δ10.68 (S, 4H), 8.29 (s, 2H), 7.90 (d, J=8.8 Hz, 2H), 7.82 (d, J=8.8 Hz, 2H), 6.94 (S, 2H), 4.04 (s, 8H), 3.34 (s, 4H). HPLC (method A) $t_R$ 4.69 min (100.00 area %). Anal. ($C_{24}H_{22}N_4O_2 \cdot 2HCl \cdot 1.7H_2O$) C, H, N, Cl.

2-(2-(6-Amidinobenzofuran-2-yl)ethyl)benzofuran-6-carboxamidine dihydrochloride (11). See Dann, O.; Char, H.; Grießmeier, H.; Synthesen biskationischer, trypanocider 1-Benzofuran-Verbindungen. *Liebigs Ann. Chem.* 1982, 1836-1869. Light yellow solid (0.12 g, 60%): mp 362° C. (dec) (1.5 M HCl). $^1$H NMR (DMSO-$d_6$) δ9.39 (s, 4H), 9.15 (s, 4H), 8.10 (d, J=1.1 Hz, 2H), 7.77 (d, J=8.2 Hz, 2H), 7.69 (dd, J=8.2, 1.1 Hz, 2H), 6.88 (s, 2H), 3.34 (s, 4H). HPLC (method A) $t_R$ 5.53 min (100.00 area %). Anal. ($C_{20}H_{18}N_4O_2 \cdot 2HCl \cdot H_2O$) C, H, N, Cl.

2-(2-(6-Amidinobenzofuran-2-yl)ethyl)-N-isopropylbenzofuran-6-carboxamidine dihydrochloride (12). Light yellow solid (0.13 g, 54.0%): mp 346° C. (dec) (1.5 M HCl). $^1$H NMR (DMSO-$d_6$) δ9.58 (d, J=8.2 Hz, 2H), 9.47 (s, 2H), 9.11 (s, 2H), 7.98 (s, 2H), 7.75 (d, J=8.2 Hz, 2H), 7.58 (d, J=8.2 Hz, 2H), 6.86 (s, 2H), 4.10 (h, J=6.6 Hz, 2H), 3.34 (s, 4H), 1.29 (d, J=6.6 Hz, 12H). HPLC (method A) $t_R$ 7.51 min (100.00 area %). Anal. ($C_{26}H_{30}N_4O_2 \cdot 2Cl \cdot 1.2H_2O$) C, H, N, Cl.

4,5-dihydro-2-(2-(2-(6-(4,5-dihydro-1H-imidazol-2-yl) benzofuran-2-yl)ethyl)benzofuran-6-yl)-1H-imidazole dihydrochloride (13). Yellow solid (0.21 g, 84%) (EtOH/DMSO/3 M HCl): mp >360° C. $^1$H NMR (DMSO-$d_6$/$D_2O$ (2/1)) δ8.14 (d, J=1.1 Hz, 2H), 7.82 (d, J=8.2 Hz, 2H), 7.75 (dd, J=8.2, 1.1 Hz, 2H), 4.02 (s, 8H), 3.38 (s, 4H). HPLC (method A) $t_R$ 7.51 min (96.89 area %). Anal. ($C_{24}H_{22}N_4O_2 \cdot 1.9HCl \cdot H_2O$) C, H, N, Cl.

2-(3-(5-Amidinobenzofuran-2-yl)proply)benzofuran-5-carboxamidine dihydrochloride (14). White solid (0.47 g, 71.2%): mp 168-170° C. (1.5 M HCl). $^1$H NMR (DMSO-$d_6$) δ9.34 (s, 4H), 9.06 (s, 4H), 8.08 (d, J=1.6 Hz, 2H), 7.87 (d, J=8.8 Hz, 2H), 7.69 (dd, 8.8, 1.6 Hz, 2H), 6.88 (s, 2H), 2.95 (t, J=7.1 Hz, 4H), 2.17 (p, J=7.1 Hz, 2H). HPLC (method B) $t_R$ 1.31 min (100.00 area %). Anal. ($C_{21}H_{20}N_4O_2 \cdot 2HCl \cdot H_2O$) C, H, N, Cl.

2-(3-(5-Amidinobenzofuran-2-yl)propyl)-N-isopropyl-benzofuran-5-carboxamidine dihydrochloride (15). White solid (0.42 g, 53%): mp 195-197° C. (1.5 M HCl). $^1$H NMR (DMSO-$d_6$) δ9.58 (d, J=7.9 Hz, 2H), 9.45 (s, 2H), 9.13 (s, 2H), 7.98 (s, 2H), 7.74 (d, J=8.8 Hz, 2H), 7.60 (d, 8.8 Hz, 2H), 6.86 (s, 2H), 4.10 (h, J=6.6 Hz, 2H), 2.95 (t, J=7.1 Hz, 4H), 2.17 (p, J=7.1 Hz, 2H). HPLC (method B) $t_R$ 2.52 min (100.00 area %). Anal. ($C_{27}H_{32}N_4O_2 \cdot 2HCl \cdot H_2O$) C, H, N, Cl.

4,5-Dihydro-2-(2-(3-(5-(4,5-dihydro-1H-imidazol-2-yl) benzofuran-2-yl)propyl)benzofuran-5-yl)-1H-imidazole dihydrochloride (16). White solid (0.72 g, 97%): mp 203-205° C. $^1$H NMR (DMSO-$d_6$) δ10.80 (s, 4H), 8.32 (d, J=1.6 Hz, 2H), 8.12 (dd, J=8.8, 1.6 Hz, 2H), 7.78 (d, 8.8 Hz, 2H), 6.88 (s, 2H), 2.96 (t, J=7.1 Hz, 4H), 2.19 (p, J=7.1 Hz, 2H). HPLC (method A) $t_R$ 7.25 min (100.00 area %). Anal. ($C_{25}H_{24}N_4O_2 \cdot 2HCl \cdot 1.2H_2O$) C, H, N, Cl.

2-(3-(6-Amidinobenzofuran-2-yl)propyl)benzofuran-6-carboxamidine dihydrochloride (17). Light yellow solid (0.56 g, 53%): mp <300° C. (dec). $^1$H NMR (DMSO-$d_6$) δ9.42 (s, 4H), 9.21 (s, 4H), 8.11 (s, 2H), 7.85 (d, J=8.2 Hz, 2H), 7.65 (d, J=8.2 Hz, 2H), 6.85 (s, 2H), 2.97 (t, J=7.1 Hz, 4H), 2.18 (p, J=7.1 Hz, 2H). HPLC (method B) $t_R$ 1.14 min (100.00 area %). Anal. ($C_{21}H_{20}N_4O_2 \cdot 2HCl \cdot 0.3H_2O$) C, H, N, Cl.

2-(3-(6-Amidinobenzofuran-2-yl)propyl)-N-isopropyl-benzofuran-6-carboxamidine dihydrochloride (18). White solid (0.52 g, 41%): mp 289-291° C. (dec). $^1$H NMR (DMSO-$d_6$) δ9.54 (d, J=6.7 Hz, 2H), 9.42 (s, 2H), 9.06 (s, 2H), 7.97 (s, 2H), 7.75 (d, J=8.2 Hz, 2H), 7.57 (d, J=8.2 Hz, 2H), 6.85 (s, 2H), 4.08 (h, J=6.04 Hz, 2H), 2.96 (t, J=7.1 Hz, 4H), 2.20 (p, J=7.1, 2H), 1.29 (d, J=6.04 Hz, 12H). HPLC (method B) $t_R$ 2.33 min (100.00 area %). Anal. ($C_{27}H_{32}N_4O_2 \cdot 2HCl \cdot H_2O$) C, H, N, Cl.

4,5-Dihydro-2-(2-(3-(6-(4,5-dihydro-1H-imidazol-2-yl) benzofuran-2-yl)propyl)benzofuran-6-yl)-1H-imidazole dihydrochloride (19). White solid (0.69 g, 59%): mp >300° C. (dec). $^1$H NMR (DMSO-$d_6$) δ10.75 (s, 4H), 8.31 (s, 2H), 7.86 (d, J=8.2 Hz, 2H), 7.77 (d, J=8.2 Hz, 2H), 6.86 (s, 2H), 4.02 (s, 8H), 2.98 (t, J=6.6 Hz, 4H), 2.20 (p, J=6.6, 2H). HPLC (method B) $t_R$ 1.45 min (100.00 area %). Anal. ($C_{25}H_{24}N_4O_2 \cdot 2HCl \cdot 2H_2O$) C, H, N, Cl.

2-(4-(5-Amidinobenzofuran-2-yl)butyl)benzofuran-5-carboxamidine dihydrochloride (20). See Dann, O.; Char, H.;

Grießmeier, H.; Synthesen biskationischer, trypanocider 1-Benzofuran-Verbindungen. *Liebigs Ann. Chem.* 1982, 1836-1869. White solid (0.13 g, 38%): mp 325-327° C. (dec) (lit. 335° C. (dec)) (1.5 M HCl). $^1$H NMR (DMSO-$d_6$) δ9.34 (s, 4H), 9.08 (s, 2H), 8.08 (d, J=1.6 Hz, 2H), 7.76 (d, J=8.2 Hz, 2H), 7.69 (dd, J=8.2, 1.6 Hz, 2H), 6.82 (s, 2H), 2.91 (br s, 2H), 1.81 (br s, 2H). HPLC (method B) $t_R$ 1.75 min (100.00 area %). Anal. ($C_{22}H_{22}N_4O_2$.2HCl.0.5$H_2O$) C, H, N, Cl.

2-(4-(5-Amidinobenzofuran-2-yl)butyl)-N-isopropylbenzofuran-5-carboxamidine dihydrochloride (21). White solid (0.17 g, 41%): mp 283-285° C. (dec) (1.5 M HCl). $^1$H NMR (DMSO-$d_6$) δ9.56 (d, J=8.2 Hz, 4H), 9.42 (s, 2H), 9.09 (s, 2H), 7.96 (d, J=1.6 Hz, 2H), 7.73 (d, J=8.2 Hz, 2H) 7.59 (dd, J=8.2, 1.6 Hz, 2H), 6.80 (s, 2H), 4.08 (p, J=6.0 Hz, 2H), 2.91 (br s, 2H), 1.81 (br s, 2H), 1.29 (d, J=6.0 Hz, 12H). HPLC (method B) $t_R$ 3.07 min (95.30 area %). Anal. ($C_{28}H_{34}N_4O_2$.2HCl.1.2$H_2O$) C, H, N, Cl.

4,5-Dihydro-2-(2-(4-(5-(4,5-dihydro-1H-imidazol-2-yl) benzofuran-2-yl)butyl)benzofuran-5-yl)-1H-imidazole dihydrochloride (22). White solid (0.25 g, 63%): mp 323-324° C. (dec). $^1$H NMR (DMSO-$d_6$) δ10.78 (s, 4H), 8.33 (d, J=1.6 Hz, 2H), 7.94 (dd, J=8.8, 1.6 Hz, 2H), 7.78 (d, J=8.2 Hz, 2H), 6.84 (s, 2H), 4.01 (s, 8H), 2.91 (br s, 2H), 1.81 (br s, 2H). HPLC (method A) $t_R$ 7.82 min (100.00 area %). Anal. ($C_{26}H_{26}N_4O_2$.2HCl.2.5$H_2O$) C, H, N, Cl.

2-(4-(6-Amidinobenzofuran-2-yl)butyl)benzofuran-6-carboxamidine dihydrochloride (23). White solid (0.45 g, 73%): mp 328-330° C. (dec). $^1$H NMR (DMSO-$d_6$) δ9.37 (s, 4H), 9.14 (s, 4H), 8.09 (s, 2H), 7.76 (d, J=8.2 Hz, 2H), 7.65 (d, J=8.2 Hz, 2H), 6.81 (s, 2H), 2.93 (br s, 2H), 1.82 (br s, 2H). HPLC (method A) $t_R$ 7.15 min (100.00 area %). Anal. ($C_{22}H_{22}N_4O_2$.2HCl.1.5$H_2O$) C, H, N, Cl.

2-(4-(6-Amidinobenzofuran-2-yl)butyl)-N-isopropylbenzofuran-6-carboxamidine dihydrochloride (24). White solid (0.37 g, 51%): mp 282-283° C. (dec) (1.5 M HCl/EtOH/diethyl ether). $^1$H NMR (DMSO-$d_6$) δ9.55 (d, J=7.3 Hz, 2H), 9.44 (s, 2H), 9.09 (s, 2H), 7.98 (s, 2H), 7.75 (d, J=8.2 Hz, 2H), 7.58 (d, J=8.2 Hz, 2H), 6.81 (s, 2H), 4.08 (h, J=6.0 Hz, 2H), 2.93 (br s, 2H), 1.81 (br s, 2H), 1.29 (d, J=6.0 Hz, 12H). HPLC (method B) $t_R$ 2.92 min (100.00 area %). Anal. ($C_{28}H_{34}N_4O_2$.2HCl.0.5$H_2O$) C, H, N, Cl.

4,5-Dihydro-2-(2-(4-(6-(4,5-dihydro-1H-imidazol-2-yl) benzofuran-2-yl)butyl)benzofuran-6-yl)-1H-imidazole dihydrochloride (25). White solid (0.37 g, 54%): mp 343-345° C. (dec). $^1$H NMR (DMSO-$d_6$) δ10.66 (s, 4H), 8.28 (s, 2H), 7.84 (d, J=8.2 Hz, 2H), 7.82 (d, J=8.2 Hz, 2H), 6.84 (s, 2H), 4.02 (s, 8H), 2.94 (br s, 2H), 1.83 (br s, 2H). HPLC (method B) $t_R$ 1.94 min (100.00 area %). Anal. ($C_{26}H_{26}N_4O_2$.2HCl.0.7$H_2O$) C, H, N, Cl.

2-(5-(5-Amidinobenzofuran-2-yl)pentyl)benzofuran-5-carboxamidine dihydrochloride (26). White solid (0.40 g, 67): mp 156-157° C. (1.5 M aqueous HCl). $^1$H NMR (DMSO-$d_6$) δ9.36 (s, 4H), 9.14 (br s, 4H), 8.07 (s, 2H), 7.88 (d, J=8.8 Hz, 2H), 7.62 (dd, J=8.8, 1.6 Hz, 2H), 6.80 (s, 2H), 2.84 (t, J=7.7 Hz, 4H), 1.78 (m, 4H), 1.45 (m, 2H). HPLC (method B) $t_R$ 2.29 min (100.00 area %). Anal. ($C_{23}H_{24}N_4O_2$.2HCl.1.6$H_2O$) C, H, N, Cl.

2-(5-(5-Amidinobenzofuran-2-yl)pentyl)-N-isopropyl-benzofuran-5-carboxamidine dihydrochloride (27). White solid (0.20 g, 32%): mp 193-195° C. (1.5 M HCl). $^1$H NMR (DMSO-$d_6$) δ9.58 (d, J=7.0 Hz, 2H), 9.46 (s, 2H), 9.16 (s, 2H), 7.97 (s, 2H), 7.72 (d, J=8.2 Hz, 2H), 7.59 (d, J=8.2 Hz, 2H), 6.79 (s, 2H), 4.11 (h, J=6.0 Hz, 2H), 2.85 (t, J=6.6 Hz, 4H), 1.77 (m, 4H), 1.45 (p, J=5.5 Hz, 12H). HPLC (method A) $t_R$ 8.57 min (97.68 area %). Anal. ($C_{29}H_{36}N_4O_2$.2Cl.0.7$H_2O$) C, H, N, Cl.

4,5-Dihydro-2-(2-(5-(5-(4,5-dihydro-1H-imidazol-2-yl) benzofuran-2-yl)pentyl)benzofuran-5-yl)-1H-imidazole dihydrochloride (28). White solid (0.22 g, 37%): mp 155-157° C. (1.5 M HCl). $^1$H NMR (DMSO-$d_6$) δ10.69 (s, 4H), 8.28 (s, 2H), 7.89 (dd, J=8.8, 1.6 Hz, 2H), 7.70 (d, J=8.2 Hz, 2H), 6.82 (s, 2H), 4.01 (s, 8H), 2.85 (t, J=7.1 Hz, 4H), 1.78 (m, 4H), 1.46 (m, 2H). HPLC (method A) $t_R$ 8.25 min (100.00 area %). Anal. ($C_{27}H_{28}N_4O_2$.2HCl.2$H_2O$) C, H, N, Cl.

2-(5-(6-Amidinobenzofuran-2-yl)pentyl)benzofuran-6-carboxamidine dihydrochloride (29). White solid (0.25 g, 25.5%): mp 243-245° C. (dec). $^1$H NMR (DMSO-$d_6$) δ9.42 (s, 4H), 9.21 (s, 4H), 8.10 (s, 2H), 7.76 (d, J=8.2 Hz, 2H), 7.65 (d, J=8.2 Hz, 2H), 6.79 (s, 2H), 2.86 (t, J=7.1 Hz, 4H), 1.78 (m, 4H), 1.44 (m, 2H). HPLC (method B) $t_R$ 2.06 min (95.75 area %). Anal. ($C_{23}H_{24}N_4O_2$.2HCl.0.7$H_2O$) C, H, N, Cl.

2-(5-(6-Amidinobenzofuran-2-yl)pentyl)-N-isopropyl-benzofuran-6-carboxamidine dihydrochloride (30). White solid (0.48 g, 39.7%): mp 193-195° C. (dec) (1.5 M HCl, i-PrOH). $^1$H NMR (DMSO-$d_6$) δ9.55 (d, J=7.0 Hz, 2H), 9.45 (s, 2H), 9.10 (s, 2H), 7.96 (s, 2H), 7.73 (d, J=8.2 Hz, 2H), 7.57 (d, J=8.2 Hz, 2H), 6.79 (s, 2H), 4.10 (m, 2H), 2.86 (m, 4H), 1.78 (m, 4H), 1.46 (m, 2H), 1,29 (d, J=6.0 Hz, 12H). HPLC (method B) $t_R$ 3.47 min (96.74 area %). Anal. ($C_{29}H_{36}N_4O_2$.2HCl.1.3$H_2O$) C, H, N, Cl.

4,5-Dihydro-2-(2-(5-(6-(4,5-dihydro-1H-imidazol-2-yl) benzofuran-2-yl)pentyl)benzofuran-6-yl)-1H-imidazole dihydrochloride (31). White solid (0.62 g, 48.8%): mp 308-310° C. (dec) (1.5 M HCl, i-PrOH). $^1$NMR (DMSO-$d_6$) δ10.74 (s, 4H), 8.31 (s, 2H), 7.86 (d, J=8.2 Hz, 2H), 7.78 (d, J=8.2 Hz, 2H), 6.81 (s, 2H), 4.02 (s, 8H), 2.87 (t, J=7.14 Hz, 4H), 1.79 (m, 4H), 1.45 (m, 2H). HPLC (method B) $t_R$ 2.54 min (96.41 area %). Anal. ($C_{27}H_{28}N_4O_2$.2HCl.1.5$H_2O$.0.3i-PrOH) C, H, N, Cl.

2-(3-(3-(4-Carbamimidoylphenoxy)propoxy)phenyl)ben-zofuran-5-carboxamidine dihydrochloride (32). White solid (0.23 g, 51%): mp 175-178° C. $^1$H NMR (DMSO-$d_6$) δ9.41 (br s, 2H), 9.22 (br s, 2H), 9.12 (br s, 2H), 8.94 (br s, 2H), 8.19 (d, J=1.8 Hz, 1H), 7.90 (d, J=8.6 Hz, 1H), 7.85 (d, J=8.8 Hz, 2H), 7.78 (dd, J=8.6, 1.8 Hz, 1H), 7.70 (s, 1H), 7.57 (d, J=7.8 Hz, 1H), 7.55 (m, 1H), 7.43 (dd, J=7.8 and 7.8 Hz, 1H), 7.21 (d, J=8.8 Hz, 2H), 7.07 (dd, J=7.8, 1.8 Hz, 1H), 4.36-4.16 (m, 4H), 2.30-2.18 (m, 2H). HPLC (method A) $t_R$ 7.91 min (100.0 area %). Anal. ($C_{25}H_{24}N_4O_3$.2HCl.1.4$H_2O$) C, H, N, Cl.

2-(3-(3-(4-(N-Isopropylcarbamimidoyl)phenoxy)pro-poxy)phenyl)-N-isopropylbenzofuran-5-carboxamidine dihydrochloride (33). White solid (0.24 g, 47%): mp 205-208° C. $^1$H NMR (DMSO-$d_6$) δ9.60 (d, J=8.2 Hz, 1H), 9.44 (br, 1H), 9.38 (d, J=8.4 Hz, 1H), 9.26 (br s, 1H), 9.05 (br s, 1H), 8.87 (br s, 1H), 8.07 (d, J=1.8 Hz, 1H), 7.88 (d, J=8.2 Hz, 1H), 7.71 (d, J=8.8 Hz, 2H), 7.68 (s, 1H), 7.67 (dd, J=8.6, 1.8 Hz, 1H), 7.57 (d, J=7.8 Hz, 1H), 7.54 (m, 1H), 7.47 (dd, J=7.8, 7.8 Hz, 1H), 7.19 (d, J=8.8 Hz, 2H), 7.08 (dd, J=7.8, 1.8 Hz, 1H), 4.35-4.20 (m, 4H), 4.15-3.95 (m, 2H), 2.35-2.15 (m, 2H), 1.30 (d, J=6.3 Hz, 6H), 1.26 (d, J=6.3 Hz, 6H). HPLC (method A) $t_R$ 8.96 min (100.0 area %). Anal. ($C_{31}H_{36}N_4O_3$.2HCl.1.5$H_2O$) C, H, N, Cl.

2-(2-(3-(3-(4-(4,5-Dihydro-1H-imidazol-2-yl)phenoxy) propoxy)phenyl)benzofuran-5-yl)-4,5-dihydro-1H-imida-zole dihydrochloride (34). White solid (0.12 g, 25%): mp 193-197° C. $^1$H NMR (DMSO-$d_6$) δ10.86 (br s, 2H), 10.68 (br s, 2H), 8.48 (d, J=1.8 Hz, 1H), 8.08 (d, J=9.0 Hz, 2H), 8.04 (dd, J=8.8, 1.8 Hz, 1H), 7.93 (d, J=8.8 Hz, 1H), 7.74 (s, 1H), 7.57 (d, J=8.4 Hz, 1H), 7.56 (m, 1H), 7.46 (dd, J=8.4, 8.4 Hz, 1H), 7.24 (d, J=9.0 Hz, 2H), 7.07 (dd, J=8.4, 1.8 Hz, 1H), 4.35-4.20 (m, 4H), 4.03 (s, 4H), 3.95 (s, 4H), 2.35-2.20 (m, 2H). HPLC (method A) t_R 8.35 min (100.0 area %). Anal. ($C_{29}H_{28}N_4O_3 \cdot 2HCl \cdot 1.8H_2O$) C, H, N, Cl.

2-(3-(4-(4-Carbamimidoylphenoxy)butoxy)phenyl)benzofuran-5-carboxamidine dihydrochloride (35). White solid (0.14 g, 32%): mp 284-286° C. $^1$H NMR (DMSO-$d_6$) δ 9.49 (br s, 2H), 9.28 (br s, 4H), 9.09 (br s, 2H), 8.23 (d, J=1.8 Hz, 1H), 7.89 (d, J=8.7 Hz, 1H), 7.88 (d, J=8.9 Hz, 2H), 7.80 (dd, J=8.7, 1.8 Hz, 1H), 7.70 (s, 1H), 7.57 (d, J=7.8 Hz, 1H), 7.53 (m, 1H), 7.46 (dd, J=7.8, 7.8 Hz, 1H), 7.18 (d, J=8.9 Hz, 2H), 7.05 (dd, J=7.8, 1.8 Hz, 1H), 4.25-4.05 (m, 4H), 2.05-1.85 (m, 4H). HPLC (method A) t_R 8.28 min (100.0 area %). Anal. ($C_{26}H_{26}N_4O_3 \cdot 2HCl \cdot 0.4H_2O$) C, H, N, Cl.

2-(3-(4-(4-(N-Isopropylcarbamimidoyl)phenoxy)butoxy)phenyl)-N-isopropylbenzofuran-5-carboxamidine dihydrochloride (36). White solid (0.12 g, 24%): mp 207-210° C. $^1$H NMR (DMSO-$d_6$) δ 9.66 (d, J=8.0 Hz, 1H), 9.54 (br s, 1H), 9.43 (d, J=8.0 Hz, 1H), 9.35 (br s, 1H), 9.21 (br s, 1H), 9.03 (br s, 1H), 8.10 (d, J=1.8 Hz, 1H), 7.87 (d, J=8.7 Hz, 1H), 7.74 (d, J=8.9 Hz, 2H), 7.69 (dd, J=8.7, 1.8 Hz, 1H), 7.69 (s, 1H), 7.57 (d, J=7.8 Hz, 1H), 7.53 (m, 1H), 7.46 (dd, J=7.8, 7.8 Hz, 1H), 7.15 (d, J=8.9 Hz, 2H), 7.06 (dd, J=7.8, 1.8 Hz, 1H), 4.25-4.10 (m, 4H), 4.20-4.00 (m, 2H), 2.05-1.85 (m, 2H), 1.30 (d, J=6.4 Hz, 6H), 1.26 (d, J=6.4 Hz, 6H). HPLC (method A) t_R 9.27 min (100.0 area %). Anal. ($C_{32}H_{38}N_4O_3 \cdot 2HCl \cdot 0.6EtOH \cdot 1H_2O$) C, H, N, Cl.

2-(2-(3-(4-(4-(4,5-Dihydro-1H-imidazol-2-yl)phenoxy)butoxy)phenyl)benzofuran-5-yl)-4,5-dihydro-1H-imidazole dihydrochloride (37). White solid (0.16 g, 33%): mp 190-195° C. $^1$H NMR (DMSO-$d_6$) δ 10.90 (br s, 2H), 10.64 (br s, 2H), 8.48 (d, J=1.8 Hz, 1H), 8.07 (d, J=9.0 Hz, 2H), 8.05 (dd, J=8.7, 1.8 Hz, 1H), 7.93 (d, J=8.7 Hz, 1H), 7.73 (s, 1H), 7.57 (d, J=7.9 Hz, 1H), 7.53 (m, 1H), 7.47 (dd, J=7.9, 7.9 Hz, 1H), 7.21 (d, J=9.0 Hz, 2H), 7.05 (dd, J=7.9, 1.8 Hz, 1H), 4.25-4.15 (m, 4H), 4.03 (s, 4H), 3.95 (s, 4H), 2.05-1.85 (m, 4H). HPLC (method A) t_R 8.64 min (100.0 area %). Anal. ($C_{30}H_{30}N_4O_3 \cdot 2HCl \cdot 2H_2O$) C, H, N, Cl.

2-(3-(5-(4-Carbamimidoylphenoxy)pentyloxy)phenyl)benzofuran-5-carboxamidine dihydrochloride (38). White solid (0.24 g, 27%): mp 165-168° C. $^1$H NMR (DMSO-$d_6$) δ 9.40 (br s, 2H), 9.19 (br s, 2H), 9.09 (br s, 2H), 8.92 (br s, 2H), 8.18 (d, J=1.8 Hz, 1H), 7.89 (d, J=8.7 Hz, 1H), 7.82 (d, J=8.8 Hz, 2H), 7.77 (dd, J=8.7, 1.8 Hz, 1H), 7.70 (s, 1H), 7.56 (d, J=8.0 Hz, 1H), 7.52 (m, 1H), 7.45 (dd, J=8.0, 8.0 Hz, 1H), 7.17 (d, J=8.8 Hz, 2H), 7.04 (dd, J=8.0, 1.8 Hz, 1H), 4.25-4.05 (m, 4H), 2.00-1.85 (m, 4H), 1.85-1.75 (m, 2H). HPLC (method A) t_R 8.62 min (100.0 area %). Anal. ($C_{27}H_{28}N_4O_3 \cdot 2HCl \cdot 1.9H_2O$) C, H, N, Cl.

2-(3-(5-(4-(N-Isopropylcarbamimidoyl)phenoxy)pentyloxy)phenyl)-N-isopropylbenzofuran-5-carboxamidine dihydrochloride (39). White solid (0.12 g, 24%): mp 225-227° C. $^1$H NMR (DMSO-$d_6$) δ 9.65 (d, J=8.0 Hz, 1H), 9.53 (br s, 1H), 9.42 (d, J=8.0 Hz, 1H), 9.33 (br s, 1H), 9.20 (br s, 1H), 9.01 (br s, 1H), 8.09 (d, J=1.8 Hz, 1H), 7.87 (d, J=8.6 Hz, 1H), 7.72 (d, J=8.9 Hz, 2H), 7.69 (dd, J=8.6, 1.8 Hz, 1H), 7.69 (s, 1H), 7.56 (d, J=7.8 Hz, 1H), 7.52 (m, 1H), 7.45 (dd, J=7.8, 7.8 Hz, 1H), 7.14 (d, J=8.9 Hz, 2H), 7.04 (dd, J=7.8, 1.8 Hz, 1H), 4.25-4.00 (m, 6H), 1.95-1.80 (m, 4H), 1.75-1.55 (m, 2H), 1.30 (d, J=6.4 Hz, 6H), 1.26 (d, J=6.4 Hz, 6H). HPLC (method A) t_R 9.59 min (100.0 area %). Anal. ($C_{33}H_{40}N_4O_3 \cdot 2HCl \cdot 0.5H_2O$) C, H, N, Cl.

2-(2-(3-(5-(4-(4,5-Dihydro-1H-imidazol-2-yl)phenoxy)pentyloxy)phenyl)benzofuran-5-yl)-4,5-dihydro-1H-imidazole dihydrochloride (40). Yellowish solid (0.12 g, 13%): mp 180-182° C. $^1$H NMR (DMSO-$d_6$) δ 10.91 (br s, 2H), 10.66 (br s, 2H), 8.49 (br s, 1H), 8.07 (d, J=8.9 Hz, 2H), 8.05 (dd, J=8.7, 1.8 Hz, 1H), 7.92 (d, J=8.7 Hz, 1H), 7.73 (s, 1H), 7.56 (d, J=7.8 Hz, 1H), 7.53 (m, 1H), 7.42 (dd, J=7.8, 7.8 Hz, 1H), 7.19 (d, J=8.9 Hz, 2H), 7.04 (dd, J=7.8, 1.8 Hz, 1H), 4.25-4.05 (m, 4H), 4.03 (s, 4H), 3.95 (s, 4H), 1.95-1.75 (m, 4H), 1.70-1.55 (m, 2H). HPLC (method A) t_R 8.94 min (97.92 area %). Anal. ($C_{31}H_{32}N_4O_3 \cdot 1.4H_2O$) C, H, N, Cl.

2-(3-(6-(4-Carbamimidoylphenoxy)hexyloxy)phenyl)benzofuran-5-carboxamidine dihydrochloride (41). White solid (0.13 g, 30%): mp 208-210° C. $^1$H NMR (DMSO-$d_6$) δ 9.47 (br s, 2H), 9.26 (br s, 4H), 9.05 (br s, 2H), 8.21 (d, J=1.8 Hz, 1H), 7.89 (d, J=8.7 Hz, 1H), 7.85 (d, J=8.9 Hz, 2H), 7.79 (dd, J=8.7, 1.8 Hz, 1H), 7.70 (s, 1H), 7.56 (d, J=8.0 Hz, 1H), 7.52 (m, 1H), 7.45 (dd, J=8.0, 8.0 Hz, 1H), 7.16 (d, J=8.9 Hz, 2H), 7.04 (dd, J=8.0, 1.8 Hz, 1H), 4.15-4.05 (m, 4H), 1.90-1.75 (m, 4H), 1.65-1.45 (m, 4H). HPLC (method A) t_R 8.92 min (100.0 area %). Anal. ($C_{28}H_{30}N_4O_3 \cdot 2HCl \cdot 0.7H_2O$) C, H, N, Cl.

2-(3-(6-(4-(N-Isopropylcarbamimidoyl)phenoxy)hexyloxy)phenyl)-N-isopropylbenzofuran-5-carboxamidine dihydrochloride (42). White solid (0.15 g, 31%): mp 224-227° C. $^1$H NMR (DMSO-$d_6$) δ 9.66 (d, J=8.0 Hz, 1H), 9.53 (br s, 1H), 9.42 (d, J=8.0 Hz, 1H), 9.34 (br s, 1H), 9.21 (br s, 1H), 9.02 (br s, 1H), 8.09 (d, J=1.8 Hz, 1H), 7.87 (d, J=8.7 Hz, 1H), 7.72 (d, J=8.9 Hz, 2H), 7.69 (dd, J=8.7, 1.8 Hz, 1H), 7.69 (s, 1H), 7.56 (d, J=8.0 Hz, 1H), 7.52 (m, 1H), 7.45 (dd, J=8.0, 8.0 Hz, 1H), 7.14 (d, J=8.9 Hz, 2H), 7.04 (dd, J=8.0, 1.8 Hz, 1H), 4.25-4.00 (m, 6H), 1.85-1.70 (m, 4H), 1.60-1.45 (m, 4H), 1.30 (d, J=6.4 Hz, 6H), 1.26 (d, J=6.4 Hz, 6H). HPLC (method A) t_R 9.93 min (100.0 area %). Anal. ($C_{34}H_{42}N_4O_3 \cdot 2HCl \cdot 0.7H_2O$) C, H, N, Cl.

2-(2-(3-(6-(4-(4,5-Dihydro-1H-imidazol-2-yl)phenoxy)hexyloxy)phenyl)benzofuran-5-yl)-4,5-dihydro-1H-imidazole (43). White solid (0.11 g, 23%): mp 178-182° C. $^1$H NMR (DMSO-$d_6$) δ 10.88 (br s, 2H), 10.64 (br s, 2H), 8.48 (d, J=1.8 Hz, 1H), 8.06 (d, J=8.9 Hz, 2H), 8.05 (dd, J=8.8, 1.8 Hz, 1H), 7.92 (d, J=8.8 Hz, 1H), 7.74 (s, 1H), 7.56 (d, J=7.8 Hz, 1H), 7.53 (m, 1H), 7.45 (dd, J=7.8, 7.8 Hz, 1H), 7.18 (d, J=8.9 Hz, 2H), 7.04 (dd, J=7.8, 1.8 Hz, 1H), 4.18-4.05 (m, 4H), 4.03 (s, 4H), 3.95 (s, 4H), 1.85-1.70 (m, 4H), 1.65-1.45 (m, 4H). HPLC (method A) t_R 9.35 min (98.44 area %). Anal. ($C_{32}H_{34}N_4O_3 \cdot 2HCl \cdot 1.3H_2O$) C, H, N, Cl.

2-(4-(3-(4-Carbamimidoylphenoxy)propoxy)phenyl)benzofuran-5-carboxamidine dihydrochloride (44). Yellowish solid (0.20 g, 49%): mp 287-289° C. $^1$H NMR (DMSO-$d_6$) δ 9.40 (br s, 2H), 9.23 (br s, 2H), 9.15 (br s, 2H), 8.99 (br s, 2H), 8.15 (d, J=1.5 Hz, 1H), 7.93 (d, J=8.6 Hz, 2H), 7.86 (m, J=8.6 Hz, 3H), 7.74 (dd, J=8.6, 1.5 Hz, 1H), 7.49 (s, 1H), 7.20 (d, J=8.6 Hz, 2H), 7.13 (d, J=8.6 Hz, 2H), 4.33-4.20 (m, 4H), 2.30-2.20 (m, 2H). HPLC (method A) t_R 7.76 min (98.48 area %). Anal. ($C_{25}H_{24}N_4O_3 \cdot 2HCl \cdot 1H_2O$) C, H, N, Cl.

2-(4-(3-(4-(N-Isopropylcarbamimidoyl)phenoxy)propoxy)phenyl)-N-isopropylbenzofuran-5-carboxamidine dihydrochloride (45). White solid (0.21 g, 44%): mp 301-302° C. $^1$H NMR (DMSO-$d_6$) δ 9.60 (d, J=8.8 Hz, 1H), 9.46 (br s, 1H), 9.41 (d, J=8.5 Hz, 1H), 9.30 (br s, 1H), 9.11 (br s, 1H), 8.96 (br s, 1H), 8.03 (br s, 1H), 7.92 (d, J=8.8 Hz, 2H), 7.83 (d, J=8.5 Hz, 1H), 8.73 (d, J=8.8 Hz, 2H), 7.63 (dd, J=8.5, 1.5 Hz, 1H), 7.47 (s, 1H), 7.18 (d, J=8.8 Hz, 2H), 7.14 (d, J=8.8 Hz, 2H), 4.30-4.20 (m, 4H), 4.20-3.97 (m, 2H), 1.30 (d, J=6.3 Hz, 6H), 1.26 (d, J=6.3 Hz, 6H). HPLC (method A) t_R 8.80 min (99.17 area %). Anal. ($C_{31}H_{36}N_4O_3 \cdot 2HCl \cdot 1H_2O$) C, H, N, Cl.

2-(2-(4-(3-(4-(4,5-Dihydro-1H-imidazol-2-yl)phenoxy)propoxy)phenyl)benzofuran-5-yl)-4,5-dihydro-1H-imidazole dihydrochloride (46). White solid (0.24 g, 54%): mp 262-263° C. $^1$H NMR (DMSO-$d_6$) δ 10.76 (br s, 2H), 10.57 (br s, 2H), 8.38 (s, 1H), 8.04 (d, J=8.8 Hz, 2H), 7.96 (d, J=8.2 Hz, 1H), 7.93 (d, J=8.8 Hz, 2H), 7.90 (d, J=8.2 Hz, 1H), 7.53 (s, 1H), 7.24 (d, J=8.8 Hz, 2H), 7.14 (d, J=8.8 Hz, 2H), 4.40-4.20 (m, 4H), 4.03 (s, 4H), 3.96 (s, 4H), 2.30-2.20 (m, 2H). HPLC (method A) $t_R$ 8.14 min (99.24 area %). Anal. ($C_{29}H_{28}N_4O_3 \cdot 2HCl \cdot 1.5EtOH \cdot 0.5H_2O$) C, H, N, Cl.

2-(4-(4-(4-Carbamimidoylphenoxy)butoxy)phenyl)benzofuran-5-carboxamidine dihydrochloride (47). White solid (0.20 g, 23%): mp 310° C. $^1$H NMR (DMSO-$d_6$) δ9.40 (br s, 2H), 9.23 (br s, 2H), 9.14 (br s, 2H), 8.98 (br s, 2H), 8.15 (s, 1H), 7.92 (d, J=8.6 Hz, 2H), 7.90-7.78 (m, 3H), 7.74 (dd, J=8.6, 1.4 Hz, 1H), 7.49 (s, 1H), 7.18 (d, J=8.6 Hz, 2H), 7.12 (d, J=8.6 Hz, 2H), 4.36-4.10 (m, 4H), 2.10-1.80 (m, 4H). HPLC (method A) $t_R$ 8.19 min (100.0 area %). Anal. ($C_{26}H_{26}N_4O_3 \cdot 2HCl \cdot 0.9H_2O$) C, H, N, Cl.

2-(4-(4-(4-(N-Isopropylcarbamimidoyl)phenoxy)butoxy)phenyl)-N-isopropylbenzofuran-5-carboxamidine dihydrochloride (48). White solid (0.26 g, 25%): mp 305° C. $^1$H NMR (DMSO-$d_6$) δ9.60 (d, J=8.8 Hz, 1H), 9.46 (br s, 1H), 9.40 (d, J=8.5 Hz, 1H), 9.29 (br s, 1H), 9.10 (br s, 1H), 8.94 (br s, 1H), 8.03 (d, J=1.5 Hz, 1H), 7.91 (d, J=8.8 Hz, 2H), 7.83 (d, J=8.5 Hz, 1H), 8.72 (d, J=8.8 Hz, 2H), 7.63 (dd, J=8.5, 1.5 Hz, 1H), 7.47 (s, 1H), 7.15 (d, J=8.8 Hz, 2H), 7.12 (d, J=8.8 Hz, 2H), 4.25-3.95 (m, 6H), 2.00-1.85 (m, 4H), 1.30 (d, J=6.4 Hz, 6H), 1.27 (d, J=6.4 Hz, 6H). HPLC (method A) $t_R$ 9.22 min (100.0 area %). Anal. ($C_{32}H_{38}N_4O_3 \cdot 2HCl \cdot 1.2H_2O$) C, H, N, Cl.

2-(2-(4-(4-(4-(4,5-Dihydro-1H-imidazol-2-yl)phenoxy)butoxy)phenyl)benzofuran-5-yl)-4,5-dihydro-1H-imidazole dihydrochloride (49). White solid (0.39 g, 40%): mp 291-293° C. $^1$H NMR (DMSO-$d_6$) δ10.71 (br s, 2H), 10.52 (br s, 2H), 8.36 (s, 1H), 8.01 (d, J=8.8 Hz, 2H), 7.96-7.85 (m, 4H), 7.52 (s, 1H), 7.21 (d, J=8.8 Hz, 2H), 7.10 (d, J=8.4 Hz, 2H), 4.25-4.05 (m, 4H), 4.03 (s, 4H), 3.96 (s, 4H), 1.98-1.84 (m, 4H). HPLC (method A) $t_R$ 8.54 min (100.0 area %). Anal. ($C_{30}H_{30}N_4O_3 \cdot 2HCl \cdot 1.5H_2O$) C, H, N, Cl.

2-(4-(5-(4-Carbamimidoylphenoxy)pentyloxy)phenyl)benzofuran-5-carboxamidine dihydrochloride (50). White solid (0.23 g, 35%): mp 290° C. (dec). $^1$H NMR (DMSO-$d_6$) δ9.43 (br s, 2H), 9.25 (br s, 2H), 9.21 (br s, 2H), 9.05 (br s, 2H), 8.16 (s, 1H), 7.90 (d, J=8.6 Hz, 2H), 7.86 (d, J=8.8 Hz, 2H), 7.75 (d, J=8.6 Hz, 2H), 7.48 (s, 1H), 7.16 (d, J=8.8 Hz, 2H), 7.10 (d, J=8.6 Hz, 2H), 4.20-4.00 (m, 4H), 1.92-1.70 (m, 4H), 1.70-1.50 (m, 2H). HPLC (method B) $t_R$ 3.13 min (100.0 area %). Anal. ($C_{27}H_{28}N_4O_3 \cdot 2HCl \cdot 1.1H_2O$) C, H, N, Cl.

2-(4-(5-(4-(N-Isopropylcarbamimidoyl)phenoxy)pentyloxy)phenyl)-N-isopropylbenzofuran-5-carboxamidine dihydrochloride (51). White solid (0.16 g, 21%): mp 260-263° C. $^1$H NMR (DMSO-$d_6$) δ9.59 (d, J=8.8 Hz, 1H), 9.45 (br s, 1H), 9.38 (d, J=8.8 Hz, 1H), 9.28 (br s, 1H), 9.09 (br s, 1H), 8.93 (br s, 1H), 8.03 (d, J=1.6 Hz, 1H), 7.91 (d, J=8.8 Hz, 2H), 7.83 (d, J=8.5 Hz, 2H), 8.72 (d, J=8.8 Hz, 2H), 7.63 (dd, J=8.5, 1.6 Hz, 1H), 7.47 (s, 1H), 7.14 (d, J=8.8 Hz, 2H), 7.11 (d, J=8.8 Hz, 2H), 4.15-3.95 (m, 6H), 1.90-1.75 (m, 4H), 1.70-1.50 (m, 2H), 1.30 (d, J=6.4 Hz, 6H), 1.26 (d, J=6.4 Hz, 6H). HPLC (method B) $t_R$ 4.67 min (100.0 area %). Anal. ($C_{33}H_{40}N_4O_3 \cdot 2HCl \cdot 0.8H_2O$) C, H, N, Cl.

2-(2-(4-(5-(4-(4,5-Dihydro-1H-imidazol-2-yl)phenoxy)pentyloxy)phenyl)benzofuran-5-yl)-4,5-dihydro-1H-imidazole dihydrochloride (52). White solid (0.19 g, 27%): mp 258-261° C. $^1$H NMR (DMSO-$d_6$) δ10.80 (br s, 2H), 10.57 (br s, 2H), 8.38 (s, 1H), 8.03 (d, J=8.8 Hz, 2H), 7.96 (dd, J=8.8, 1.3 Hz, 1H), 7.93-7.75 (m, 3H), 7.51 (s, 1H), 7.20 (d, J=8.8 Hz, 2H), 7.10 (d, J=8.8 Hz, 2H), 4.20-4.05 (m, 4H), 4.02 (s, 4H), 3.96 (s, 4H), 1.90-1.75 (m, 4H), 1.68-1.52 (m, 2H). HPLC (method A) $t_R$ 8.92 min (100.0 area %). Anal. ($C_{31}H_{32}N_4O_3 \cdot 2HCl \cdot 2.1H_2O$) C, H, N, Cl.

2-(4-(6-(4-Carbamimidoylphenoxy)hexyloxy)phenyl)benzofuran-5-carboxamidine dihydrochloride (53). White solid (0.27 g, 37%): mp 310-311° C. $^1$H NMR (DMSO-$d_6$) δ9.37 (br s, 2H), 9.19 (br s, 2H), 9.05 (br s, 2H), 8.88 (br s, 2H), 8.13 (s, 1H), 7.91 (d, J=8.6 Hz, 2H), 7.90-7.75 (m, 3H), 7.71 (dd, J=8.8, 1.3 Hz, 1H), 7.48 (s, 1H), 7.15 (d, J=8.8 Hz, 2H), 7.09 (d, J=8.8 Hz, 2H), 4.15-3.95 (m, 4H), 1.85-1.65 (m, 4H), 1.60-1.40 (m, 4H). HPLC (method A) $t_R$ 8.90 min (100.0 area %). Anal. ($C_{28}H_{30}N_4O_3 \cdot 2HCl \cdot 0.2H_2O$) C, H, N, Cl.

2-(4-(6-(4-(N-Isopropylcarbamimidoyl)phenoxy)hexyloxy)phenyl)-N-isopropylbenzofuran-5-carboxamidine dihydrochloride (54). White solid (0.30 g, 36%): mp 288-291° C. $^1$H NMR (DMSO-$d_6$) δ9.60 (d, J=8.5 Hz, 1H), 9.47 (br s, 1H), 9.39 (d, J=8.3 Hz, 1H), 9.30 (br s, 1H), 9.12 (br s, 1H), 8.96 (br s, 1H), 8.03 (d, J=1.5 Hz, 1H), 7.90 (d, J=8.8 Hz, 2H), 7.83 (d, J=8.6 Hz, 1H), 8.71 (d, J=8.8 Hz, 2H), 7.63 (dd, J=8.6, 1.5 Hz, 1H), 7.47 (s, 1H), 7.13 (d, J=8.8 Hz, 2H), 7.10 (d, J=8.8 Hz, 2H), 4.15-3.95 (m, 6H), 1.85-1.65 (m, 4H), 1.60-1.40 (m, 4H), 1.30 (d, J=6.4 Hz, 6H), 1.26 (d, J=6.4 Hz, 6H). HPLC (method A) $t_R$ 9.94 min (98.33 area %). Anal. ($C_{34}H_{42}N_4O_3 \cdot 2HCl \cdot 0.7H_2O$) C, H, N, Cl.

2-(2-(4-(6-(4-(4,5-Dihydro-1H-imidazol-2-yl)phenoxy)hexyloxy)phenyl)benzofuran-5-yl)-4,5-dihydro-1H-imidazole dihydrochloride (55). White solid (0.29 g, 37%): mp 275-277° C. $^1$H NMR (DMSO-$d_6$) δ10.62 (br s, 4H), 8.36 (s, 1H), 8.02 (d, J=8.8 Hz, 2H), 7.96-7.85 (m, 4H), 7.52 (s, 1H), 7.20 (d, J=8.8 Hz, 2H), 7.10 (d, J=8.6 Hz, 2H), 4.20-4.00 (m, 4H), 4.03 (s, 4H), 3.96 (s, 4H), 1.90-1.70 (m, 4H), 1.60-1.40 (m, 4H). HPLC (method A) $t_R$ 9.27 min (97.92 area %). Anal. ($C_{32}H_{34}N_4O_3 \cdot 2HCl \cdot 2.8H_2O$) C, H, N, Cl.

2-(3-(3-(4-Carbamimidoylphenoxy)propoxy)phenyl)benzofuran-6-carboxamidine dihydrochloride (56). Yellowish solid (0.14 g, 24%): mp 196-200° C. $^1$H NMR (DMSO-$d_6$) δ9.31 (br s, 8H), 8.22 (s, 1H), 7.89 (d, J=8.2 Hz, 1H), 7.88 (d, J=8.8 Hz, 2H), 7.77 (dd, J=8.2, 1.7 Hz, 1H), 7.68 (s, 1H), 7.58 (d, J=8.2 Hz, 1H), 7.55 (m, 1H), 7.48 (dd, J=8.2, 8.2 Hz, 1H), 7.21 (d, J=8.8 Hz, 2H), 7.09 (dd, J=8.2, 1.7 Hz, 1H), 4.38-4.22 (m, 4H), 2.36-2.20 (m, 2H). HPLC (method A) $t_R$ 7.93 min (100.0 area %). Anal. ($C_{25}H_{24}N_4O_3 \cdot 2HCl \cdot 0.4EtOH \cdot 0.6H_2O$) C, H, N, Cl.

2-(3-(3-(4-(N-Isopropylcarbamimidoyl)phenoxy)propoxy)phenyl)-N-isopropylbenzofuran-6-carboxamidine dihydrochloride (57). White solid (0.26 g, 38%): mp 213-217° C. $^1$H NMR (DMSO-$d_6$) δ9.69 (d, J=8.2 Hz, 1H), 9.59 (br s, 1H), 9.45 (d, J=7.7 Hz, 1H), 9.37 (br s, 1H), 9.27 (br s, 1H), 9.06 (br s, 1H), 8.12 (br s, 1H), 7.87 (d, J=8.2 Hz, 1H), 7.75 (d, J=8.8 Hz, 2H), 7.68 (s, 1H), 7.66 (d, J=8.2 Hz, 1H), 7.60 (d, J=7.7 Hz, 1H), 7.55 (m, 1H), 7.48 (dd, J=8.2, 7.7 Hz, 1H), 7.19 (d, J=8.8 Hz, 2H), 7.09 (dd, J=7.8, 1.8 Hz, 1H), 4.35-4.25 (m, 4H), 4.20-4.00 (m, 2H), 2.36-2.20 (m, 2H), 1.31 (d, J=6.6 Hz, 6H), 1.27 (d, J=6.6 Hz, 6H). HPLC (method A) $t_R$ 8.95 min (100.0 area %). Anal. ($C_{31}H_{36}N_4O_3 \cdot 2HCl \cdot 0.6H_2O$) C, H, N, Cl.

2-(2-(3-(3-(4-(4,5-Dihydro-1H-imidazol-2-yl)phenoxy)propoxy)phenyl)benzofuran-6-yl)-4,5-dihydro-1H-imidazole dihydrochloride (58). White solid (0.28 g, 42%): mp 208-211° C. $^1$H NMR (DMSO-$d_6$) δ10.99 (br s, 2H), 10.69 (br s, 2H), 8.52 (br s, 1H), 8.09 (d, J=9.0 Hz, 2H), 7.99 (d, J=8.2 Hz, 1H), 7.93 (d, J=8.2 Hz, 1H), 7.68 (s, 1H), 7.59 (d, J=7.7 Hz, 1H), 7.54 (m, 1H), 7.47 (dd, J=8.2, 7.7 Hz, 1H), 7.24 (d, J=9.0 Hz, 2H), 7.10 (dd, J=8.2, 1.7 Hz, 1H), 4.35-4.20 (m, 4H), 4.03 (s, 4H), 3.95 (s, 4H), 2.35-2.20 (m, 2H). HPLC (method A) $t_R$ 8.23 min (100.0 area %). Anal. ($C_{29}H_{28}N_4O_3 \cdot 2HCl \cdot 1.8H_2O$) C, H, N, Cl.

2-(3-(4-(4-Carbamimidoylphenoxy)butoxy)phenyl)benzofuran-6-carboxamidine dihydrochloride (59). White solid (0.28 g, 60%): mp 278-280° C. $^1$H NMR (DMSO-$d_6$) δ9.49 (br s, 2H), 9.28 (br s, 4H), 9.07 (br s, 2H), 8.23 (br s, 1H), 7.89 (d, J=8.2 Hz, 1H), 7.87 (d, J=8.8 Hz, 2H), 7.77 (dd, J=8.2, 1.6 Hz, 1H), 7.67 (s, 1H), 7.57 (d, J=8.2 Hz, 1H), 7.53 (m, 1H), 7.47 (dd, J=8.2, 7.7 Hz, 1H), 7.18 (d, J=8.8 Hz, 2H), 7.08 (dd, J=8.2, 1.6 Hz, 1H), 4.25-4.10 (m, 4H), 2.10-1.85 (m, 4H). HPLC (method A) $t_R$ 8.23 min (100.0 area %). Anal. ($C_{26}H_{26}N_4O_3 \cdot 2HCl \cdot 0.8H_2O$) C, H, N, Cl.

2-(3-(4-(4-(N-Isopropylcarbamimidoyl)phenoxy)butoxy)phenyl)-N-isopropylbenzofuran-6-carboxamidine dihydrochloride (60). White solid (0.20 g, 37%): mp 228-230° C. $^1$H NMR (DMSO-$d_6$) δ 9.38 (br s, 6H), 8.11 (br s, 1H), 7.87 (d, J=8.2 Hz, 1H), 7.73 (d, J=9.3 Hz, 2H), 7.67 (s, 1H), 7.66 (dd, J=8.2, 1.6 Hz, 1H), 7.57 (d, J=7.7 Hz, 1H), 7.53 (m, 1H), 7.47 (dd, J=8.2, 7.87 Hz, 1H), 7.16 (d, J=9.3 Hz, 2H), 7.07 (dd, J=8.2, 1.6 Hz, 1H), 4.25-4.00 (m, 6H), 2.05-1.85 (m, 2H), 1.31 (d, J=6.3 Hz, 6H), 1.26 (d, J=6.3 Hz, 6H). HPLC (method A) $t_R$ 9.23 min (98.90 area %). Anal. ($C_{32}H_{38}N_4O_3 \cdot 2HCl \cdot 0.5H_2O$) C, H, N, Cl.

2-(2-(3-(4-(4-(4,5-Dihydro-1H-imidazol-2-yl)phenoxy)butoxy)phenyl)benzofuran-6-yl)-4,5-dihydro-1H-imidazole dihydrochloride (61). White solid (0.39 g, 76%): mp 198-200° C. $^1$H NMR (DMSO-$d_6$) δ 10.97 (br s, 2H), 10.67 (br s, 2H), 8.51 (br s, 1H), 8.08 (d, J=9.0 Hz, 2H), 8.00 (dd, J=8.2, 1.6 Hz, 1H), 7.91 (d, J=8.2 Hz, 1H), 7.68 (s, 1H), 7.58 (d, J=7.7 Hz, 1H), 7.51 (m, 1H), 7.47 (dd, J=8.2, 7.7 Hz, 1H), 7.20 (d, J=9.0 Hz, 2H), 7.08 (dd, J=8.2, 1.6 Hz, 1H), 4.25-4.15 (m, 4H), 4.03 (s, 4H), 3.94 (s, 4H), 2.05-1.85 (m, 4H). HPLC (method A) $t_R$ 8.55 min (100.0 area %). Anal. ($C_{30}H_{30}N_4O_3 \cdot 2HCl \cdot 0.8H_2O$) C, H, N, Cl.

2-(3-(5-(4-Carbamimidoylphenoxy)pentyloxy)phenyl)benzofuran-6-carboxamidine dihydrochloride (62). White solid (0.17 g, 27%): mp 178-182° C. $^1$H NMR (DMSO-$d_6$) δ 9.48 (br s, 2H), 9.26 (br s, 4H), 9.04 (br s, 2H), 8.22 (br s, 1H), 7.88 (d, J=8.2 Hz, 1H), 7.85 (d, J=8.8 Hz, 2H), 7.77 (dd, J=8.2, 1.6 Hz, 1H), 7.68 (s, 1H), 7.57 (d, J=7.7 Hz, 1H), 7.53 (m, 1H), 7.47 (dd, J=8.2, 7.7 Hz, 1H), 7.17 (d, J=8.8 Hz, 2H), 7.06 (dd, J=8.2, 1.6 Hz, 1H), 4.20-4.05 (m, 4H), 1.95-1.75 (m, 4H), 1.70-1.55 (m, 2H). HPLC (method A) $t_R$ 8.59 min (100.0 area %). Anal. ($C_{27}H_{28}N_4O_3 \cdot 2HCl \cdot 0.5$ EtOH $\cdot 0.4H_2O$) C, H, N, Cl.

2-(3-(5-(4-(N-Isopropylcarbamimidoyl)phenoxy)pentyloxy)phenyl)-N-isopropylbenzofuran-6-carboxamidine dihydrochloride (63). White solid (0.26 g, 35%): mp 253-255° C. $^1$H NMR (DMSO-$d_6$) δ 9.67 (d, J=7.7 Hz, 1H), 9.57 (br s, 1H), 9.43 (d, J=8.2 Hz, 1H), 9.34 (br s, 1H), 9.25 (br s, 1H), 9.03 (br s, 1H), 8.12 (br s, 1H), 7.86 (d, J=8.2 Hz, 1H), 7.73 (d, J=8.8 Hz, 2H), 7.67 (s, 1H), 7.65 (d, J=8.2 Hz, 1H), 7.56 (d, J=7.7 Hz, 1H), 7.52 (br s, 1H), 7.46 (dd, J=7.7, 7.7 Hz, 1H), 7.14 (d, J=8.8 Hz, 2H), 7.06 (d, J=7.7, 1.6 Hz, 1H), 4.25-4.00 (m, 6H), 1.95-1.75 (m, 4H), 1.70-1.55 (m, 2H), 1.31 (d, J=6.3 Hz, 6H), 1.26 (d, J=6.3 Hz, 6H). HPLC (method A) $t_R$ 9.59 min (100.0 area %). Anal. ($C_{33}H_{40}N_4O_3 \cdot 2HCl \cdot 0.5H_2O$) C, H, N, Cl.

2-(2-(3-(5-(4-(4,5-Dihydro-1H-imidazol-2-yl)phenoxy)pentyloxy)phenyl)benzofuran-6-yl)-4,5-dihydro-1H-imidazole dihydrochloride (64). White solid (0.30 g, 44%): mp 188-190° C. $^1$H NMR (DMSO-$d_6$) δ 10.66 (br s, 2H), 10.42 (br s, 2H), 8.37 (br s, 1H), 7.96 (d, J=9.3 Hz, 2H), 7.93 (d, J=8.2 Hz, 1H), 7.90 (dd, J=8.2, 1.6 Hz, 1H), 7.69 (s, 1H), 7.58 (d, J=8.2 Hz, 1H), 7.53 (m, 1H), 7.47 (dd, J=8.2, 8.2 Hz, 1H), 7.21 (d, J=9.3 Hz, 2H), 7.07 (dd, J=8.2, 2.2 Hz, 1H), 4.20-4.10 (m, 4H), 4.04 (s, 4H), 3.96 (s, 4H), 1.95-1.75 (m, 4H), 1.70-1.55 (m, 2H). HPLC (method A) $t_R$ 8.95 min (100.0 area %). Anal. ($C_{31}H_{32}N_4O_3 \cdot 2HCl \cdot 0.7H_2O$) C, H, N, Cl.

2-(3-(6-(4-Carbamimidoylphenoxy)hexyloxy)phenyl)benzofuran-6-carboxamidine dihydrochloride (65). White solid (0.20 g, 38%): mp 268-271° C. $^1$H NMR (DMSO-$d_6$) δ 9.45 (br s, 2H), 9.29 (br s, 2H), 9.27 (br s, 2H), 9.07 (br s, 2H), 8.23 (br s, 1H), 7.88 (d, J=8.2 Hz, 1H), 7.86 (d, J=9.3 Hz, 2H), 7.77 (dd, J=8.2, 1.6 Hz, 1H), 7.67 (s, 1H), 7.57 (d, J=7.7 Hz, 1H), 7.52 (m, 1H), 7.46 (dd, J=8.2, 7.7 Hz, 1H), 7.16 (d, J=9.3 Hz, 2H), 7.06 (dd, J=8.2, 1.6 Hz, 1H), 4.20-4.05 (m, 4H), 1.95-1.75 (m, 4H), 1.70-1.50 (m, 4H). HPLC (method A) $t_R$ 8.88 min (99.05 area %). Anal. ($C_{28}H_{30}N_4O_3 \cdot 2HCl \cdot 0.2H_2O$) C, H, N, Cl.

2-(3-(6-(4-(N-Isopropylcarbamimidoyl)phenoxy)hexyloxy)phenyl)-N-isopropylbenzofuran-6-carboxamidine dihydrochloride (66). White solid (0.13 g, 21%): mp 283-285° C. $^1$H NMR (DMSO-$d_6$) δ 9.37 (br s, 1H), 9.53 (br s, 6H), 8.11 (br s, 1H), 7.86 (d, J=8.2 Hz, 1H), 7.72 (d, J=8.9 Hz, 2H), 7.67 (s, 1H), 7.65 (dd, J=8.2, 1.6 Hz, 1H), 7.56 (d, J=7.7 Hz, 1H), 7.51 (m, 1H), 7.46 (dd, J=8.2, 7.7 Hz, 1H), 7.14 (d, J=8.9 Hz, 2H), 7.05 (dd, J=8.2, 1.6 Hz, 1H), 4.25-4.00 (m, 6H), 1.90-1.70 (m, 4H), 1.65-1.45 (m, 4H), 1.30 (d, J=6.4 Hz, 6H), 1.26 (d, J=6.4 Hz, 6H). HPLC (method A) $t_R$ 9.91 min (100.0 area %). Anal. ($C_{34}H_{42}N_4O_3 \cdot 2HCl \cdot 1H_2O$) C, H, N, Cl.

2-(2-(3-(6-(4-(4,5-Dihydro-1H-imidazol-2-yl)phenoxy)hexyloxy)phenyl)benzofuran-6-yl)-4,5-dihydro-1H-imidazole dihydrochloride (67). White solid (0.31 g, 55%): mp 182-186° C. $^1$H NMR (DMSO-$d_6$) δ 10.77 (br s, 4H), 8.49 (br s, 1H), 8.05 (d, J=8.8 Hz, 2H), 7.98 (dd, J=8.2, 1.6 Hz, 1H), 7.91 (d, J=8.2 Hz, 1H), 7.69 (s, 1H), 7.57 (d, J=7.7 Hz, 1H), 7.52 (m, 1H), 7.46 (dd, J=8.2, 7.7 Hz, 1H), 7.18 (d, J=8.8 Hz, 2H), 7.06 (dd, J=8.2, 1.6 Hz, 1H), 4.20-4.05 (m, 4H), 4.03 (s, 4H), 3.95 (s, 4H), 1.85-1.70 (m, 4H), 1.65-1.45 (m, 4H). HPLC (method A) $t_R$ 9.26 min (100.0 area %). Anal. ($C_{32}H_{34}N_4O_3 \cdot 2HCl \cdot 1H_2O$) C, H, N, Cl.

2-(4-(3-(4-Carbamimidoylphenoxy)propoxy)phenyl)benzofuran-6-carboxamidine dihydrochloride (68). White solid (0.24 g, 43%): mp 294-295° C. $^1$H NMR (DMSO-$d_6$) δ 9.47 (br s, 2H), 9.29 (br s, 2H), 9.26 (br s, 2H), 9.09 (br s, 2H), 8.20 (br s, 1H), 7.93 (d, J=8.8 Hz, 2H), 7.88 (d, J=8.8 Hz, 2H), 7.84 (d, J=8.2 Hz, 1H), 7.75 (dd, J=8.2, 1.6 Hz, 1H), 7.47 (s, 1H), 7.20 (d, J=8.8 Hz, 2H), 7.15 (d, J=8.8 Hz, 2H), 4.35-4.15 (m, 4H), 2.35-2.15 (m, 2H). HPLC (method A) $t_R$ 7.85 min (100.0 area %). Anal. ($C_{25}H_{24}N_4O_3 \cdot 2HCl \cdot 0.7H_2O$) C, H, N, Cl.

2-(4-(3-(4-(N-Isopropylcarbamimidoyl)phenoxy)propoxy)phenyl)-N-isopropylbenzofuran-6-carboxamidine dihydrochloride (69). White solid (0.25 g, 27%): mp 266-270° C. $^1$H NMR (DMSO-$d_6$) δ 9.64 (d, J=7.7 Hz, 1H), 9.54 (br s, 1H), 9.45 (d, J=8.2 Hz, 1H), 9.36 (br s, 1H), 9.22 (br s, 1H), 9.05 (br s, 1H), 8.08 (br s, 1H), 7.92 (d, J=8.8 Hz, 2H), 7.81 (d, J=8.2 Hz, 1H), 8.75 (d, J=8.8 Hz, 2H), 7.63 (dd, J=8.2, 1.6 Hz, 1H), 7.46 (s, 1H), 7.18 (d, J=8.8 Hz, 2H), 7.15 (d, J=8.8 Hz, 2H), 4.35-4.20 (m, 4H), 4.20-4.00 (m, 2H), 1.30 (d, J=6.3 Hz, 6H), 1.26 (d, J=6.3 Hz, 6H). HPLC (method A) $t_R$ 8.92 min (100.0 area %). Anal. ($C_{31}H_{36}N_4O_3 \cdot 2HCl$) C, H, N, Cl.

2-(2-(4-(3-(4-(4,5-Dihydro-1H-imidazol-2-yl)phenoxy)propoxy)phenyl)benzofuran-6-yl)-4,5-dihydro-1H-imidazole dihydrochloride (70). White solid (0.34 g, 38%): mp 283-284° C. $^1$H NMR (DMSO-$d_6$) δ 10.91 (br s, 2H), 10.67 (br s, 2H), 8.47 (br s, 1H), 8.08 (d, J=8.8 Hz, 2H), 7.97 (dd, J=8.2, 1.6 Hz, 1H), 7.95 (d, J=8.8 Hz, 2H), 7.86 (d, J=8.2 Hz, 2H), 7.49 (s, 1H), 7.24 (d, J=8.8 Hz, 2H), 7.15 (d, J=8.8 Hz, 2H), 4.35-4.20 (m, 4H), 4.02 (s, 4H), 3.96 (s, 4H), 2.35-2.20 (m, 2H). HPLC (method A) $t_R$ 8.22 min (100.0 area %). Anal. ($C_{29}H_{28}N_4O_3 \cdot 2HCl \cdot 1H_2O$) C, H, N, Cl.

2-(4-(4-(4-Carbamimidoylphenoxy)butoxy)phenyl)benzofuran-6-carboxamidine dihydrochloride (71). White solid (0.37 g, 64%): mp 324-325° C. $^1$H NMR (DMSO-$d_6$) δ 9.46 (br s, 2H), 9.28 (br s, 2H), 9.25 (br s, 2H), 9.08 (br s, 2H), 8.20 (br s, 1H), 7.92 (d, J=8.8 Hz, 2H), 7.87 (d, J=8.8 Hz, 2H), 7.85 (d, J=8.2 Hz, 1H), 7.74 (dd, J=8.2, 1.6 Hz, 1H), 7.47 (s, 1H), 7.17 (d, J=8.8 Hz, 2H), 7.13 (d, J=8.8 Hz, 2H), 4.35-4.05 (m, 4H), 2.10-1.80 (m, 4H). HPLC (method A) $t_R$ 8.16 min (100.0 area %). Anal. ($C_{26}H_{26}N_4O_3 \cdot 2HCl \cdot 0.2Et_2O$) C, H, N, Cl.

2-(4-(4-(4-(N-Isopropylcarbamimidoyl)phenoxy)butoxy) phenyl)-N-isopropylbenzofuran-6-carboxamidine dihydrochloride (72). White solid (0.28 g, 42%): mp 280-283° C. $^1$H NMR (DMSO-d$_6$) δ9.63 (d, J=7.7 Hz, 1H), 9.54 (br s, 1H), 9.44 (d, J=8.8 Hz, 1H), 9.36 (br s, 1H), 9.22 (br s, 1H), 9.05 (br s, 1H), 8.08 (br s, 1H), 7.92 (d, J=8.8 Hz, 2H), 7.82 (d, J=8.2 Hz, 1H), 8.74 (d, J=8.8 Hz, 2H), 7.63 (dd, J=8.2, 1.1 Hz, 1H), 7.46 (s, 1H), 7.15 (d, J=8.8 Hz, 2H), 7.13 (d, J=8.8 Hz, 2H), 4.30-3.95 (m, 6H), 2.00-1.85 (m, 4H), 1.31 (d, J=6.4 Hz, 6H), 1.27 (d, J=6.4 Hz, 6H). HPLC (method A) t$_R$ 9.25 min (100.0 area %). Anal. (C$_{32}$H$_{38}$N$_4$O$_3$.2HCl.0.4 EtOH) C, H, N, Cl.

2-(2-(4-(4-(4-(4,5-Dihydro-1H-imidazol-2-yl)phenoxy) butoxy)phenyl)benzofuran-6-yl)-4,5-dihydro-1H-imidazole dihydrochloride (73). White solid (0.42 g, 70%): mp 306-307° C. $^1$H NMR (DMSO-d$_6$) δ10.67 (br s, 2H), 10.45 (br s, 2H), 8.36 (s, 1H), 7.99 (d, J=9.3 Hz, 2H), 7.94 (d, J=8.8 Hz, 2H), 7.88 (br s, 2H), 7.49 (s, 1H), 7.22 (d, J=9.3 Hz, 2H), 7.13 (d, J=8.8 Hz, 2H), 4.25-4.10 (m, 4H), 4.04 (s, 4H), 3.97 (s, 4H), 2.00-1.85 (m, 4H). HPLC (method A) t$_R$ 8.58 min (100.0 area %). Anal. (C$_{30}$H$_{30}$N$_4$O$_3$.2HCl.1H$_2$O) C, H, N, Cl.

2-(4-(5-(4-Carbamimidoylphenoxy)pentyloxy)phenyl) benzofuran-6-carboxamidine dihydrochloride (74). White solid (0.06 g, 10%): mp 285° C. (dec). $^1$H NMR (DMSO-d$_6$) δ9.44 (br s, 2H), 9.25 (br s, 2H), 9.22 (br s, 2H), 9.04 (br s, 2H), 8.19 (br s, 1H), 7.92 (d, J=8.8 Hz, 2H), 7.86 (d, J=8.8 Hz, 2H), 7.85 (d, J=8.2 Hz, 1H), 7.74 (dd, J=8.2, 1.6 Hz, 1H), 7.46 (s, 1H), 7.16 (d, J=8.8 Hz, 2H), 7.12 (d, J=8.8 Hz, 2H), 4.20-4.00 (m, 4H), 1.90-1.75 (m, 4H), 1.70-1.50 (m, 2H). HPLC (method A) t$_R$ 8.53 min (100.0 area %). Anal. (C$_{27}$H$_{28}$N$_4$O$_3$.2HCl.0.6EtOH.0.8H$_2$O) C, H, N, Cl.

2-(4-(5-(4-(N-Isopropylcarbamimidoyl)phenoxy)pentyloxy)phenyl)-N-isopropylbenzofuran-6-carboxamidine dihydrochloride (75). White solid (0.43 g, 61%): mp 255-257° C. $^1$H NMR (DMSO-d$_6$) δ9.63 (d, J=8.8 Hz, 1H), 9.54 (br s, 1H), 9.44 (d, J=8.8 Hz, 1H), 9.35 (br s, 1H), 9.22 (br s, 1H), 9.05 (br s, 1H), 8.08 (br s, 1H), 7.91 (d, J=8.8 Hz, 2H), 7.81 (d, J=8.2 Hz, 1H), 8.73 (d, J=8.8 Hz, 2H), 7.63 (dd, J=8.2, 1.6 Hz, 1H), 7.45 (s, 1H), 7.13 (d, J=8.8 Hz, 2H), 7.12 (d, J=8.8 Hz, 2H), 4.30-3.95 (m, 6H), 1.90-1.75 (m, 4H), 1.70-1.50 (m, 2H), 1.31 (d, J=6.3 Hz, 6H), 1.27 (d, J=6.3 Hz, 6H). HPLC (method A) t$_R$ 9.58 min (100.0 area %). Anal. (C$_{33}$H$_{40}$N$_4$O$_3$.2HCl.0.3H$_2$O) C, H, N, Cl.

2-(2-(4-(5-(4-(4,5-Dihydro-1H-imidazol-2-yl)phenoxy) pentyloxy)phenyl)benzofuran-6-yl)-4,5-dihydro-1H-imidazole dihydrochloride (76). White solid (0.45 g, 69%): mp 212-215° C. $^1$H NMR (DMSO-d$_6$) δ10.59 (br s, 2H), 10.38 (br s, 2H), 8.31 (br s, 1H), 7.95 (d, J=8.8 Hz, 2H), 7.94 (d, J=8.8 Hz, 1H), 7.88-7.85 (m, 2H), 7.48 (s, 1H), 7.21 (d, J=8.8 Hz, 2H), 7.10 (d, J=8.8 Hz, 2H), 4.20-4.05 (m, 4H), 4.04 (s, 4H), 3.97 (s, 4H), 1.90-1.75 (m, 4H), 1.70-1.50 (m, 2H). HPLC (method A) t$_R$ 8.93 min (100.0 area %). Anal. (C$_{31}$H$_{32}$N$_4$O$_3$.2HCl.0.7H$_2$O) C, H, N, Cl.

2(4-(6-(4-Carbamimidoylphenoxy)hexyloxy)phenyl)benzofuran-6-carboxamidine dihydrochloride (77). White solid (0.06 g, 14%): mp 310-311° C. $^1$H NMR (DMSO-d$_6$) δ9.22 (br s, 8H), 8.18 (br s, 1H), 7.92 (d, J=8.8 Hz, 2H), 7.84 (d, J=8.8 Hz, 2H), 7.84 (d, J=8.2 Hz, 1H), 7.73 (dd, J=8.2 and 1.6 Hz, 1H), 7.46 (s, 1H), 7.16 (d, J=8.8 Hz, 2H), 7.11 (d, J=8.8 Hz, 2H), 4.20-3.95 (m, 4H), 1.90-1.70 (m, 4H), 1.65-1.45 (m, 4H). HPLC (method A) t$_R$ 8.90 min (100.0 area %). Anal. (C$_{28}$H$_{30}$N$_4$O$_3$.2HCl.0.7EtOH.0.6H$_2$O) C, H, N, Cl.

2-(4-(6-(4-(N-Isopropylcarbamimidoyl)phenoxy)hexyloxy)phenyl)-N-isopropylbenzofuran-6-carboxamidine dihydrochloride (78). White solid (0.23 g, 54%): mp 264-268° C. $^1$H NMR (DMSO-d$_6$) δ9.61 (d, J=8.5 Hz, 1H), 9.52 (br s, 1H), 9.41 (d, J=8.3 Hz, 1H), 9.33 (br s, 1H), 9.18 (br s, 1H), 9.00 (br s, 1H), 8.07 (br s, 1H), 7.91 (d, J=8.8 Hz, 2H), 7.82 (d, J=8.2 Hz, 1H), 8.72 (d, J=8.8 Hz, 2H), 7.63 (dd, J=8.2, 1.6 Hz, 1H), 7.46 (s, 1H), 7.13 (d, J=8.8 Hz, 2H), 7.12 (d, J=8.8 Hz, 2H), 4.25-4.00 (m, 6H), 1.90-1.70 (m, 4H), 1.65-1.40 (m, 4H), 1.30 (d, J=6.4 Hz, 6H), 1.26 (d, J=6.4 Hz, 6H). HPLC (method A) t$_R$ 9.90 min (100.0 area %). Anal. (C$_{34}$H$_{42}$N$_4$O$_3$.2HCl.0.3H$_2$O) C, H, N, Cl.

2-(2-(4-(6-(4-(4,5-Dihydro-1H-imidazol-2-yl)phenoxy) hexyloxy)phenyl)benzofuran-6-yl)-4,5-dihydro-1H-imidazole dihydrochloride (79). White solid (0.26 g, 63%): mp 265-269° C. $^1$H NMR (DMSO-d$_6$) δ10.62 (br s, 4H), 8.45 (br s, 1H), 8.05 (d, J=8.8 Hz, 2H), 7.96 (dd, J=8.2, 1.6 Hz, 1H), 7.94 (d, J=8.8 Hz, 2H), 7.86 (d, J=8.2 Hz, 1H), 7.48 (s, 1H), 7.18 (d, J=8.8 Hz, 2H), 7.10 (d, J=8.8 Hz, 2H), 4.25-4.05 (m, 4H), 4.02 (s, 4H), 3.95 (s, 4H), 1.90-1.70 (m, 4H), 1.60-1.40 (m, 4H). HPLC (method A) t$_R$ 9.28 min (100.0 area %). Anal. (C$_{32}$H$_{34}$N$_4$O$_3$.2HCl.0.8H$_2$O) C, H, N, Cl.

General Procedure for Synthesis of Bis-benzofuranmethanones (82, 83)

Bis(4-bromobenzofuran-2-yl)methanone (82). Dried K$_2$CO$_3$ (7g, 50.1 mmol) was added to a solution of 2-bromo-6-hydroxybenzaldehyde (80) (6.57 g, 32.3 mmol) in dry butanone (35 mL). The suspension was refluxed for 30 min and cooled to room temperature. A solution of 1,3-dichloroacetone (3 g, 24.23 mmol) in 5 mL of dry butanone was added. The reaction mixture was refluxed for 4 hours, cooled down, filtered through a pad of Celite (2 cm) and concentrated. A dark residue was recrystallized from CHCl$_3$ to give 82 as brown solid (5.05 g, 76%): mp 223-225° C. $^1$H NMR (DMSO-d$_6$) δ8.10 (s, 2H), 7.92 (d, J=8.2 Hz, 2H), 7.70 (d, J=7.7 Hz, 2H), 7.57 (dd, J=8.2, 7.7 Hz, 2H). HPLC (method B) t$_R$ 9.83 min (100.00 area %). Anal. (C$_{17}$H$_8$Br$_2$O$_3$) C, H, Br.

Bis(6-bromobenzofuran-2-yl)methanone (83). Following the procedure described above for 82, 83 was prepared from 81 and 1,3-dichloroacetone as dark yellow solid (2.16 g, 76%): mp 176-177° C. (CH$_2$Cl$_2$). $^1$H NMR (DMSO-d$_6$) δ8.26 (s, 2H), 8.17 (br s, 2H), 7.87 (d, J=8.8 Hz, 2H), 7.61 (dd, J=8.7, 1.6 Hz, 2H). HPLC (method B) t$_R$ 9.62 min (100.00 area %). Anal. (C$_{17}$H$_8$Br$_2$O$_3$) C, H, Br.

General Procedure for Synthesis of Bis-benzofuranmethanes (84, 85)

Bis(4-bromobenzofuran-2-yl)methane (84). A solution of aluminum chloride (4.8 g, 11.43 mmol) in dry diethyl ether (70 mL) was added dropwise under Ar to a stirred suspension of lithium aluminum hydride (0.98 g, 25.78 mmol) in dry diethyl ether (100 mL). Pre-dried under high vacuum 82 (4.8 g, 11.43 mmol) was added in small portions. The reaction mixture was stirred at room temperature for 1 hour followed by careful addition of 2 M HCl (100 mL) and extraction with diethyl ether (2×100 mL). The ether solution was dried over CaCl$_2$ and concentrated to provide 84 product as white crystals (3.84 g, 83%): mp 142-143° C. (diethyl ether). $^1$H NMR (DMSO-d$_6$) δ7.60 (d, J=8.2 Hz, 2H), 7.47 (d, J=7.7 Hz, 2H), 7.24 (dd, J=8.2, 7.7 Hz, 2H), 6.80 (s, 2H), 4.52 (s, 2H). HPLC (method B) t$_R$ 10.67 min (100.00 area %). Anal. (C$_{17}$H$_{10}$Br$_2$O$_3$) C, H, Br.

Bis(6-bromobenzofuran-2-yl)methane (85). Following the procedure described above for 84, 85 was prepared from 83 as white crystals (1.43 g, 99%): mp 146-147° C. (diethyl ether). $^1$H NMR (DMSO-d$_6$) δ7.85 (br s, 2H), 7.55 (d, J=8.2 Hz, 2H), 7.39 (dd, J=8.2, 1.6 Hz, 2H), 6.82 (s, 2H), 4.44 (s, 2H). HPLC (method B) t$_R$ 10.43 min (100.00 area %). Anal. (C$_{17}$H$_{10}$Br$_2$O$_3$) C, H, Br.

General Procedure for Synthesis of Bis-benzofuranmethane Carbodinitriles (86, 87)

2-((5-Cyanobenzofuran-2-yl)methyl)benzofuran-5-carbonitrile (86). A mixture of bis(6-bromobenzofuran-2-yl) methanone (84) (3.50 g, 8.62 mmol) and CuCN (6.12 g, 69.0 mmol) was heated under reflux in dry quinoline (10 mL) for 2 hours. The hot reaction mixture was poured into 2 M HCl solution and resulting mixture was stirred at 50-70° C. for 1 hour. Olive precipitate was filtered off, dried under high vacuum and suspended into 300 mL chlorobenzene. The mixture was stirred for 1 hour at room temperature, insoluble material was separated, and filtrate was concentrated. A dark solid residue (2 g, 78%) was purified by column chromatography ($SiO_2$, $CHCl_3$) to afford desired product as light yellow crystals (1.62 g, 63%): mp 173-174° C. ($CHCl_3$). $^1$H NMR (DMSO-$d_6$) δ7.96 (d, J=8.2 Hz, 2H), 7.77 (d, J=7.7 Hz, 2H), 7.46 (tt, J=8.2, 7.7 Hz, 2H), 7.09 (s, 2H), 4.64 (s, 2H). HPLC (method B) $t_R$ 7.92 min (100.00 area %). Anal. ($C_{19}H_{10}N_2O_2$) C, H, N.

2-((6-Cyanobenzofuran-2-yl)methyl)benzofuran-6-carbonitrile (87). Following the procedure described above for 86, 87 was prepared from 85 as light yellow crystals (0.55 g, 56%): mp 207-209° C. ($CHCl_3$). $^1$H NMR (DMSO-$d_6$) δ8.19 (s, 2H), 7.80 (d, J=8.2 Hz, 2H), 7.66 (d, J=8.2 Hz, 2H), 7.00 (s, 2H), 4.61 (s, 2H). HPLC (method B) $t_R$ 7.92 min (96.90 area %). Anal. ($C_{19}H_{10}N_2O_2 \cdot 0.3H_2O$) C, H, N.

General Procedure for Synthesis of Benzofuran Under Castro Conditions

Methyl 2-(3-hydroxypropyl)benzofuran-5-carboxylate (95). See Fancelli D.; Fagnola, M. C.; Bedeschi, A. Solid phase Synthesis of 2-Substituted Benzofurans via the Palladium-catalyzed Heteroannulation of acetylenes. *Tetrahedron Letters* 1997, 38, 2311-2314. A mixture of methyl 4-hydroxy-3-iodobenzoate (93) (35 g, 125.9 mmol), 4-pentyn-1-ol (11.00 g, 130.7 mmol) and copper (I) oxide (12.62 g, 88.2 mmol) in dyr pyridine (150 mL) was stirred at 100-120° C. overnight. The mixture was allowed to cool to room temperature, diluted with EtOAc (200 mL), filtered through a Celite pad (5 cm) and concentrated. The residue was dissolved in EtOAc (300 mL), washed with 2 M HCl (50 mL), brine (100 mL), dried over $Na_2SO_4$, filtered and concentrated. Column chromatography ($SiO_2$, EtOAc/hexanes, 1/1) followed by recrystallization (hexanes/diethyl ether, 2/1) afforded 95 as light yellow crystals (14.39 g, 49%). $^1$H NMR (DMSO-$d_6$) δ8.20 (s, 1H), 7.86 (d, J=8.2 Hz, 1H), 7.13 (d, J=8.2 Hz, 1H), 6.74 (s, 1H), 4.59 (b, 1H), 3.49 (b, 2H), 3.86 (s, 3H), 2.84 (t, J=7.1 Hz, 2H), 1.85 (m, 2H). HPLC (method B) $t_R$ 4.20 min (100.00 area %).

Methyl 2-(3-hydroxyproply)benzofuran-6-carboxylate (96). Following the procedure described above for 95, 96 was prepared from 94 and 4-pentyn-1-ol as a light yellow solid (10.8 g, 66%): mp 63-65° C. (EtOAc/hexanes). $^1$H NMR (DMSO-$d_6$) δ8.04 (s, 1H), 7.83 (d, J=8.2 Hz, 1H), 7.65 (d, J=8.2 Hz, 1H), 6.74 (s, 1H), 4.59 (b, 1H), 3.87 (s, 3H), 3.49 (t, J=6.0 Hz, 2H), 2.86 (t, J=7.7 Hz, 2H), 1.85 (m, 2H). HPLC (method B) $t_R$ 4.17 min (96.54 area %). Anal. ($C_{13}H_{14}O_4 \cdot 0.1H_2O$) C, H.

Methyl 2-(2-formylethyl)benzofuran-5-carboxylate (97). Oxalyl chloride (2 M solution in $CH_2Cl_2$, 40 mL, 80 mmol) was placed under Ar into a reaction flask, equipped with addition funnel, inlet thermometer and drying tube charged with Drierite, and cooled to −70° C. A mixture of DMSO (12.2 mL, 171.2 mmol) and dry $CH_2Cl_2$ (30 mL) was added dropwise. After 30 min a solution of 95 (14.3 g, 61 mmol) in $CH_2Cl_2$ was slowly added and the mixture was stirred at −70° C. for 60 min. After that time triethylamine (45.2 mL, 405 mmol) was added dropwise at −60° C. The mixture was allowed to warm to room temperature, water (100 mL) was added carefully and the stirring continued for 10 min. Organic layer was separated and the aqueous layer was extracted with $CH_2Cl_2$ (2×75 mL). Combined organic were washed with 2 M HCl (30 mL), dried over $Na_2SO_4$ and concentrated. Column chromatography ($SiO_2$, EtOAc/hexanes, 5/1) followed by recrystalliztion (EtOAc/hexanes, 1/3) afforded 97 as light yellow crystals (12.93 g, 91%): mp. 48-49° C. $^1$H NMR (DMSO-$d_6$) δ9.70 (s, 1H), 8.20 (s, 1H), 7.87 (d, J=8.2 Hz, 1H), 7.62 (d, J=8.2 Hz, 1H), 6.75 (s, 1H), 3.87 (s, 3H), 3.07 (m, 2H), 2.96 (m, 2H). Anal. ($C_{13}H_{12}O_4 \cdot 0.1H_2O$) C, H.

Methyl 2-(2-formylethyl)benzofuran-6-carboxylate (98). Following the procedure described above for 97, 98 was prepared from 96 as a light yellow solid (2.78 g, 85%): mp 57-58° C. (EtOAc/hexanes). $^1$H NMR (DMSO-$d_6$) δ9.76 (s, 1H), 8.04 (s, 1H), 7.83 (d, J=8.2 Hz, 1H), 7.66 (d, J=8.2 Hz, 1H), 6.75 (s, 1H), 3.87 (s, 3H), 3.09 (m, 2H), 2.95 (m, 2H). Anal. ($C_{13}H_{12}O_4$) C, H.

Methyl 2-(but-3-ynyl)benzofuran-5-carboxylate (99). See Callant, P. D. H. L.; Vandewalle, M. An efficient preparation and the intramoleucalur cyclopropanation of a-diazo-b-ketophosphonates and a-diazophoshonoacetates. *Snyth. Commun.* 1984, 14, 155-161. A solution of dimethyl-1-diazo-2-oxopropylphosphonate (8.9 g, 46.4 mmol) in dry methanol (50 mL) was added to a stirring mixture of 97 (8.5 g, 36.6 mmol) and $K_2CO_3$ (10.2 g, 74 mmol) in 500 mL of dry methanol. The mixture was stirred at room temperature until complete conversion was attained according to HPLC (2 hours) and concentrated. The residue was diluted with diethyl ether (500 mL), washed with water (2×100 mL) and dried over $CaCl_2$. The solvent was removed following by recrystallization (EtOAc/hexanes, 9/1) to give white crystals (7.66 g, 92%): mp 57-58° C. $^1$H NMR (DMSO-$d_6$) δ8.23 (d, J=1.6 Hz, 1H), 7.88 (dd, J=8.8, 1.6 Hz, 1H), 7.63 (d, J=8.8 Hz, 1H), 6.82 (s, 1H), 3.86 (s, 3H), 3.00 (t, J=7.1 Hz, 2H), 2.84 (t, J=2.8 Hz, 1H), 2.63 (td, J=7.1, 2.8 Hz, 2H). HPLC (method B) $t_R$ 6.73 min (100.00 area %). Anal. ($C_{14}H_{12}O_3 \cdot 0.2H_2O$) C, H.

Methyl 2-(but-3-ynyl)benzofuran-6-carboxylate (100). Following the procedure described above for 99, 100 was prepared from 98 as a white solid (0.40 g, 98%): mp 68-69° C. (EtOAc/hexanes). $^1$H NMR (DMSO-$d_6$) δ8.05 (d, J=1.1 Hz, 1H), 7.88 (dd, J=8.2, 1.1 Hz, 1H), 7.64 (d, J=8.2 Hz, 1H), 6.83 (s, 1H), 3.87 (s, 3H), 3.02 (t, J=7.1 Hz, 2H), 2.86 (t, J=2.8 Hz, 1H), 2.63 (td, J=7.1, 2.8 Hz, 2H). HPLC (method B) $t_R$ 6.71 min (97.60 area %). Anal. ($C_{14}H_{12}O_3 \cdot 0.1H_2O$) C, H.

Methyl 2-(2-(5-(methoxycarbonyl)benzofuran-2-yl)ethyl)benzofuran-5-carboxylate (101). Following the procedure described above for 95, 101 was prepared from 93 and 99 as white solid (5.24 g, 43%): mp 165-167° C. (EtOAc/hexanes). $^1$H NMR (DMSO-$d_6$) δ8.20 (s, 2H), 7.87 (d, J=8.8 Hz, 2H), 7.63 (d, J=8.8 Hz, 2H), 6.82 (s, 2H), 3.86 (s, 6H), 3.34 (s, 4H). Anal. ($C_{22}H_{18}O_6 \cdot 0.8H_2O$) C, H.

Methyl 2-(2-(6-(methoxycarbonyl)benzofuran-2-yl)ethyl)benzofuran-6-carboxylate (102). Following the procedure described above for 95, 101 was prepared from 94 to 100 as a white solid (0.6 g, 24%): mp 175-177° C. ($CH_2Cl_2$). $^1$H NMR (DMSO-$d_6$) δ8.04 (b, 2H), 7.83 (dd, J=8.2, 1.1 Hz, 2H), 7.65 (d, J=8.2 Hz, 2H), 6.83 (s, 2H), 3.87 (s, 6H), 3.33 (s, 4H). HPLC (method B) $t_R$ 9.16 min (100.00 area %). Anal. ($C_{22}H_{18}O_6$) C, H.

General Procedure for Synthesis of Bis-benzofuran Carbodinitriles (103-124)

2-(2-(5-Cyanobenzofuran-2-yl)ethyl)benzofuran-5-carbonitrile (103). See Dann, O.; Volz, G.; Demant, E.; Pfeifer, W.; Bergen, G.; Fick, H.; Walkenhorst, E.; Trypanocide Diamidine mit vier Ringen in einem oder zwei Ringsystemen. *Liebigs Ann. Chem.* 1973, 1112-1140. Anhydrous $NH_3$ was bubbled through dry o-xylene (100 mL) for 20 min at 0° C. A 2.0 M solution of $AlMe_3$ in toluene (27 mL, 54 mmol) was added and the $NH_3$ was passed through the mixture for 20 min and then the solution was stirred at room temperature for 1 hour. Methyl 2-(2-(5-(methoxycarbonyl)benzofuran-2-yl)ethyl)benzofuran-5-carboxylate (101) (5.0 g 13.2 mmol) was added in one portion. The mixture was kept for 3 hours at 100-110° C., allowed to cool to room temperature, diluted with $CHCl_3$ (250 mL), and water (100 mL) was added dropwise with vigorous stirring. Forming inorganic solids were filtered off. Organic filtrate was separated and concentrated to give crude 103 (4.0 g, 97%). Column chromatography ($SiO_2$, $CH_2Cl_2$) afforded desired product as light yellow crystals (1.96 g, 48%): mp 243-244° C. ($CH_2Cl_2$) (lit. 247.5-250° C.; Dann, O.; Volz, G.; Demant, E.; Pfeifer, W.; Bergen, G.; Fick, H.; Walkenhorst, E.; Trypanocide Diamidine mit vier Ringen in einem oder zwei Ringsystemen. *Liebigs Ann. Chem.* 1973, 1112-1140). $^1$H NMR (DMSO-$d_6$) δ8.10 (br s, 2H), 7.87 (d, J=8.2 Hz, 2H), 7.54 (dd, J=8.2, 1.6 Hz, 2H), 6.82 (s, 2H), 3.31 (s, 4H). HPLC (method B) $t_R$ 8.15 min (100.00 area %). Anal. ($C_{20}H_{12}N_2O_2$.0.6$H_2O$) C, H, N.

2-(2-(6-Cyanobenzofuran-2-yl)ethyl)benzofuran-6-carbonitrile (104). Following the procedure described above for 103, 104 was prepared from 102 as a light yellow solid (0.56 g, 27%): mp 266-267° C. ($CH_2Cl_2$) (lit. 272-274° C.; Dann, O.; Char, H.; Grießmeier, H.; Synthesen biskationischer, trypanocider 1-Benzofuran-Verbindungen. *Liebigs Ann. Chem.* 1982, 1836-1869). $^1$H NMR (DMSO-$d_6$) δ8.16 (s, 2H), 7.75 (d, J=8.2 Hz, 2H), 7.63 (d, J=8.2 Hz, 2H), 6.88 (s, 2H), 3.35 (s, 4H). HPLC (method B) $t_R$ 8.26 min (100.00 area %). Anal. ($C_{20}H_{12}N_2O_2$.0.1$H_2O$) C, H, N.

Methyl-b 2-(3-(5-(methoxycarbonyl)benzofuran-2-yl)propyl)benzofuran-5-carboxylate (105). Following the procedure described above for 95, 105 was prepared from 93 and 1,6-heptadiyne as a white solid (6.44 g, 40%): mp 87-88° C. (EtOAc/heaxanes). $^1$H NMR (DMSO-$d_6$) δ8.17 (d, J=1.6, 2H), 7.86 (dd, J=8.8, 1.6 Hz, 2H), 7.61 (d, J=8.8 Hz, 2H), 6.79 (s, 2H), 3.86 (s, 6H), 2.92 (t, J=7.1, 4H), 2.15 (m, 2H). HPLC (method B) $t_R$ 9.67 min (100.00 area %). Anal. ($C_{23}H_{20}O_6$.0.5$H_2O$) C, H.

Methyl-2-(3-(6-(methoxycarbonyl)benzofuran-2-yl)propyl)benzofuran-6-carboxylate (106). Following the procedure described above for 95, 106 was prepared from 94 and 1,6-heptadiyne as a white solid (6.10 g, 44%): mp 100-101° C. (benzene/hexanes). $^1$H NMR (DMSO-$d_6$) δ8.17 (s, 2H), 7.82 (d, J=8.2 Hz, 2H), 7.64 (d, J=8.2 Hz, 2H), 6.79 (s, 2H), 3.87 (s, 6H), 2.94 (t, J=7.1, 4H), 2.17 (m, 2H). HPLC (method B) $t_R$ 9.63 min (93.00 area %). Anal. ($C_{23}H_{20}O_6$) C, H.

Methyl 2-(4-(5-(methoxycarbonyl)benzofuran-2-yl)butyl)benzofuran-5-carboxylate (107). Following the procedure described above for 95, 107 was prepared from 93 and 1,7-octadiyne as a white solid (5.35 g, 67%): mp 130-131° C. (EtOAc/hexanes). $^1$H NMR (DMSO-$d_6$) δ8.19 (d, J=1.1 Hz, 2H), 7.86 (dd, J=8.8, 1.1 Hz, 2H), 7.61 (d, J=8.8 Hz, 2H), 6.75 (s, 2H), 3.86 (s, 6H), 2.88 (b, 4H), 1.80 (b, 4H). Anal. ($C_{24}H_{22}O_6$.0.6$H_2O$) C, H.

Methyl 2-(4-(6-(methoxycarbonyl)benzofuran-2-yl)butyl)benzofuran-6-carboxylate (108). Following the procedure described above for 95, 108 was prepared from 94 and 1,7-octadiyne as a white solid (3.25 g, 45%), mp 130-131° C. (EtOAc/hexanes). $^1$H NMR (DMSO-$d_6$) δ8.01 (b, 2H), 7.83 (dd, J=8.2, 1.1 Hz, 2H), 7.65 (d, J=8.2 Hz, 2H), 6.75 (s, 2H), 3.86 (s, 6H), 2.90 (m, 4H), 1.80 (m, 4H). HPLC (method B) $t_R$ 10.19 min (100.00 area %). Anal. ($C_{24}H_{22}O_6$) C, H.

Methyl-2-(5-(5-(methoxycarbonyl)benzofuran-2-yl)pentyl)benzofuran-5-carboxylate (109). Following the procedure described above for 95, 109 was prepared from 93 and 1,8-nonadiyne as a yellow solid (4.78 g, 56%), mp 83-85° C. (EtOH). $^1$H NMR (DMSO-$d_6$) δ8.16 (d, J=1.6 Hz, 2H), 7.84 (dd, J=8.8, 1.6 Hz, 2H), 7.59 (d, J=8.8 Hz, 2H), 6.71 (s, 2H), 3.86 (s, 6H), 2.81 (t, J=7.1, 4H), 1.76 (m, 4H), 1.43 (m, 2H). HPLC (method B) $t_R$ 10.79 min (100.00 area %). Anal. ($C_{25}H_{24}O_6$) C, H.

Methyl-2-(5-(6-(methoxycarbonyl)benzofuran-2-yl)pentyl)benzofuran-6-carboxylate (110). Following the procedure described above for 95, 110 was prepared from 94 and 1,8-nonadiyne as a yellow solid (6.2 g, 56%): mp 83-85° C. (EtOH). $^1$H NMR (DMSO-$d_6$) δ8.01 (s, 2H), 7.82 (d, J=8.2 Hz, 2H), 7.62 (d, J=8.2 Hz, 2H), 6.73 (s, 2H), 3.87 (s, 6H), 2.84 (t, J=7.1, 4H), 1.77 (m, 4H), 1.45 (m, 2H). HPLC (method B) $t_R$ 10.63 min (100.00 area %). Anal. ($C_{25}H_{24}O_6$) C, H.

2-(3-(5-Cyanobenzofuran-2-yl)propyl)benzofuran-5-carbonitrile (111). Following the procedure described above for 103, 111 was prepared from 105 as a white solid (2.47 g, 49%): mp 153-154° C. (EtOAc/hexanes). $^1$H NMR (DMSO-$d_6$) δ8.07 (d, J=1.6 Hz, 2H), 7.75 (d, J=8.8 Hz, 2H), 7.60 (dd, J=8.8, 1.6 Hz, 2H), 6.79 (s, 2H), 2.93 (t, J=7.1 Hz, 4H), 2.15 (p, J=7.1 Hz, 2H). HPLC (method B) $t_R$ 8.69 min (96.09 area %). Anal. ($C_{21}H_{14}N_2O_2$.0.2EtOAc) C, H, N.

2-(3-(6-Cyanobenzofuran-2-yl)propyl)benzofuran-6-carbonitrile (112). Following the procedure described above for 103, 112 was prepared from 106 as a white solid (2.92 g, 58%): mp 199-201° C. (EtOAc/hexanes). $^1$H NMR (DMSO-$d_6$) δ8.11 (s, 2H), 7.71 (d, J=7.7 Hz, 2H), 7.60 (d, J=7.7 Hz, 2H), 6.83 (s, 2H), 2.95 (t, J=7.7 Hz, 4H), 2.17 (p, J=7.7 Hz, 2H). HPLC (method B) $t_R$ 8.64 min (100.00 area %). Anal. ($C_{21}H_{14}N_2O_2$) C, H, N.

2-(4-(5-Cyanobenzofuran-2-yl)butyl)benzofuran-5-carbonitrile (113). See Dann, O.; Char, H.; Grießmeier, H.; Synthesen biskationischer, trypanocider 1-Benzofuran-Verbindungen. *Liebigs Ann. Chem.* 1982, 1836-1869. Following the procedure described above for 103, 113 was prepared from 107 as a white solid (1.42 g, 33%): mp 187-188° C. (EtOAc/hexanes) (lit. 190-192° C.). $^1$H NMR (DMSO-$d_6$) δ8.10 (s, 2H), 7.73 (d, J=8.2 Hz, 2H), 7.69 (d, J=8.2 Hz, 2H), 6.76 (s, 2H), 2.90 (m, 4H), 1.80 (m, 4H). HPLC (method B) $t_R$ 9.40 min (100.00 area %). Anal. ($C_{22}H_{16}N_2O_2$.0.3$H_2O$) C, H, N.

2-(4-(6-Cyanobenzofuran-2-yl)butyl)benzofuran-6-carbonitrile (114). Following the procedure described above for 103, 114 was prepared from 108 as a white solid (0.4 g, 10.0%): mp 215-217° C. ($CHCl_3$). $^1$H NMR (DMSO-$d_6$) δ8.11 (s, 2H), 7.75 (d, J=8.2 Hz, 2H), 7.55 (d, J=8.2 Hz, 2H), 6.80 (s, 2H), 2.91 (br s, 4H), 1.80 (br s, 4H). HPLC (method B) $t_R$ 9.32 min (100.00 area %). Anal. ($C_{22}H_{16}N_2O_2$.0.4$H_2O$) C, H, N.

2-(5-(5-Cyanobenzofuran-2-yl)pentyl)benzofuran-5-carbonitrile (115). Following the procedure described above for 103, 115 was prepared from 109 as a white solid (1.7 g, 42%): mp 133-134° C. (EtOAc/hexanes). $^1$H NMR (DMSO-$d_6$) δ8.06 (s, 2H), 7.68 (d, J=8.2 Hz, 2H), 7.64 (d, J=8.2 Hz, 2H), 6.71 (s, 2H), 2.83 (m, 4H), 1.77 (m, 4H), 1.44 (m, 2H). HPLC (method B) $t_R$ 9.90 min (100.00 area %). Anal. ($C_{23}H_{18}N_2O_2$.0.1$H_2O$) C, H, N.

2-(5-(6-Cyanobenzofuran-2-yl)pentyl)benzofuran-6-carbonitrile (116). Following the procedure described above for 103, 116 was prepared from 110 as a white solid (3.3 g, 50%): mp 106-107° C. (EtOAc/hexanes). $^1$H NMR (DMSO-$d_6$) δ8.11 (br s, 2H), 7.75 (d, J=8.2 Hz, 2H), 7.55 (dd, J=8.2, 1.0 Hz, 2H), 6.79 (s, 2H), 2.87 (t, J=7.1 Hz, 4H), 1.78 (m, 4H), 1.44 (m, 2H). HPLC (method B) $t_R$ 9.89 min (95.14 area %). Anal. ($C_{23}H_{18}N_2O_2$) C, H, N.

2-(3-Methoxyphenyl)benzofuran-5-carbonitrile (120). Following the procedure described above for 95, 120 was prepared from 117 and 118 as white solid (3.45 g, 81%): mp 129-131° C. (EtOAc/hexanes). $^1$H NMR (DMSO-$d_6$) δ8.24 (d, J=1.6 Hz, 1H), 7.86 (d, J=8.2 Hz, 1H), 7.77 (dd, J=8.2, 1.6 Hz, 1H), 7.61 (s, 1H), 7.55 (d, J=7.7 Hz, 1H), 7.50 (m, 1H), 7.46 (dd, J=8.2, 7.7 Hz, 1H), 7.04 (dd, J=8.2 and 2.1 Hz, 1H). HPLC (method B) $t_R$ 7.85 min (100.0 area %). Anal. ($C_{16}H_{11}NO_2$) C, H, N.

Methyl-2-(3-methoxyphenyl)benzofuran-6-carboxylate (121). Following the procedure described above for 95, 121 was prepared from 94 and 118 as white solid (16.1 g, 81%): mp 150-152° C. (EtOAc). $^1$H NMR (DMSO-$d_6$) δ8.17 (br s, 1H), 7.89 (d, J=8.2 Hz, 1H), 7.79 (d, J=8.2 Hz, 1H), 7.62 (s, 1H), 7.57 (d, J=7.7 Hz, 1H), 7.49 (m, 1H), 7.47 (dd, J=8.2, 7.7 Hz, 1H), 7.05 (dd, J=8.2, 2.1 Hz, 1H), 3.89 (s, 3H), 3.86 (s, 3H). HPLC (method B) $t_R$ 8.26 min (100.0 area %). Anal. ($C_{17}H_{14}O_4$.0.1EtOAc) C, H.

Methyl-2-(4-methoxyphenyl)benzofuran-6-carboxylate (122). Following the procedure described above for 95, 122 was prepared from 94 and 119 as white solid (11.6 g, 75%): mp 163-164° C. (EtOAc). $^1$H NMR (DMSO-$d_6$) δ8.13 (br s, 1H), 7.92 (d, J=7.7 Hz, 2H), 7.86 (d, J=7.7 Hz, 1H), 7.73 (d, J=7.7 Hz, 1H), 7.41 (s, 1H),.49 (m, 1H), 7.10 (d, J=7.7 Hz, 2H), 3.88 (s, 3H), 3.84 (s, 3H). HPLC (method B) $t_R$ 8.25 min (100.0 area %). Anal. ($C_{17}H_{14}O_4$.0.1EtOAc) C, H.

2-(3-Methoxyphenyl)benzofuran-6-carbonitrile (123). Following the procedure described above for 103, 123 was prepared from 121 as white solid (9.31 g, 68%): mp 148-150° C. (CHCl$_3$/hexanes). $^1$H NMR (DMSO-$d_6$) δ8.26 (br s, 1H), 7.85 (d, J=8.2 Hz, 1H), 7.69 (dd, J=8.2, 1.1 Hz, 1H), 7.66 (d, J=1.1 Hz, 1H), 7.56 (ddd, J=7.7, 1.6, 1.1 Hz, 1H), 7.51 (dd, J=2.2, 1.6 Hz, 1H), 7.47 (dd, J=8.2, 7.7 Hz, 1H), 7.06 (ddd, J=8.2, 2.2, 1.1 Hz, 1H), 3.86 (s, 3H). HPLC (method B) $t_R$ 7.71 min (100.0 area %). Anal. ($C_{16}H_{11}NO_2$) C, H, N.

2-(4-Methoxyphenyl)benzofuran-6-carbonitrile (124). Following the procedure described above for 103, 124 was prepared from 122 as white solid (6.93 g, 69%): mp 141-142° C. (EtOAc). $^1$H NMR (DMSO-$d_6$) δ8.19 (br s, 1H), 7.91 (d, J=8.8 Hz, 2H), 7.80 (d, J=8.2 Hz, 1H), 7.66 (d, J=8.2 Hz, 1H), 7.44 (s, 1H), 7.11 (d, J=8.8 Hz, 2H), 3.84 (s, 3H). HPLC (method B) $t_R$ 7.76 min (100.0 area %). Anal. ($C_{16}H_{11}NO_2$) C, H, N.

General Procedure for Synthesis of 2-(Hydroxyphenyl)Benzofuran Carbonitriles (125, 127, 128)

2-(3-Hydroxyphenyl)benzofuran-5-carbonitrile (125). To a melted pyridine hydrochloride (15.0 g) at 160-180° C. was added 2-(3-methoxyphenyl)benzofuran-5-carbonitrile (120) in one portion and the stirring continued at 180° C. for 2.5 h. The mixture was cooled down, diluted with water (100 mL) and 1 M HCl (50 mL) and stirred at room temperature for 30 min. A precipitate formed was separated, washed with 1 M HCl (150 mL) and water (150 mL) and dried. The residue was purified by flash chromatography (silica gel, EtOAc/hexanes 1/3) followed by recrystallization to give 125 as white solid (1.50 g, 69%): mp 222-224° C. (EtOAc/hexanes). $^1$H NMR (DMSO-$d_6$) δ9.78 (d, J=1.1 Hz, 1H), 8.21 (br s, 1H), 7.85 (d, J=8.2 Hz, 1H), 7.75 (ddd, J=8.2, 1.6, 1.1 Hz, 1H), 7.48 (s, 1H), 7.40 (dd, J=8.2, 1.1 Hz, 1H), 7.33 (dd, J=8.2, 7.7 Hz, 1H), 6.86 (ddd, J=8.2, 2.2, 1.1 Hz, 1H). HPLC (method B) $t_R$ 5.70 min (100.0 area %). Anal. ($C_{15}H_9NO_2$) C, H, N.

2-(3-Hydroxyphenyl)benzofuran-6-carbonitrile (127). While solid (6.78 g, 80%): mp 225-227° C. (EtOAc). $^1$H NMR (DMSO-$d_6$) δ9.82 (s, 1H), 8.25 (br s, 1H), 7.83 (d, J=8.2 Hz, 1H), 7.68 (d, J=8.2 Hz, 1H), 7.53 (s, 1H), 7.42 (d, J=7.7 Hz, 1H), 7.40-7.30 (m, 3H), 6.88 (d, J=7.7 Hz, 1H). HPLC (method B) $t_R$ 5.77 min (100.0 area %). Anal. ($C_{15}H_9NO_2$.0.1EtOAc) C, H, N.

2-(4-Hydroxyphenyl)benzofuran-6-carbonitrile (128). White solid (5.00 g, 80%): mp 272-274° C. (EtOH). $^1$H NMR (DMSO-$d_6$) δ10.08 (s, 1H), 8.18 (br s, 1H), 7.80 (d, J=8.8 Hz, 2H), 7.78 (d, J=8.2 Hz, 1H), 7.64 (dd, J=8.2, 1.1 Hz, 1H), 7.35 (s, 1H), 6.93 (d, J=8.8 Hz, 2H). HPLC (method B) $t_R$ 5.76 min (100.0 area %). Anal. ($C_{15}H_9NO_2$) C, H, N.

General Procedure for Syntheses of (4-Cyanophenoxy)alkoxy)phenyl)benzofuran-carbonitriles (133-148)

2-(3-(3-(4-Cyanophenoxy)propoxy)phenyl)benzofuran-5-carbonitrile (133). A mixture of 2-(3-hydroxphenyl)-5-cyanobenzofuran (125) (1.176 g, 5 mmol) and $K_2CO_3$ (0.829 g, 6 mmol) in dry DMF (25 mL) was heated up to 60° C. 4-(3-Bromopropoxy)benzonitrile (129) was added in one portion and the reaction was kept at 80-100° C. overnight. The mixture was cooled down to room temperature and poured into iced water (100 mL) and stirred for 30 min. A precipitate formed was separated by filtration, washed with water (50 mL) and ethanol (50 mL). Drying under high vacuum and recrystallization from the mixture of DMF and ethanol afforded the desired product as white solid (1.65 g, 84%): mp 157-158° C. (DMF/EtOH). $^1$H NMR (DMSO-$d_6$) δ8.24 (d, J=1.6 Hz, 1H), 7.86 (d, J=8.6 Hz, 1H), 7.78 (d, J=8.8 Hz, 2H), 7.77 (dd, J=8.6, 1.6 Hz, 1H), 7.61 (s, 1H), 7.55 (d, J=7.8 Hz, 1H), 7.52 (m, 1H), 7.45 (dd, J=7.8, 7.8 Hz, 1H), 7.16 (d, J=8.8 Hz, 2H), 7.07 (dd, J=7.8, 1.7 Hz, 1H), 4.35-4.15 (m, 4H), 2.30-2.15 (m, 2H). HPLC (method B) $t_R$ 9.63 min (100.0 area %). Anal. ($C_{25}H_{18}N_2O_3$) C, H, N.

2-(3-(4-(4-Cyanophenoxy)butoxy)phenyl)benzofuran-5-carbonitrile (134). White solid (1.57 g, 81%): mp 130-132° C. (DMF/EtOH). $^1$H NMR (DMSO-$d_6$) δ8.24 (br s, 1H), 7.85 (d, J=8.6 Hz, 1H), 7.76 (d, J=8.8 Hz, 3H), 7.60 (s, 1H), 7.54 (d, J=7.8 Hz, 1H), 7.53 (m, 1H), 7.47 (dd, J=7.8, 7.8 Hz, 1H), 7.13 (d, J=8.8 Hz, 2H), 7.04 (dd, J=7.8, 1.7 Hz, 1H), 4.25-4.00 (m, 4H), 2.00-1.80 (m, 4H). HPLC (method B) $t_R$ 10.04 min (100.0 area %). Anal. ($C_{26}H_{20}N_2O_3$) C, H, N.

2-(3-(5-(4-Cyanophenoxy)pentyloxy)phenyl)benzofuran-5-carbonitrile (135). White solid (3.24 g, 85%): mp 142-145° C. (DMF/EtOH). $^1$H NMR (DMSO-$d_6$) δ8.23 (d, J=1.6 Hz, 1H), 7.85 (d, J=8.7 Hz, 1H), 7.77 (dd, J=8.7, 1.7 Hz, 1H), 7.76 (d, J=8.8 Hz, 2H), 7.61 (s, 1H), 7.53 (d, J=8.2 Hz, 1H), 7.50 (m, 1H), 7.44 (dd, J=8.2, 7.7 Hz, 1H), 7.12 (d, J=8.8 Hz, 2H), 7.03 (dd, J=7.7, 1.7 Hz, 1H), 4.20-3.95 (m, 4H), 1.90-1.70 (m, 4H), 1.70-1.50 (m, 2H). HPLC (method B) $t_R$ 10.46 min (100.0 area %). Anal. ($C_{27}H_{22}N_2O_3$.0.1DMF) C, H, N.

2-(3-(6-(4-Cyanophenoxy)hexyloxy)phenyl)benzofuran-5-carbonitrile (136). White solid (1.65 g, 79%): mp 134-136° C. (DMF/EtOH). $^1$H NMR (DMSO-$d_6$) δ8.24 (d, J=1.6 Hz, 1H), 7.85 (d, J=8.2 Hz, 1H), 7.77 (dd, J=8.2, 1.7 Hz, 1H), 7.74 (d, J=8.8 Hz, 2H), 7.61 (s, 1H), 7.53 (d, J=7.8 Hz, 1H), 7.49 (m, 1H), 7.44 (dd, J=7.8, 7.8 Hz, 1H), 7.10 (d, J=8.8 Hz, 2H), 7.02 (dd, J=7.8, 1.7 Hz, 1H), 4.15-3.95 (m, 4H), 1.85-1.65 (m, 4H), 1.65-1.45 (m, 4H). HPLC (method B) $t_R$ 10.90 min (100.0 area %). Anal. ($C_{28}H_{24}N_2O_3$) C, H, N.

2-(4-(3-(4-Cyanophenoxy)propoxy)phenyl)benzofuran-5-carbonitrile (137). White solid (3.68 g, 93%): mp 188-189° C. (DMF/EtOH). $^1$H NMR (DMSO-$d_6$) δ8.17 (d, J=1.6 Hz, 1H), 7.89 (d, J=8.8 Hz, 2H), 7.82 (d, J=8.2 Hz, 1H), 7.77 (d, J=8.8 Hz, 2H), 7.72 (dd, J=8.2 and 1.6 Hz, 4H), 7.40 (s, 1H), 7.14 (d, J=8.8 Hz, 2H), 7.12 (d, J=8.8 Hz, 2H), 4.30-4.15 (m, 4H), 2.30-2.15 (m, 2H). HPLC (method B) $t_R$ 9.62 min (100.0 area %). Anal. ($C_{25}H_{18}N_2O_3$) C, H, N.

2-(4-(4-(4-Cyanophenoxy)butoxy)phenyl)benzofuran-5-carbonitrile (138). White solid (3.88 g, 89%): mp 186-188° C. (DMF/EtOH). $^1$H NMR (DMSO-$d_6$) δ8.18 (d, J=1.6 Hz, 1H), 7.89 (d, J=8.8 Hz, 2H), 7.82 (d, J=8.2 Hz, 1H), 7.77 (d, J=8.8 Hz, 2H), 7.73 (dd, J=8.2, 1.6 Hz, 1H), 7.40 (s, 1H), 7.11 (d, J=8.8 Hz, 2H), 7.10 (d, J=8.8 Hz, 2H), 4.20-4.00 (m, 4H), 2.00-1.80 (m, 4H). HPLC (method B) $t_R$ 10.03 min (100.0 area %). Anal. ($C_{26}H_{20}N_2O_3$.0.1DMF) C, H, N.

2-(4-(5-(4-Cyanophenoxy)pentyloxy)phenyl)benzofuran-5-carbonitrile (139). White solid (4.24 g, 94%): mp 163-166° C. (DMF/EtOH). $^1$H NMR (DMSO-$d_6$) δ8.17 (d, J=1.6 Hz, 1H), 7.88 (d, J=8.8 Hz, 2H), 7.81 (d, J=8.2 Hz, 1H), 7.75 (d, J=8.8 Hz, 2H), 7.72 (dd, J=8.2, 1.6 Hz, 1H), 7.39 (s, 1H), 7.10 (d, J=8.8 Hz, 2H), 7.09 (d, J=8.8 Hz, 2H), 4.15-4.00 (m, 4H), 1.90-1.75 (m, 4H), 1.70-1.50 (m, 2H). HPLC (method B) $t_R$ 10.48 min (100.0 area %). Anal. ($C_{27}H_{22}N_2O_3$.0.1DMF.0.2H$_2$O) C, H, N.

2-(4-(6-(4-cyanophenoxy)hexyloxy)phenyl)benzofuran-5-carbonitrile (140). White solid (4.30 g, 93%): mp 148-151° C. (DMF/EtOH). $^1$H NMR (DMSO-$d_6$) δ8.17 (d, J=1.6 Hz, 1H), 7.88 (d, J=8.8 Hz, 2H), 7.81 (d, J=8.2 Hz, 1H), 7.75 (d, J=8.8 Hz, 2H), 7.72 (dd, J=8.2, 1.6 Hz, 1H), 7.39 (s, 1H), 7.10 (d, J=8.8 Hz, 2H), 7.09 (d, J=8.8 Hz, 2H), 4.15-3.95 (m, 4H), 1.85-1.65 (m, 4H), 1.60-1.40 (m, 4H). HPLC (method B) $t_R$ 10.99 min (100.0 area %). Anal. ($C_{28}H_{24}N_2O_3$.0.2DMF.0.2H$_2$O) C, H, N.

2-(3-(3-(4-Cyanophenoxy)propoxy)phenyl)benzofuran-6-carbonitrile (141). White solid (1.89 g, 71%): mp 128-129° C. (DMF/EtOH). $^1$H NMR (DMSO-$d_6$) δ8.24 (br s, 1H), 7.85 (d, J=7.7 Hz, 1H), 7.77 (d, J=8.2 Hz, 2H), 7.69 (d, J=7.7 Hz, 1H), 7.65 (s, 1H), 7.56 (d, J=7.7 Hz, 1H), 7.52 (br s, 1H), 7.46 (dd, J=7.7, 7.7 Hz, 1H), 7.16 (d, J=8.2 Hz, 2H), 7.07 (dd, J=7.7, 1.7 Hz, 1H), 4.35-4.15 (m, 4H), 2.30-2.10 (m, 2H). HPLC (method B) $t_R$ 9.61 min (100.0 area %). Anal. ($C_{25}H_{18}N_2O_3$) C, H, N.

2-(3-(4-(4-Cyanophenoxy)butoxy)phenyl)benzofuran-6-carbonitrile (142). White solid (1.84 g, 81%): mp 129-130° C. (DMF/EtOH). $^1$H NMR (DMSO-$d_6$) δ8.24 (br s, 1H), 7.85 (d, J=8.2 Hz, 1H), 7.76 (d, J=8.8 Hz, 2H), 7.69 (d, J=8.2 Hz, 1H), 7.64 (s, 1H), 7.55 (d, J=7.7 Hz, 1H), 7.50 (br s, 1H), 7.46 (dd, J=7.7, 7.7 Hz, 1H), 7.13 (d, J=8.8 Hz, 2H), 7.07 (dd, J=7.7, 1.7 Hz, 1H), 4.25-4.00 (m, 4H), 2.00-1.80 (m, 4H). HPLC (method B) $t_R$ 10.03 min (100.0 area %). Anal. ($C_{26}H_{20}N_2O_3$.0.1DMF) C, H, N.

2-(3-(5-(4-Cyanophenoxy)pentyloxy)phenyl)benzofuran-6-carbonitrile (143). White solid (1.88 g, 65%): mp 138-140° C. (DMF/EtOH). $^1$H NMR (DMSO-$d_6$) δ8.25 (br s, 1H), 7.85 (d, J=8.2 Hz, 1H), 7.76 (d, J=8.8 Hz, 2H), 7.69 (d, J=8.2 Hz, 1H), 7.65 (s, 1H), 7.53 (d, J=7.7 Hz, 1H), 7.50 (br s, 1H), 7.45 (dd, J=7.7, 7.7 Hz, 1H), 7.12 (d, J=8.8 Hz, 2H), 7.06 (dd, J=7.7, 1.6 Hz, 1H), 4.20-3.95 (m, 4H), 1.90-1.70 (m, 4H), 1.70-1.50 (m, 2H). HPLC (method B) $t_R$ 10.44 min (100.0 area %). ($C_{27}H_{22}N_2O_3$) C, H, N.

2-(3-(6-(4-Cyanophenoxy)hexyloxy)phenyl)benzofuran-6-carbonitrile (144). White solid (2.16 g, 89%): mp 125-127° C. (DMF/EtOH). $^1$H NMR (DMSO-$d_6$) δ8.25 (br s, 1H), 7.85 (d, J=8.2 Hz, 1H), 7.75 (d, J=8.2 Hz, 2H), 7.69 (d, J=8.2 Hz, 1H), 7.65 (s, 1H), 7.55 (d, J=7.7 Hz, 1H), 7.50 (br s, 1H), 7.45 (dd, J=7.7, 7.7 Hz, 1H), 7.10 (d, J=8.2 Hz, 2H), 7.06 (dd, J=7.7, 1.6 Hz, 1H), 4.15-3.95 (m, 4H), 1.85-1.65 (m, 4H), 1.65-1.45 (m, 4H). HPLC (method B) $t_R$ 10.89 min (100.0 area %). Anal. ($C_{28}H_{24}N_2O_3$.0.1DMF) C, H, N.

2-(4-(3-(4-Cyanophenoxy)propoxy)phenyl)benzofuran-6-carbonitrile (145). White solid (1.87 g, 86%): mp 208-210° C. (DMF/EtOH). $^1$H NMR (DMSO-$d_6$) δ8.20 (br s, 1H), 7.91 (d, J=8.2 Hz, 2H), 7.80 (d, J=8.2 Hz, 1H), 7.78 (d, J=8.2 Hz, 2H), 7.66 (d, J=8.2 Hz, 1H), 7.45 (s, 1H), 7.15 (d, J=8.2 Hz, 2H), 7.13 (d, J=8.2 Hz, 2H), 4.35-4.15 (m, 4H), 2.30-2.15 (m, 2H). HPLC (method B) $t_R$ 9.61 min (100.0 area %). Anal. ($C_{25}H_{18}N_2O_3$) C, H, N.

2-(4-(4-(4-Cyanophenoxy)butoxy)phenyl)benzofuran-6-carbonitrile (146). White solid (2.14 g, 93%): mp 187-189° C. (DMF/EtOH). $^1$H NMR (DMSO-$d_6$) δ8.20 (br s, 1H), 7.90 (d, J=8.8 Hz, 2H), 7.80 (d, J=8.2 Hz, 1H), 7.77 (d, J=8.8 Hz, 2H), 7.65 (d, J=8.2 Hz, 1H), 7.45 (s, 1H), 7.12 (d, J=8.8 Hz, 2H), 7.10 (d, J=8.8 Hz, 2H), 4.20-4.00 (m, 4H), 2.00-1.80 (m, 4H). HPLC (method B) $t_R$ 10.02 min (100.0 area %). Anal. ($C_{26}H_{20}N_2O_3$) C, H, N.

2-(4-(5-(4-Cyanophenoxy)pentyloxy)phenyl)benzofuran-6-carbonitrile (147). White solid (2.27 g, 90%): mp 165-167° C. (DMF/EtOH). $^1$H NMR (DMSO-$d_6$) δ8.20 (br s, 1H), 7.90 (d, J=8.8 Hz, 2H), 7.80 (d, J=8.2 Hz, 1H), 7.76 (d, J=8.8 Hz, 2H), 7.65 (d, J=8.2 Hz, 1H), 7.44 (s, 1H), 7.11 (d, J=8.8 Hz, 2H), 7.09 (d, J=8.8 Hz, 2H), 4.15-3.95 (m, 4H), 1.90-1.75 (m, 4H), 1.70-1.50 (m, 2H). HPLC (method B) $t_R$ 10.47 min (100.0 area %). Anal. ($C_{27}H_{22}N_2O_3$) C, H, N.

2-(4-(6-(4-Cyanophenoxy)hexyloxy)phenyl)benzofuran-6-carbonitrile (148). White solid (1.51 g, 84%): mp 159-160° C. (DMF/EtOH). $^1$H NMR (DMSO-$d_6$) δ8.20 (br s, 1H), 7.89 (d, J=8.8 Hz, 2H), 7.79 (d, J=8.2 Hz, 1H), 7.76 (d, J=8.8 Hz, 2H), 7.66 (d, J=8.2 Hz, 1H), 7.44 (s, 1H), 7.09 (d, J=8.8 Hz, 4H), 4.15-3.95 (m, 4H), 1.85-1.65 (m, 4H), 1.60-1.40 (m, 4H). HPLC (metohd B) $t_R$ 10.98 min (100.0 area %). Anal. ($C_{28}H_{24}N_2O_3$) C, H, N.

General Procedure for Syntheses of Bis-amidoximes (178, 180, 182, 183, 184-186)

2-(4-(N-Hydroxycarbamimidoyl)phenyl)-N-hydroxybenzofuran-5-carboxamidine (178). To a solution of NH$_2$OH.HCl (6.00 g, 86.3 mmol) in dry DMSO (50 mL) was added Potassium tert-Butoxide (9.00 g, 80.2 mmol) and the mixture was stirred for 30 min followed by addition of dinitrile 151 (3.00 g, 12.3 mmol) in dry DMSO (50 mL). Reaction mixture was stirred at room temperature for 4 days, poured into ice water (200 mL), stirred for 1 hour. White precipitate was filtered off, washed with water (200 mL) and ethanol (100 mL), dried and recrystallized from DMF-EtOH-aq HCl mixture to gave 3.46 g (74%): mp 185° C. (dec). HPLC (method A) $t_R$ 4.28 min (98.22 area %). Anal. ($C_{16}H_{14}N_4O_3$.2HCl) C, H, N, Cl.

2-(3-(N-Hydroxycarbamimidoyl)phenyl)-N-hydroxybenzofuran-6-carboxamidine (180). White solid (0.68 g, 72%): mp 210° C. (dec) (aq HCl). $^1$H NMR (DMSO-$d_6$) δ11.29 (br s, 2H), 9.40-8.50 (br m, 4H), 8.38 (s, 1H), 8.25 (d, J=7.7 Hz, 1H), 8.14 (s, 1H), 7.92 (d, J=8.2 Hz, 1H), 7.83 (d, J=8.2 Hz, 1H), 7.77 (s, 1H), 7.74 (d, J=7.6 Hz, 1H) 7.64 (dd, J=8.2, 1.7 Hz, 1H). HPLC (method A) $t_R$ 4.55 min (100.0 area %). Anal. ($C_{16}H_{14}N_4O_3$.2HCl.1.2H$_2$O) C, H, N, Cl.

2-(4-(N-Hydroxycarbamimidoyl)phenyl)-N-hydroxybenzofuran-6-carboxamidine (181) White solid (0.78 g, 83%): mp 210° C. (dec) (aq HCl). $^1$H NMR (DMSO-$d_6$) δ10.00-8.50 (br m, 6H), 8.19 (d, J=8.2 Hz, 2H), 8.15 (s, 1H), 7.95 (s, 1H), 7.94 (d, J=8.2 Hz, 2H), 7.88 (s, 1H), 7.69 (dd, J=8.2, 1.7 Hz, 1H). HPLC (method A) $t_R$ 4.33 min (100.0 area %). Anal. ($C_{16}H_{14}N_4O_3$.2HCl.1.2H$_2$O) C, H, N, Cl.

2-(4-(3-(4-(N-Hydroxycarbamimidoyl)phenoxy)propoxy)phenyl)-N-hydroxybenzofuran-5-carboxamidine (182). White solid (2.35 g, 76%): mp 204° C. (dec) (aq HCl). $^1$H NMR (DMSO-d$_6$) δ11.24 (s, 1H), 11.14 (s, 1H), 9.20 (br, 4H), 8.04 (s, 1H), 7.92 (d, J=9.1 Hz, 2H), 7.84 (d, J=8.9 Hz, 1H), 7.73 (d, J=9.1 Hz, 2H), 7.62 (d, J=8.9 Hz, 1H), 7.47 (s, 1H), 7.18 (d, J=8.9 Hz, 32H), 7.13 (d, J=8.9 Hz, 2H), 4.25 (m, 4H), 2.24 (m, 2H). HPLC (method A) $t_R$ 8.26 min (100.0 area %). Anal. (C$_{25}$H$_{24}$N$_4$O$_5$.2HCl.0.5H$_2$O) C, H, N, Cl.

2-(4-(5-(4-(N-Hydroxycarbamimidoyl)phenoxy)pentyloxy)phenyl)-N-hydroxybenzofuran-5-carboxamidine (183). White solid (0.92 g, 71%): mp 202° C. (dec) (aq HCl). HPLC (method A) $t_R$ 9.04 min (95.38 area %). Anal. (C$_{27}$H$_{28}$N$_4$O$_5$.2HCl.0.5H$_2$O) C, H, N, Cl.

2-(5-(6-(N-Hydroxycarbamimidoyl)benzofuran-2-yl)pentyl)-N-hydroxybenzofuran-6-carboxamidine (184). While solid (1.10 g, 71%): mp 220° C. (dec) (aq HCl-EtOH). $^1$H NMR (DMSO-d$_6$) δ11.19 (s, 2H), 9.04 (br, 4H), 7.95 (s, 2H), 7.73 (d, J=8.2 Hz, 2H), 7.56 (d, J=8.2 Hz, 2H), 6.77 (s, 2H), 2.86 (t, J=7.1 Hz, 4H), 1.76 (m, 4H), 1.45 (m, 2H). HPLC (method B) $t_R$ 3.11 min (100.0 area %). Anal. (C$_{23}$H$_{24}$N$_4$O$_4$.2.1HCl.0.2 H$_2$O) C, H, N, Cl.

2-(3-(5-(N-Hydroxycarbamimidoyl)benzofuran-2-yl)propyl)-N-hydroxybenzofuran-5-carboxamidine (185). White solid (0.51 g, 35%): mp 145-147° C. (dec) (aq HCl). $^1$H NMR (DMSO-d$_6$) δ11.26 (s, 2H), 9.20 (br, 6H), 7.99 (d, J=1.6 Hz, 2H), 7.76 (d, J=8.8 Hz, 2H), 7.59 (dd, J=8.8, 1.6 Hz, 2H), 6.87 (s, 2H), 2.95 (m, 4H), 2.17 (m, 2H). HPLC (method B) $t_R$ 1.67 min (97.60 area %). Anal. (C$_{21}$H$_{20}$N$_4$O$_4$.2HCl.1.5H$_2$O) C, H, N, Cl.

2-(4-(5-(N-Hydroxycarbamimidoyl)benzofuran-2-yl)butyl)-N-hydroxybenzofuran-5-carboxamidine (186). White solid (0.97 g, 34%): mp 231° C. (dec) (aq HCl). $^1$H NMR (DMSO-d$_6$) δ11.14 (s, 2H), 9.01 (br, 4H), 7.97 (s, 2H), 7.73 (d, J=8.8 Hz, 2H), 7.57 (d, J=8.8 Hz, 2H), 6.80 (s, 2H), 2.90 (br, 4H), 1.81 (br, 2H). HPLC (method B) $t_R$ 2.27 min (100.0 area %). Anal. (C$_{22}$H$_{22}$N$_4$O$_4$.2HCl.0.5H$_2$O) C, H, N, Cl.

2-(5-(5-(N-Hydroxycarbamimidoyl)benzofuran-2-yl)pentyl)-N-hydroxybenzofuran-5-carboxamidine (192). White solid (2.03 g, 72%): mp 120° C. (dec) (aq HCl, EtOH). $^1$H NMR (DMSO-d$_6$) δ11.29 (s, 2H), 9.11 (br, 4H), 7.99 (s, 2H), 7.67 (m, 4H), 6.81 (s, 2H), 2.85 (br, 4H), 1.78 (br, 4H), 1.47 (br, 2H). HPLC (method B) $t_R$ 2.84 min (96.95 area %). Anal. (C$_{23}$H$_{24}$N$_4$O$_4$.2HCl.0.5H$_2$O.0.5EtOH) C, H, N, Cl.

General Procedure for Syntheses of Bis-methylamidoximes (179, 181, 187-189)

2-(4-(N-Methoxycarbamimidoyl)phenyl)-N-methoxybenzofuran-5-carboxamidine (179). 1 M aqueous NaOH solution (20 mL) was added to a stirred solution of 178 (1.70 g, 5.5 mmol) in DMSO (20 mL). The mixture was cooled and dimethyl sulfate (1.5 mL, 15.9 mmol) was added dropwise at 0° C. The mixture was stirred at 0° C. for 4 hours and then overnight at room temperature, diluted with water (100 mL). The product was separated as a white solid and purified by column chromatography (SiO$_2$, EtOAc, Hexanes) and recrystallized from aq HCl to give 0.4 g (22%): mp 270-271° C. (dec). $^1$H NMR (DMSO-d$_6$) δ7.96 (s, 1H), 7.94 (d, J=8.2 Hz, 2H), 7.80 (d, J=8.2 Hz, 2H), 7.64 (s, 2H), 7.55 (s, 2H), 6.16 (br, 2H), 6.13 (br, 2H), 3.77 (s, 3H), 3.76 (s, 3H). HPLC (method A) $t_R$ 9.41 min (100.0 area %). Anal. (C$_{18}$H$_{18}$N$_4$O$_3$.2HCl) C, H, N, Cl.

2-(5-(6-(N-Methoxycarbamimidoyl)benzofuran-2-yl)pentyl)-N-methoxybenzofuran-6-carboxamidine (187). White solid (0.33 g, 25%): mp 230-231° C. (dec) (aq HCl, EtOH). $^1$H NMR (DMSO-d$_6$) δ8.36 (br, 4H), 7.92 (s, 2H), 7.67 (d, J=8.2 Hz, 2H), 7.57 (d, J=8.2 Hz, 2H), 6.73 (s, 2H), 3.85 (s, 6H), 2.85 (t, J=7.1 Hz, 4H), 1.77 (m, 4H), 1.44 (m, 2H). HPLC (method B) $t_R$ 7.71 min (100.00 area %). Anal. (C$_{25}$H$_{28}$N$_4$O$_4$.2HCl.0.6H$_2$O.0.3EtOH) C, H, N, Cl.

2-(3-(5-(N-Methoxycarbamimidoyl)benzofuran-2-yl)propyl)-N-methoxybenzofuran-5-carboxamidine (188). White solid (0.14 g, 11%): mp 89-90° C. (dec) (aq HCl). $^1$H NMR (DMSO-d$_6$) δ8.59 (br, 4H), 7.97 (s, 2H), 7.73 (d, J=8.2 Hz, 2H), 7.57 (d, J=8.2 Hz, 2H), 6.83 (s, 2H), 3.85 (s, 6H), 2.93 (t, J=7.1 Hz, 4H), 2.16 (m, 2H). HPLC (method B) $t_R$ 6.03 min (94.52 area %). Anal. (C$_{23}$H$_{24}$N$_4$O$_4$.2.2HCl.4H$_2$O) C, H, N, Cl.

2-(4-(5-(N-Methoxycarbamimidoyl)benzofuran-2-yl)butyl)-N-methoxybenzofuran-5-carboxamidine (189). Yellow solid (0.20 g, 27%): mp 248-250° C. (dec) (aq HCl, EtOH). $^1$H NMR (DMSO-d$_6$) δ8.52 (br, 4H), 7.96 (s, 2H), 7.68 (d, J=8.8 Hz, 2H), 7.59 (d, J=8.8 Hz, 2H), 6.77 (s, 2H), 3.85 (s, 6H), 2.89 (br, 4H), 1.81 (br, 4H). HPLC (method B) $t_R$ 6.74 min (96.52 area %). Anal. (C$_{24}$H$_{26}$N$_4$O$_4$.2HCl) C, H, N, Cl.

General Procedure for Syntheses of Bis-amidoximes and Bis-methylamidoximes via Pinner Procedure (190, 191, 193)

2-(2-(5-(N-Hydroxycarbamimidoyl)benzofuran-2-yl)ethyl)-N-hydroxybenzofuran-5-carboxamidine (190). The mixture of freshly distilled ethanol (7 mL) and 1,4-dioxane (20 mL) was saturated with dry HCl (gas) at 0° C. Dinitrile 103 (1.05 g, 3.3 mmol) was added, reaction mixture was stirred at room temperature for 2 days, diluted with dry diethyl ether (70 mL) and placed in freezer for 3 hours. Forming precipitate was filtered off, dried under high vacuum for 3 hours, separated into 2 parts and reached with hydroxylamine and methylhydroxylamine immediately.

Hydroxylamine hydrochloride (1.04 g, 15.0 mmol) was dissolved in 0.5 M solution of NaOMe in MeOH (30 mL). Crude imidate (0.75 g, 1.6 mmol) was added and reaction mixture was stirred at room temperature for 2 days. Product was purified with prep-HPLC and converted into their HCl salt with 1 M aqueous HCl. Light yellow solid (0.12 g, 17%): mp 225° C. (dec). $^1$H NMR (DMSO-d$_6$) δ9.07 (br, 4H), 7.95 (d, J=1.6 Hz, 2H), 7.75 (d, J=8.2 Hz, 2H), 7.57 (dd, J=8.2, 1.6 Hz, 2H), 6.85 (s, 2H), 3.33 (s, 4H. HPLC (method A) $t_R$ 4.76 min (100.00 area %). Anal. (C$_{20}$H$_{18}$N$_4$O$_4$.2HCl) C, H, N, Cl.

2-(2-(5-(N-Methoxycarbamimidoyl)benzofuran-2-yl)ethyl)-N-methoxybenzofuran-5-carboxamidine (191). Light yellow solid (0.09 g, 12%): mp 245-246° C. (dec) (aq HCl). $^1$H NMR (DMSO-d$_6$) δ7.93 (d, J=1.6 Hz, 2H), 7.67 (d, J=8.2 Hz, 2H), 7.59 (dd, J=8.2, 1.6 Hz, 2H), 6.81 (s, 2H), 3.33 (s, 4H). HPLC (method A) $t_R$ 5.55 min (100.00 area %). Anal. (C$_{22}$H$_{22}$N$_4$O$_4$.1.9HCl.1.3H$_2$O) C, H, N, Cl.

2-(5-(5-(N-Methoxycarbamimidoyl)benzofuran-2-yl)pentyl)-N-methoxybenzofuran-5-carboxamidine (193). White solid (0.21 g, 23%): mp 118° C. (dec) (aq HCl, EtOH). $^1$H NMR (DMSO-d$_6$) δ8.9 (br, 2H), 8.01 (d, J=1.6 Hz, 2H), 7.72 (d, J=8.8 Hz, 2H), 7.64 (dd, J=8.8, 1.6 Hz, 2H), 6.78 (s, 2H), 3.87 (s, 4H). HPLC (method B) $t_R$ 7.48 min (100.00 area %). Anal. (C$_{25}$H$_{28}$N$_4$O$_4$.2HCl.0.7H$_2$O.0.1EtOH) C, H, N, Cl.

Example 8

Referring now to Table I, three compounds in the unsymmetrical benzofuran series of amidine-containing dications were found to be more active then pentamidine against *L. donovani* axenic amastigotes. Compounds with an amidine group in the 5-position of the benzofuran system and with the diether linking group in the 4'-position of the A ring and the 4"-position of the B ring appear to be the most active molecules in this series. The toxicity profile of these compounds against J774 macrophages, however, parallels the antiparasitic activity.

Referring now to Table II, several members of the isopropyl amidine series of unsymmetrical benzofurans possess antileishmanial activity similar to pentamidine against *L. donovani* amastigote-like organisms, although none in this series are as active as the amidine-containing unsymmetrical benzofurans. As in the amidine series, compounds with the diether linking group in the 4'-position of the A ring and the 4"-position of the B ring appear to be the most active molecules in this series. Again, little selectivity for parasites compared to J774 macrophages is seen.

Referring now to Table III, the imidazoline-containing unsymmetrical benzofuran 70 is as active as any of the amidine-containing compounds and also possesses modest (5-fold) selectively for axenic amastigotes over J774 macrophages. All of the other imidazoline-containing compounds were at least 10-fold less active against *Leishmania*, even those that also possess the diether linking group in the 4'-position of the A ring and the 4"-position of the B ring. This observation suggests that alkyl chain length has an important effect on antileishmanial activity in the imidazoline series.

Referring now to Table IV, in the 2-aryl benzofuran series, dications comprising an amidine group in the 4'-position are the most active, with isopropyl amidines and imidazolines again displaying lower activity. Analogs with a methoxy group in the 7-position of the benzofuran system have high antileishmanial activity.

Referring now to Table V, bis-benzofurans 11 and 8 are among the most active benzofuran-containing dications tested thus far against *L. donovani* axenic amastigotes. Preliminary structure-activity studies indicate that these 5,5'- and 6,6'-substituted compounds are more active than 4,4'-substituted bis-benzofurans. The amidines again appear more potent than the isopropyl amidines or imidazolines. Most importantly, 11 and 8 appear to be much less toxic to macrophages than *Leishmania*, being 41- and 14-fold more active against the parasites compared to the mammalian host cells, respectively.

TABLE I

Structures and in vitro anti-leishmania activities of unsymmetrical benzofuran-containing amidines.

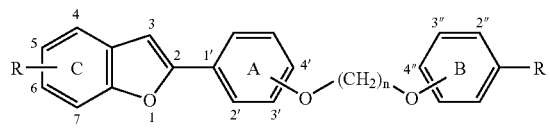

| Compound | R | Ring C Substitution | Ring A Substitution | Ring B Substitution | n | $IC_{50}$ vs. *L. donovani* (μM) | $IC_{50}$ vs. J774 macrophages (μM) |
|---|---|---|---|---|---|---|---|
| Pentamidine | | | | | | 2.0 ± 0.6 | 23 ± 6 |
| 53 | Am | 5 | 4' | 4" | 6 | 0.65 ± 0.17 | 0.60 ± 0.07 |
| 44 | Am | 5 | 4' | 4" | 3 | 0.78 ± 0.21 | 2.7 ± 0.3 |
| 47 | Am | 5 | 4' | 4" | 4 | 0.61 ± 0.53 | Not tested |
| 71 | Am | 6 | 4' | 4" | 4 | 3.22 ± 0.96 | 0.86 ± 0.20 |
| 32 | Am | 5 | 3' | 4" | 3 | 3.42 ± 0.90 | Not tested |
| 35 | Am | 5 | 3' | 4" | 4 | 4.45 ± 1.93 | 9.6 ± 1.5 |
| 62 | Am | 6 | 3' | 4" | 5 | 5.75 ± 0.06 | 5.6 ± 0.3 |
| 59 | Am | 6 | 3' | 4" | 4 | 5.93 ± 0.24 | 11 ± 2 |
| 56 | Am | 6 | 3' | 4" | 3 | 11.2 ± 0.28 | Not tested |
| 41 | Am | 5 | 3' | 4" | 6 | 22.6 ± 0.23 | Not tested |
| 65 | Am | 6 | 3' | 4" | 6 | 23.6 ± 1.09 | Not tested |

TABLE II

Structures and in vitro anti-leishmania activities of unsymmetrical benzofuran-containing isopropyl amidines.

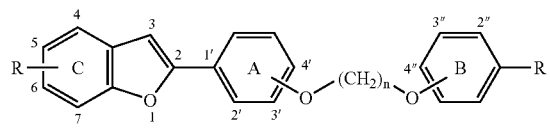

| Compound | R | Ring C Substitution | Ring A Substitution | Ring B Substitution | n | $IC_{50}$ vs. *L. donovani* (μM) | $IC_{50}$ vs. J774 macrophages (μM) |
|---|---|---|---|---|---|---|---|
| Pentamidine | | | | | | 2.0 ± 0.6 | 23 ± 6 |
| 75 | iPrAm | 6 | 4' | 4" | 5 | 1.35 ± 0.18 | 2.7 ± 0.1 |
| 78 | iPrAm | 6 | 4' | 4" | 6 | 2.62 ± 0.35 | 0.73 ± 0.03 |
| 69 | iPrAm | 6 | 4' | 4" | 3 | 3.18 ± 0.19 | 9.9 ± 1.7 |
| 33 | iPrAm | 5 | 3' | 3" | 3 | 4.49 ± 0.56 | Not tested |
| 72 | iPrAm | 6 | 4' | 4" | 4 | 4.52 ± 1.81 | Not tested |

TABLE II-continued

Structures and in vitro anti-leishmania activities of unsymmetrical benzofuran-containing isopropyl amidines.

| Compound | R | Ring C Substitution | Ring A Substitution | Ring B Substitution | n | IC$_{50}$ vs. *L. donovani* (μM) | IC$_{50}$ vs. J774 macrophages (μM) |
|---|---|---|---|---|---|---|---|
| 66 | iPrAm | 6 | 3' | 4" | 6 | 6.18 ± 0.06 | Not tested |
| 39 | iPrAm | 5 | 3' | 4" | 5 | 6.86 ± 2.10 | Not tested |
| 42 | iPrAm | 5 | 3' | 4" | 6 | 6.97 ± 1.39 | Not tested |
| 63 | iPrAm | 6 | 3' | 4" | 5 | 8.92 ± 0.71 | Not tested |
| 36 | iPrAm | 5 | 3' | 4" | 4 | 11.2 ± 0.04 | Not tested |
| 57 | iPrAm | 6 | 3' | 4" | 3 | 10.6 ± 6.42 | Not tested |
| 60 | iPrAm | 6 | 3' | 4" | 4 | 12.3 ± 0.09 | Not tested |

TABLE III

Structures and in vitro anti-leishmania activities of unsymmetrical benzofuran-containing imidazolines

| Compound | R | Ring C Substitution | Ring A Substitution | Ring B Substitution | n | IC$_{50}$ vs. *L. donovani* (μM) | IC$_{50}$ vs. J774 macrophages (μM) |
|---|---|---|---|---|---|---|---|
| Pentamidine | | | | | | 2.0 ± 0.6 | 23 ± 6 |
| 70 | Im | 6 | 4' | 4" | 3 | 0.48 ± 0.16 | 2.4 ± 0.1 |
| 58 | Im | 6 | 3' | 4" | 3 | 4.73 ± 1.71 | Not tested |
| 34 | Im | 5 | 3' | 4" | 3 | 5.93 ± 0.04 | 7.1 ± 0.8 |
| 61 | Im | 6 | 3' | 4" | 4 | 7.38 ± 2.55 | Not tested |
| 49 | Im | 5 | 4' | 4" | 4 | 9.21 ± 2.25 | Not tested |
| 76 | Im | 6 | 4' | 4" | 5 | 10.4 ± 0.78 | Not tested |
| 37 | Im | 5 | 3' | 4" | 4 | 11.7 ± 0.14 | Not tested |
| 73 | Im | 6 | 4' | 4" | 4 | 13.2 ± 0.86 | Not tested |
| 79 | Im | 6 | 4' | 4" | 6 | 15.3 ± 1.72 | Not tested |
| 64 | Im | 6 | 3' | 4" | 5 | 16.5 ± 3.45 | Not tested |
| 67 | Im | 6 | 3' | 4" | 6 | 43.5 ± 0.69 | Not tested |

TABLE IV

Structures and in vitro anti-leishmania activities 2-aryl benzofuran-containing dications.

| Compound | R$_1$ | Ring C R$_1$ Substitution | Ring C R$_2$ Substitution | Ring A R$_1$ Substitution | IC$_{50}$ vs. *L. donovani* (μM) |
|---|---|---|---|---|---|
| Pentamidine | | | | | 2.0 ± 0.6 |
| 175 | Am | 5 | OCH$_3$ | 4' | 3.00 ± 0.56 |
| 172 | Am | 6 | H | 4' | 3.13 ± 0.15 |
| 177 | Im | 5 | OCH$_3$ | 4' | 4.45 ± 0.36 |
| 166 | Am | 5 | H | 3' | 5.82 ± 0.06 |
| 173 | iPrAm | 6 | H | 4' | 11.8 ± 1.28 |
| 167 | iPrAm | 5 | H | 3' | 13.4 ± 0.64 |

TABLE IV-continued

Structures and in vitro anti-leishmania activities 2-aryl benzofuran-containing dications.

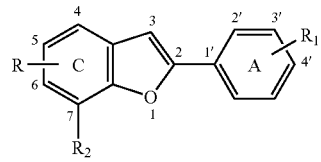

| Compound | $R_1$ | Ring C $R_1$ Substitution | Ring C $R_2$ Substitution | Ring A $R_1$ Substitution | $IC_{50}$ vs. *L. donovani* (μM) |
|---|---|---|---|---|---|
| 169 | Am | 6 | H | 3' | 14.4 |
| 168 | Im | 5 | H | 3' | 23.7 ± 0.17 |
| 170 | iPrAm | 6 | H | 3' | 24.4 ± 0.10 |
| 174 | Im | 6 | H | 4' | >50 |
| 171 | Im | 6 | H | 3' | >100 |

TABLE V

Structures and in vitro anti-leishmania activities of bis-benzofuran-containing dications.

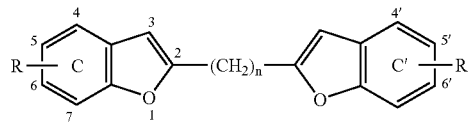

| Compound | R | Ring C and C' Substitutions | n | $IC_{50}$ vs. *L. donovani* (μM) | $IC_{50}$ vs. J774 macrophages (μM) |
|---|---|---|---|---|---|
| Pentamidine | | | | 2.0 ± 0.6 | 23 ± 6 |
| 11 | Am | 6,6' | 2 | 0.88 ± 0.25 | 29 ± 0 |
| 8 | Am | 5,5' | 2 | 1.06 ± 0.18 | 15 ± 1 |
| 1 | Am | 4,4' | 1 | 14.0 ± 5.76 | Not tested |
| 3 | Im | 4,4' | 1 | >100 | Not tested |
| 2 | iPrAm | 4,4' | 1 | >100 | Not tested |

TABLE VI(a)

Anti-protozoan Data for 'Unsymmetrical' Benzofuran Diamidines.

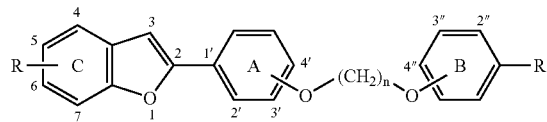

| N | R | Ring C Position | Ring A Position | n | T.b.r. $IC_{50}$ (μM) | *T. cruzi* $IC_{50}$ (μM) | *P. falcip.* $IC_{50}$ (μM) | Cytotox. $IC_{50}$ (μM) | DNA binding Δ $T_m$ | Leishmania Donovani $IC_{50}$ (μM) |
|---|---|---|---|---|---|---|---|---|---|---|
| 32 | Am | 5 | 3' | 3 | 0.9067 | 16.1 | 0.0397 | 10.4 | 18.7 | 3.42 ± 0.90 |
| 33 | IprAm | 5 | 3' | 3 | 0.5467 | 93.6 | 0.0613 | 26.5 | 14.8 | 4.49 ± 0.56 |
| 34 | Im | 5 | 3' | 3 | 1.174 | Not Tested | 0.1085 | 6.52 | Not Tested | 5.93 ± 0.04 |
| 35 | Am | 5 | 3' | 4 | 0.7787 | Not Tested | 0.0755 | 8.06 | Not Tested | 4.45 ± 1.93 |
| 36 | IprAm | 5 | 3' | 4 | 0.5370 | Not Tested | 0.2694 | 36.5 | Not Tested | 11.2 ± 0.04 |
| 37 | Im | 5 | 3' | 4 | 1.172 | Not Tested | 0.0986 | 9.52 | Not Tested | 11.7 ± 0.14 |
| 38 | Am | 5 | 3' | 5 | 0.8631 | 7.78 | 0.4284 | 3.02 | 21.1 | 10.5 ± 2.11 |
| 39 | IprAm | 5 | 3' | 5 | 0.4521 | 26.0 | 0.1228 | 10.1 | 20.8 | 6.86 ± 2.10 |
| 40 | Im | 5 | 3' | 5 | 0.5971 | 7.88 | 0.0990 | 2.62 | Not Tested | 16.6 ± 6.20 |
| 41 | Am | 5 | 3' | 6 | 1.614 | Not Tested | 0.4302 | 3.12 | Not Tested | 22.6 ± 0.23 |
| 42 | IprAm | 5 | 3' | 6 | 1.155 | Not Tested | 0.1833 | 7.36 | Not Tested | 6.97 ± 1.39 |
| 43 | Im | 5 | 3' | 6 | 0.9960 | Not Tested | 0.0494 | 2.46 | Not Tested | 1.92 ± 0.19 |
| 44 | Am | 5 | 4' | 3 | 0.4505 | 16.9 | 0.0414 | 7.32 | 18.7 | 0.78 ± 0.21 |
| 45 | iPrAm | 5 | 4' | 3 | 0.0409 | 70.4 | 0.0418 | 45.6 | Not Tested | 1.56 ± 0.58 |
| 46 | Im | 5 | 4' | 3 | 0.0606 | 7.60 | 0.0432 | 10.3 | Not Tested | Not Tested |
| 47 | Am | 5 | 4' | 4 | 0.1635 | 2.49 | 0.1412 | 1.30 | 11.8 | 0.61 ± 0.53 |
| 48 | iPrAm | 5 | 4' | 4 | 1.108 | 21.0 | 0.3018 | 6.92 | 13.3 | 2.97 ± 0.16 |

TABLE VI(a)-continued

Anti-protozoan Data for 'Unsymmetrical' Benzofuran Diamidines.

| N | R | Ring C Position | Ring A Position | n | T.b.r. IC$_{50}$ (µM) | T. cruzi IC$_{50}$ (µM) | P. falcip. IC$_{50}$ (µM) | Cytotox. IC$_{50}$ (µM) | DNA binding Δ T$_m$ | Leishmania Donovani IC$_{50}$ (µM) |
|---|---|---|---|---|---|---|---|---|---|---|
| 49 | Im | 5 | 4' | 4 | 0.3742 | 4.51 | 0.0641 | 2.88 | 18.8 | 9.21 ± 2.25 |
| 50 | Am | 5 | 4' | 5 | 0.3687 | 4.71 | 0.3131 | 4.19 | 12.7 | Not Tested |
| 51 | iPrAm | 5 | 4' | 5 | 0.3017 | 7.68 | 0.1927 | 20.5 | 18.7 | 2.08 ± 0.64 |
| 52 | Im | 5 | 4' | 5 | 0.3376 | 2.27 | 0.0600 | 0.87 | Not Tested | 39.4 ± 7.35 |
| 53 | Am | 5 | 4' | 6 | 0.3683 | 6.21 | 0.2633 | 3.29 | Not Tested | 0.65 ± 0.17 |
| 54 | iPrAm | 5 | 4' | 6 | 0.2107 | 1.21 | 0.0634 | 0.85 | Not Tested | 5.40 ± 1.46 |
| 55 | Im | 5 | 4' | 6 | 0.3599 | 1.83 | 0.1160 | 1.48 | 14.4 | 3.32 ± 0.97 |
| 56 | Am | 6 | 3' | 3 | 0.3270 | 11.1 | 0.0840 | 19.8 | Not Tested | 11.2 ± 0.28 |
| 57 | iPrAm | 6 | 3' | 3 | 0.4830 | 69.8 | 0.2016 | 82.3 | Not Tested | 10.6 ± 6.42 |
| 58 | Im | 6 | 3' | 3 | 1.0845 | 7.32 | 0.0952 | 10.1 | Not Tested | 4.73 ± 1.71 |
| 59 | Am | 6 | 3' | 4 | 1.334 | Not Tested | 0.3209 | 7.57 | Not Tested | 5.93 ± 0.24 |
| 60 | iPrAm | 6 | 3' | 4 | 0.9358 | Not Tested | 0.1782 | 46.5 | Not Tested | 12.3 ± 0.09 |
| 61 | Im | 6 | 3' | 4 | 2.8612 | 8.92 | 0.0976 | 5.84 | Not Tested | 7.38 ± 2.55 |
| 62 | Am | 6 | 3' | 5 | 0.5307 | 8.56 | 0.2824 | 4.12 | Not Tested | 5.75 ± 0.06 |
| 63 | iPrAm | 6 | 3' | 5 | 0.9107 | 29.7 | 0.2936 | 20.1 | Not Tested | 8.92 ± 0.71 |
| 64 | Im | 6 | 3' | 5 | 0.4416 | 3.62 | 0.0469 | 3.70 | Not Tested | 16.5 ± 3.45 |
| 65 | Am | 6 | 3' | 6 | 1.222 | Not Tested | 0.4788 | 4.33 | Not Tested | 23.6 ± 1.09 |
| 66 | iPrAm | 6 | 3' | 6 | 0.4205 | Not Tested | 0.3474 | 10.1 | Not Tested | 6.18 ± 0.06 |
| 67 | Im | 6 | 3' | 6 | 0.6813 | 3.67 | 0.0412 | 1.79 | Not Tested | 43.5 ± 0.69 |
| 68 | Am | 6 | 4' | 3 | | | | | Not Tested | |
| 69 | iPrAm | 6 | 4' | 3 | 0.0881 | 28.4 | 0.0366 | 49.9 | Not Tested | 3.18 ± 0.19 |
| 70 | Im | 6 | 4' | 3 | 0.1442 | 7.11 | 0.0418 | 16.8 | Not Tested | 0.48 ± 0.16 |
| 71 | Am | 6 | 4' | 4 | 1.056 | 12.5 | 0.1663 | 14.1 | Not Tested | 3.22 ± 0.96 |
| 72 | iPrAm | 6 | 4' | 4 | 1.745 | 12.5 | 0.1392 | 15.9 | Not Tested | 4.52 ± 1.81 |
| 73 | Im | 6 | 4' | 4 | 0.9419 | 9.82 | 0.0461 | 16.9 | Not Tested | 13.2 ± 0.86 |
| 74 | Am | 6 | 4' | 5 | 0.3135 | Not Tested | 0.2682 | 8.98 | Not Tested | 2.90 ± 0.14 |
| 75 | iPrAm | 6 | 4' | 5 | 0.5568 | 8.92 | 0.0744 | 10.7 | Not Tested | 1.38 ± 0.18 |
| 76 | Im | 6 | 4' | 5 | 0.2617 | 2.12 | 0.0280 | 3.20 | Not Tested | 10.4 ± 0.78 |
| 77 | Am | 6 | 4' | 6 | 0.4160 | Not Tested | 0.2801 | 8.02 | Not Tested | Not Tested |
| 78 | iPrAm | 6 | 4' | 6 | 0.8838 | 3.48 | 0.0519 | 4.90 | Not Tested | 2.62 ± 0.35 |
| 79 | Im | 6 | 4' | 6 | 0.2238 | 2.15 | 0.0316 | 3.44 | Not Tested | 15.3 ± 1.72 |
| 182 | AmOH | 5 | 4' | 3 | 1.337 | 1.70 | 1.403 | 2.64 | 1.10 | 5.02 ± 0.93 |
| 183 | AmOH | 5 | 4' | 5 | 1.555 | Not Tested | 0.2914 | 8.28 | Not Tested | Not Tested |

TABLE VI(b)

Anti-fungal Data for 'Unsymmetrical' Benzofuran Diamidines.

| N | R | Ring C Position | Ring A Position | n | Candida albicans (A39) | | | Aspergillus. Fumigatus (DUMC 168.95) | | | Cryptococcus neoformans (H99) | | |
|---|---|---|---|---|---|---|---|---|---|---|---|---|---|
| | | | | | MIC$_{80}$ (µg/ml) | MIC$_{100}$ (µg/ml) | MFC (µg/ml) | MIC$_{80}$ (µg/ml) | MIC$_{100}$ (µg/ml) | MFC (µg/ml) | MIC$_{80}$ (µg/ml) | MIC$_{100}$ (µg/ml) | MFC (µg/ml) |
| 32 | Am | 5 | 3' | 3 | ≦1 | 10 | 10 | 10 | 100 | >100 | Not Tested | — | — |
| 33 | iPrAm | 5 | 3' | 3 | ≦1 | 10 | 10 | 10 | 100 | >100 | Not Tested | — | — |
| 34 | Im | 5 | 3' | 3 | Not Tested | — | — | — | — | — | Not Tested | — | — |
| 35 | Am | 5 | 3' | 4 | Not Tested | — | — | — | — | — | Not Tested | — | — |
| 36 | iPrAm | 5 | 3' | 4 | Not Tested | — | — | — | — | — | Not Tested | — | — |
| 37 | Im | 5 | 3' | 4 | Not Tested | — | — | — | — | — | Not Tested | — | — |
| 38 | Am | 5 | 3' | 5 | 0.780 | 6.25 | 12.5 | 50 | >100 | — | 0.390 | 0.781 | 3.125 |
| 39 | iPrAm | 5 | 3' | 5 | 10 | 100 | 100 | 10 | 100 | >100 | Not Tested | — | — |
| 40 | Im | 5 | 3' | 5 | Not Tested | — | — | — | — | — | Not Tested | — | — |
| 41 | Am | 5 | 3' | 6 | Not Tested | — | — | — | — | — | Not Tested | — | — |
| 42 | iPrAm | 5 | 3' | 6 | Not Tested | — | — | — | — | — | Not Tested | — | — |
| 43 | Im | 5 | 3' | 6 | Not Tested | — | — | — | — | — | Not Tested | — | — |

TABLE VI(b)-continued

Anti-fungal Data for 'Unsymmetrical' Benzofuran Diamidines.

| N | R | Ring C Position | Ring A Position | n | Candida albicans (A39) | | | Aspergillus. Fumigatus (DUMC 168.95) | | | Cryptococcus neoformans (H99) | | |
|---|---|---|---|---|---|---|---|---|---|---|---|---|---|
| | | | | | $MIC_{80}$ (µg/ml) | $MIC_{100}$ (µg/ml) | MFC (µg/ml) | $MIC_{80}$ (µg/ml) | $MIC_{100}$ (µg/ml) | MFC (µg/ml) | $MIC_{80}$ (µg/ml) | $MIC_{100}$ (µg/ml) | MFC (µg/ml) |
| 44 | Am | 5 | 4' | 3 | ≦1 | ≦1 | 10 | 10 | >100 | — | Not Tested | — | — |
| 45 | iPrAm | 5 | 4' | 3 | 10 | 10 | 10 | 100 | >100 | — | Not Tested | — | — |
| 46 | Im | 5 | 4' | 3 | 10 | 10 | 10 | 10 | >100 | — | Not Tested | — | — |
| 47 | Am | 5 | 4' | 4 | ≦1 | 10 | 10 | 10 | 100 | >100 | Not Tested | — | — |
| 48 | iPrAm | 5 | 4' | 4 | 100 | 100 | 100 | 10 | 100 | >100 | Not Tested | — | — |
| 49 | Im | 5 | 4' | 4 | 100 | >100 | — | 100 | >100 | — | Not Tested | — | — |
| 50 | Am | 5 | 4' | 5 | 0.390 | 0.780 | 3.125 | 6.25 | >100 | — | 0.390 | 0.780 | 12.5 |
| 51 | iPrAm | 5 | 4' | 5 | 100 | 100 | 100 | 100 | 100 | >100 | Not Tested | — | — |
| 52 | Im | 5 | 4' | 5 | 10 | 10 | 10 | 10 | >100 | — | Not Tested | — | — |
| 53 | Am | 5 | 4' | 6 | 1.56 | 3.125 | 3.125 | 12.5 | >100 | — | 1.560 | 3.125 | 6.250 |
| 54 | iPrAm | 5 | 4' | 6 | >100 | >100 | — | >100 | >100 | — | Not Tested | — | — |
| 55 | Im | 5 | 4' | 6 | 10 | 10 | 10 | 10 | >100 | — | Not Tested | — | — |
| 56 | Am | 6 | 3' | 3 | Not Tested | — | — | — | — | — | Not Tested | — | — |
| 57 | iPrAm | 6 | 3' | 3 | Not Tested | — | — | — | — | — | Not Tested | — | — |
| 58 | Im | 6 | 3' | 3 | Not Tested | — | — | — | — | — | Not Tested | — | — |
| 59 | Am | 6 | 3' | 4 | Not Tested | — | — | — | — | — | Not Tested | — | — |
| 60 | iPrAm | 6 | 3' | 4 | Not Tested | — | — | — | — | — | Not Tested | — | — |
| 61 | Im | 6 | 3' | 4 | Not Tested | — | — | — | — | — | Not Tested | — | — |
| 62 | Am | 6 | 3' | 5 | 0.39 | 0.39 | 1.56 | 1.56 | 3.12 | >100 | 0.39 | 0.39 | 0.78 |
| 63 | iPrAm | 6 | 3' | 5 | Not Tested | — | — | — | — | — | Not Tested | — | — |
| 64 | Im | 6 | 3' | 5 | Not Tested | — | — | — | — | — | Not Tested | — | — |
| 65 | Am | 6 | 3' | 6 | Not Tested | — | — | — | — | — | Not Tested | — | — |
| 66 | iPrAm | 6 | 3' | 6 | Not Tested | — | — | — | — | — | Not Tested | — | — |
| 67 | Im | 6 | 3' | 6 | 1.56 | 1.56 | 1.56 | 12.5 | 12.5 | >100 | 0.781 | 1.56 | 1.56 |
| 68 | Am | 6 | 4' | 3 | Not Tested | — | — | — | — | — | Not Tested | — | — |
| 69 | iPrAm | 6 | 4' | 3 | Not Tested | — | — | — | — | — | Not Tested | — | — |
| 70 | Im | 6 | 4' | 3 | Not Tested | — | — | — | — | — | Not Tested | — | — |
| 71 | Am | 6 | 4' | 4 | Not Tested | — | — | — | — | — | Not Tested | — | — |
| 72 | iPrAm | 6 | 4' | 4 | Not Tested | — | — | — | — | — | Not Tested | — | — |
| 73 | Im | 6 | 4' | 4 | Not Tested | — | — | — | — | — | Not Tested | — | — |
| 74 | Am | 6 | 4' | 5 | Not Tested | — | — | — | — | — | Not Tested | — | — |
| 75 | iPrAm | 6 | 4' | 5 | Not Tested | — | — | — | — | — | Not Tested | — | — |
| 76 | Im | 6 | 4' | 5 | Not Tested | — | — | — | — | — | Not Tested | — | — |
| 77 | Am | 6 | 4' | 6 | Not Tested | — | — | — | — | — | Not Tested | — | — |
| 78 | iPrAm | 6 | 4' | 6 | Not Tested | — | — | — | — | — | Not Tested | — | — |
| 79 | Im | 6 | 4' | 6 | Not Tested | — | — | — | — | — | Not Tested | — | — |

TABLE VI(c)

Anti-protozoan Data for Cationic Substituted Benzofurans.

| N | R | Ring C and C' Position | n | T.b.r. $IC_{50}$ (µM) | T. cruzi $IC_{50}$ (µM) | P. falcip. $IC_{50}$ (µM) | Cytotox. $IC_{50}$ (µM) | DNA binding $\Delta T_m$ | Leishmania Donovani $IC_{50}$ (µM) |
|---|---|---|---|---|---|---|---|---|---|
| 1 | Am | 4, 4' | 1 | 0.2012 | 94.7 | 0.0677 | 22.5 | 1.1 | 14.0 ± 5.76 |
| 2 | iPrAm | 4, 4' | 1 | 13.97 | Not Tested | 0.9180 | 158 | Not Tested | >100 |
| 3 | Im | 4, 4' | 1 | 18.74 | 138 | 2.119 | 74.6 | 3.3 | >100 |
| 4 | Am | 5, 5' | 1 | 0.0719 | 48.1 | 0.0275 | 94.2 | 13.0 | 3.80 ± 1.10 |
| 5 | iPrAm | 5, 5' | 1 | 0.4550 | >194 | 0.1024 | >174 | 8.20 | 11.3 ± 1.45 |
| 6 | Im | 5, 5' | 1 | 0.4736 | 50.1 | 0.0342 | 165 | 17.1 | Not Tested |
| 7 | Im | 6, 6' | 1 | 4.631 | 84.9 | 0.0215 | 124 | 3.7 | 11.1 ± 6.96 |
| 8 | Am | 5, 5' | 2 | 0.0079 | 12.3 | 0.0025 | 21.5 | 6.1 | 1.06 ± 0.18 |
| 9 | iPrAm | 5, 5' | 2 | 0.1479 | >179 | 0.0032 | >179 | 4.00 | 4.15 ± 1.44 |

TABLE VI(c)-continued

Anti-protozoan Data for Cationic Substituted Benzofurans.

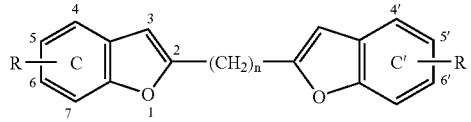

| N | R | Ring C and C' Position | n | T.b.r. IC$_{50}$ (μM) | T. cruzi IC$_{50}$ (μM) | P. falcip. IC$_{50}$ (μM) | Cytotox. IC$_{50}$ (μM) | DNA binding Δ T$_m$ | Leishmania Donovani IC$_{50}$ (μM) |
|---|---|---|---|---|---|---|---|---|---|
| 10 | Im | 5, 5' | 2 | 0.1268 | 2.27 | 0.0106 | 38.9 | 7.10 | 5.31 ± 1.43 |
| 11 | Am | 6, 6' | 2 | 0.0309 | 3.27 | 0.0043 | 78.9 | 9.10 | 0.88 ± 0.25 |
| 12 | iPrAm | 6, 6' | 2 | 0.0603 | >171 | 0.0046 | >171 | 7.00 | 2.46 ± 0.82 |
| 13 | Im | 6, 6' | 2 | 0.4148 | 8.24 | 0.0339 | 114 | 12.5 | 3.88 ± 1.67 |
| 14 | Am | 5, 5' | 3 | 0.1447 | 5.88 | 0.0414 | 104 | 10.1 | 4.41 ± 0.31 |
| 15 | iPrAm | 5, 5' | 3 | 0.1332 | >168 | 0.0084 | >168 | 7.60 | 31.1 ± 5.42 |
| 16 | Im | 5, 5' | 3 | 0.1326 | 8.18 | 0.0154 | >178 | 15.4 | 13.2 ± 3.81 |
| 17 | Am | 6, 6' | 3 | 0.0191 | 9.9 | 0.0367 | 38.5 | 1.70 | 2.38 ± 0.84 |
| 18 | iPrAm | 6, 6' | 3 | 0.1218 | >168 | 0.0355 | 155 | 1.70 | 5.68 ± 3.75 |
| 19 | Im | 6, 6' | 3 | 0.3548 | 20.0 | 0.3530 | 81.5 | 4.00 | 4.65 ± 3.46 |
| 20 | Am | 5, 5' | 4 | 0.0508 | 1.30 | 0.0318 | 34.6 | 7.40 | 1.34 ± 0.30 |
| 21 | iPrAm | 5, 5' | 4 | 0.0988 | 69.1 | 0.0098 | >163 | 6.60 | 12.7 ± 2.27 |
| 22 | Im | 5, 5' | 4 | 0.0732 | 0.925 | 0.0255 | 35.5 | 11.1 | 1.97 ± 0.28 |
| 23 | Am | 6, 6' | 4 | 0.0114 | 3.61 | 0.0578 | 12.0 | 8.60 | 1.52 ± 0.22 |
| 24 | iPrAm | 6, 6' | 4 | 0.0821 | 60.5 | 0.0760 | 27.9 | 7.60 | 3.87 ± 1.40 |
| 25 | Im | 6, 6' | 4 | 0.3213 | 19.6 | 0.1638 | 30.9 | 10.2 | Not Tested |
| 26 | Am | 5, 5' | 5 | 0.1272 | 1.93 | 0.0668 | 33.1 | 13.6 | 2.45 ± 0.49 |
| 27 | iPrAm | 5, 5' | 5 | 0.1007 | 81.0 | 0.0199 | >161 | 10.9 | 6.85 ± 2.04 |
| 28 | Im | 5, 5' | 5 | 0.1203 | 4.26 | 0.0672 | 35.1 | 13.2 | 1.83 ± 0.54 |
| 29 | Am | 5, 5' | 5 | 0.0778 | 8.40 | 0.0573 | 19.2 | Not Tested | Not Tested |
| 30 | iPrAm | 6, 6' | 5 | 0.4078 | 77.5 | 0.0178 | 70.0 | Not Tested | Not Tested |
| 31 | Im | 6, 6' | 5 | 0.5309 | 11.3 | 0.1331 | 13.3 | Not Tested | Not Tested |
| 184 | AmOH | 6, 6' | 5 | 2.197 | 4.9 | 17.22 | 19.4 | Not Tested | 22.2 ± 0.64 |
| 185 | AmOH | 5, 5' | 3 | 4.793 | 9.4 | >2.0 | 23.8 | Not Tested | >50 |
| 186 | AmOH | 5, 5' | 4 | 4.873 | 152 | >2.0 | >184 | Not Tested | >100 |
| 187 | AmOMe | 6, 6' | 5 | 13.81 | 38.4 | 9.762 | 34.6 | Not Tested | >50 |
| 188 | AmOMe | 5, 5' | 3 | 8.372 | >157 | >1.7 | >157 | Not Tested | >100 |
| 189 | AmOMe | 5, 5' | 4 | 6.868 | 61.9 | 2 | 74.3 | Not Tested | >100 |
| 190 | AmOH | 5, 5' | 2 | 10.12 | Not Tested | 0.4004 | >199 | Not Tested | Not Tested |
| 192 | AmOH | 5, 5' | 5 | 5.005 | 11.9 | >1.9 | 27.0 | Not Tested | 14.3 ± 6.49 |
| 193 | AmOMe | 5, 5' | 5 | >18.6 | 19.1 | >1.86 | 35.6 | Not Tested | >100 |

TABLE VI(d)

Anti-fungal Data for Cationic Substituted Benzofurans.

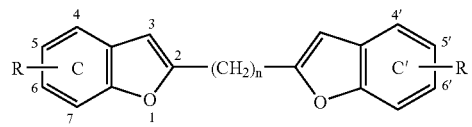

| N | R | Ring C Ring C' Position | n | Candida albicans (A39) | | | Aspergillus. Fumigatus (DUMC 168.95) | | | Cryptococcus neoformans (H99) | | |
|---|---|---|---|---|---|---|---|---|---|---|---|---|
| | | | | MIC$_{80}$ (μg/ml) | MIC$_{100}$ (μg/ml) | MFC (μg/ml) | MIC$_{80}$ (μg/ml) | MIC$_{100}$ (μg/ml) | MFC (μg/ml) | MIC$_{80}$ (μg/ml) | MIC$_{100}$ (μg/ml) | MFC (μg/ml) |
| 1 | Am | 4, 4' | 1 | 100 | 100 | 100 | 1.56 | 3.125 | >100 | 6.250 | 12.5 | 12.5 |
| 2 | iPrAm | 4, 4' | 1 | Not Tested | — | — | — | — | — | Not Tested | — | — |
| 3 | Im | 4, 4' | 1 | 100 | >100 | — | 100 | >100 | >100 | Not Tested | — | — |
| 4 | Am | 5, 5' | 1 | 100 | 100 | 100 | >100 | >100 | — | 100 | 100 | 100 |
| 5 | iPrAm | 5, 5' | 1 | >100 | >100 | — | >100 | >100 | — | >100 | >100 | — |
| 6 | Im | 5, 5' | 1 | 10 | 100 | 100 | >100 | >100 | — | 10 | 10 | >100 |
| 7 | Im | 6, 6' | 1 | 100 | 100 | 100 | 100 | >100 | — | Not Tested | — | — |
| 8 | Am | 5, 5' | 2 | 100 | 100 | 100 | >100 | >100 | — | 100 | 100 | 100 |
| 9 | iPrAm | 5, 5' | 2 | 100 | 100 | 100 | >100 | >100 | — | 100 | 100 | 100 |
| 10 | Im | 5, 5' | 2 | ≤1 | ≤1 | ≤1 | >100 | >100 | — | 10 | 10 | 10 |
| 11 | Am | 6, 6' | 2 | 10 | 10 | 100 | >100 | >100 | — | Not Tested | — | — |
| 12 | iPrAm | 6, 6' | 2 | 10 | 10 | 10 | >100 | >100 | — | Not Tested | — | — |
| 13 | Im | 6, 6' | 2 | >100 | >100 | — | >100 | >100 | — | Not Tested | — | — |

TABLE VI(d)-continued

Anti-fungal Data for Cationic Substituted Benzofurans.

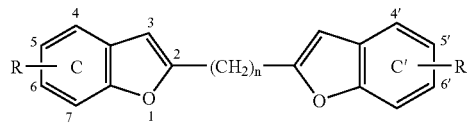

| | | Ring C Ring C' | | Candida albicans (A39) | | | Aspergillus. Fumigatus (DUMC 168.95) | | | Cryptococcus neoformans (H99) | | |
|---|---|---|---|---|---|---|---|---|---|---|---|---|
| N | R | Position | n | MIC$_{80}$ (μg/ml) | MIC$_{100}$ (μg/ml) | MFC (μg/ml) | MIC$_{80}$ (μg/ml) | MIC$_{100}$ (μg/ml) | MFC (μg/ml) | MIC$_{80}$ (μg/ml) | MIC$_{100}$ (μg/ml) | MFC (μg/ml) |
| 14 | Am | 5, 5' | 3 | 10 | 100 | 100 | >100 | >100 | — | 10 | 10 | 10 |
| 15 | iPrAm | 5, 5' | 3 | 100 | 100 | 100 | >100 | >100 | — | 100 | 100 | 100 |
| 16 | Im | 5, 5' | 3 | 10 | 10 | 10 | >100 | >100 | — | 100 | >100 | — |
| 17 | Am | 6, 6' | 3 | 100 | 100 | 100 | >100 | >100 | — | Not Tested | — | — |
| 18 | iPrAm | 6, 6' | 3 | 100 | 100 | 100 | >100 | >100 | — | Not Tested | — | — |
| 19 | Im | 6, 6' | 3 | 100 | 100 | — | >100 | >100 | — | Not Tested | — | — |
| 20 | Am | 5, 5' | 4 | ≦1 | 10 | 10 | 100 | 100 | >100 | 10 | 10 | 10 |
| 21 | iPrAm | 5, 5' | 4 | 10 | 10 | >100 | >100 | >100 | — | 100 | 100 | >100 |
| 22 | Im | 5, 5' | 4 | >100 | >100 | na | >100 | >100 | — | 100 | >100 | — |
| 23 | Am | 6, 6' | 4 | 0.39 | 0.780 | 6.25 | 100 | 100 | >100 | 0.780 | 0.780 | 1.560 |
| 24 | iPrAm | 6, 6' | 4 | 10 | 100 | 100 | >100 | >100 | — | Not Tested | — | — |
| 25 | Im | 6, 6' | 4 | 100 | 100 | 100 | 100 | 100 | >100 | Not Tested | — | — |
| 26 | Am | 5, 5' | 5 | 0.390 | 1.560 | 1.560 | >100 | >100 | — | 0.780 | 0.780 | 3.125 |
| 27 | iPrAm | 5, 5' | 5 | 10 | 10 | 10 | >100 | >100 | — | Not Tested | — | — |
| 28 | Im | 5, 5' | 5 | 100 | 100 | 100 | 100 | 100 | >100 | Not Tested | — | — |
| 29 | Am | 6, 6' | 5 | 0.390 | 1.560 | 1.560 | 100 | 100 | >100 | Not Tested | — | — |
| 30 | iPrAm | 6, 6' | 5 | 100 | 100 | 100 | 100 | 100 | — | Not Tested | — | — |
| 31 | Im | 6, 6' | 5 | 100 | >100 | — | 100 | 100 | >100 | Not Tested | — | — |

TABLE VII(a)

Asymmetric Benzofuran Compounds Tested Against *Mycobacterium tuberculosis*.

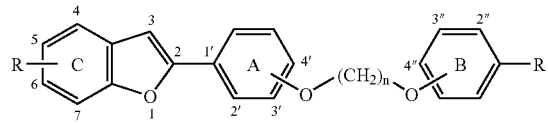

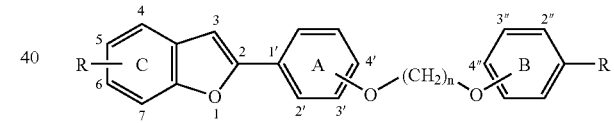

| Compound No. | n | R | Ring C Position | Ring A Position | M. tb. MIC$_{90}$ (μg/mL) | M. tb. MIC$_{90}$ (μM) |
|---|---|---|---|---|---|---|
| 44 | 3 | Am | 5 | 4' | 0.45 | 0.86 |
| 182 | 3 | AmOH | 5 | 4' | 0.65 | 1.20 |
| 46 | 3 | Im | 5 | 4' | | |
| 45 | 3 | iPrAm | 5 | 4' | 1.12 | 1.86 |
| 47 | 4 | Am | 5 | 4' | 31.77 | 59.80 |
| 49 | 4 | Im | 5 | 4' | | |
| 48 | 4 | iPrAm | 5 | 4' | 59.36 | 95.60 |
| 50 | 5 | Am | 5 | 4' | 1.01 | 1.84 |
| 183 | 5 | AmOH | 5 | 4' | | |
| 52 | 5 | Im | 5 | 4' | 10.14 | 16.86 |
| 53 | 6 | Am | 5 | 4' | 3.74 | 6.84 |
| 55 | 6 | Im | 5 | 4' | >82.69 | >128.00 |
| 54 | 6 | iPrAm | 5 | 4' | 65.80 | 102.50 |
| 32 | 3 | Am | 5 | 3' | 0.53 | 1.00 |
| 34 | 3 | Im | 5 | 3' | | |
| 33 | 3 | iPrAm | 5 | 3' | <0.62 | <1.00 |
| 35 | 4 | Am | 5 | 3' | | |
| 37 | 4 | Im | 5 | 3' | | |
| 36 | 4 | iPrAm | 5 | 3' | | |
| 38 | 5 | Am | 5 | 3' | 1.960 | 3.48 |
| 40 | 5 | Im | 5 | 3' | | |
| 39 | 5 | iPrAm | 5 | 3' | 1.12 | 1.80 |
| 41 | 6 | Am | 5 | 3' | | |
| 43 | 6 | Im | 5 | 3' | | |
| 42 | 6 | iPrAm | 5 | 3' | | |
| 51 | 5 | iPrAm | 5 | 4' | 0.90 | 1.43 |
| 56 | 3 | Am | 6 | 3' | 1.02 | 1.93 |
| 58 | 3 | Im | 6 | 3' | | |
| 57 | 3 | iPrAm | 6 | 3' | | |
| 59 | 4 | Am | 6 | 3' | | |
| 61 | 4 | Im | 6 | 3' | | |
| 60 | 4 | iPrAm | 6 | 3' | | |
| 62 | 5 | Am | 6 | 3' | 0.65 | 1.15 |
| 64 | 5 | Im | 6 | 3' | | |
| 63 | 5 | iPrAm | 6 | 3' | | |
| 65 | 6 | Am | 6 | 3' | | |
| 67 | 6 | Im | 6 | 3' | 18.01 | 29.35 |
| 66 | 6 | iPrAm | 6 | 3' | | |
| 70 | 3 | Im | 6 | 4' | 0.86 | 1.50 |
| 69 | 3 | iPrAm | 6 | 4' | 0.54 | 0.92 |
| 71 | 4 | Am | 6 | 4' | 0.45 | 0.85 |
| 73 | 4 | Im | 6 | 4' | | |
| 72 | 4 | iPrAm | 6 | 4' | | |
| 74 | 5 | Am | 6 | 4' | | |
| 76 | 5 | Im | 6 | 4' | | |
| 75 | 5 | iPrAm | 6 | 4' | 1.19 | 1.92 |
| 77 | 6 | Am | 6 | 4' | | |

TABLE VII(a)-continued

Asymmetric Benzofuran Compounds Tested Against *Mycobacterium tuberculosis*.

| Compound No. | n | R | Ring C Position | Ring A Position | M. tb. MIC$_{90}$ (μg/mL) | M. tb. MIC$_{90}$ (μM) |
|---|---|---|---|---|---|---|
| 79 | 6 | Im | 6 | 4' | 2.14 | 3.51 |
| 78 | 6 | iPrAm | 6 | 4' | 2.11 | 3.33 |

TABLE VII(b)

Asymmetric Benzofuran Compounds Tested Against *Mycobacterium tuberculosis*.

| Compound No. | R$_1$ | Ring C R$_1$ Substitution | Ring C R$_2$ Substitution | Ring A R$_1$ Substitution | M. tb MIC$_{90}$ (μg/mL) | M. tb MIC$_{90}$ (μM) |
|---|---|---|---|---|---|---|
| 163 | Am | 5 | H | 4' | | |
| 165 | in | 5 | H | 4' | 50.02 | 120.26 |
| 164 | iPrAm | 5 | H | 4' | | |
| 178 | AmOH | 5 | H | 4' | | >128.00 |
| 179 | AmOMe | 5 | H | 4' | | |
| 166 | Am | 5 | H | 3' | 11.93 | 31.61 |
| 167 | PrAm | 5 | H | 3' | >57.81 | >128.00 |
| 168 | Im | 5 | H | 3' | 10.81 | 25.66 |
| 175 | Am | 5 | OCH$_3$ | 4' | | |
| 177 | In | 5 | OCH$_3$ | 4' | | |
| 172 | Am | 6 | H | 4' | | |
| 173 | Im | 6 | H | 4' | | |
| 174 | iPrAm | 6 | H | 4' | | |
| 181 | AmOH | 6 | H | 4' | | |
| 169 | Am | 6 | H | 3' | | |
| 171 | Im | 6 | H | 3' | | |
| 170 | iPrAm | 6 | H | 3' | | |
| 180 | AmOH | 6 | H | 3' | | |

TABLE VIII

Bis-benzofuran Compounds Tested Against *Mycobacterium tuberculosis*.

| Compound No. | n | R | Ring C and C' Position | M. tb MIC$_{90}$ (μg/mL) | M. tb MIC$_{90}$ (μM) |
|---|---|---|---|---|---|
| 7 | 1 | Im | 6, 6' | >63.15 | >128.00 |
| 11 | 2 | Am | 6, 6' | 3.06 | 7.00 |
| 12 | 2 | iPrAm | 6, 6' | 59.33 | 113.00 |
| 13 | 2 | Im | 6, 6' | 7.29 | 15.00 |
| 17 | 3 | Am | 6, 6' | | |
| 18 | 3 | iPrAm | 6, 6' | | |
| 19 | 3 | Im | 6, 6' | | |
| 23 | 4 | Am | 6, 6' | | |
| 24 | 4 | iPrAm | 6, 6' | | |
| 25 | 4 | Im | 6, 6' | | |
| 29 | 5 | Am | 6, 6' | 0.790 | 1.67 |
| 30 | 5 | iPrAm | 6, 6' | 1.700 | 3.00 |

TABLE VIII-continued

Bis-benzofuran Compounds Tested Against *Mycobacterium tuberculosis*.

[Structure: R-C(benzofuran, positions 4,5,6,7)-2-(CH$_2$)$_n$-2-C'(benzofuran, positions 4',5',6',7')-R]

| Compound No. | n | R | Ring C and C' Position | M. tb MIC$_{90}$ (µg/mL) | M. tb MIC$_{90}$ (µM) |
|---|---|---|---|---|---|
| 31 | 5 | Im | 6, 6' | | |
| 184 | 5 | AmOH | 6, 6' | | |
| 187 | 5 | AmOMe | 6, 6' | | |
| 4 | 1 | Am | 5, 5' | 4.02 | 7.78 |
| 5 | 1 | iPrAm | 5, 5' | | |
| 6 | 1 | Im | 5, 5' | | |
| 8 | 2 | Am | 5, 5' | 5.15 | 11.63 |
| 9 | 2 | iPrAm | 5, 5' | 5.91 | 11.74 |
| 10 | 2 | Im | 5, 5' | 43.10 | 85.86 |
| 14 | 3 | Am | 5, 5' | 1.93 | 4.28 |
| 15 | 3 | iPrAm | 5, 5' | 1.00 | 1.87 |
| 16 | 3 | Im | 5, 5' | 16.22 | 31.99 |
| 185 | 3 | AmOH | 5, 5' | | |
| 188 | 3 | AmOMe | 5, 5' | | |
| 20 | 4 | Am | 5, 5' | 6.93 | 15.19 |
| 21 | 4 | iPrAm | 5, 5' | 0.07 | 0.13 |
| 22 | 4 | Im | 5, 5' | 2.36 | 4.33 |
| 186 | 4 | AmOH | 5, 5' | | |
| 189 | 4 | AmOMe | 5, 5' | | |
| 26 | 5 | Am | 5, 5' | 0.07 | 0.15 |
| 27 | 5 | iPrAm | 5, 5' | 0.08 | 0.15 |
| 28 | 5 | Im | 5, 5' | 3.08 | 5.61 |
| 192 | 5 | AmOH | 5, 5' | | |
| 193 | 5 | AmOMe | 5, 5' | 4.25 | 7.88 |
| 1 | 1 | Am | 4, 4' | >55.81 | >128.00 |
| 3 | 1 | Imidazoline | 4, 4' | >59.69 | >128.00 |
| 2 | 1 | iPrAm | 4, 4' | | |
| 190 | 2 | AmOH | 5, 5' | | |
| 191 | 2 | AmOMe | 5, 5' | | |

TABLE IX

Compiled Biological Activity Data for Asymmetric Benzofuran Compounds of Formula (II)

[Structure: R-C(benzofuran)-2-(Ring A with R$_1$ at 4' position)-R$_2$ at position 7]

| | R | Ring C, A Position | R$_1$ | T. b.r. IC$_{50}$ (µM) | T. cruzi IC$_{50}$ (µM) | P. falcip. IC$_{50}$ (µM) | Cytotox. IC$_{50}$ (µM) | DNA binding ΔT$_m$ | L. Donovani IC$_{50}$ (µM) |
|---|---|---|---|---|---|---|---|---|---|
| 166 | Am | 5, 3' | H | 0.0241 | 23.4 | 0.0191 | 21.2 | Not Tested | 5.82 ± 0.06 |
| 167 | iPrAm | 5, 3' | H | 0.4728 | >199 | 0.3306 | >199 | Not Tested | 13.4 ± 0.64 |
| 168 | Im | 5, 3' | H | 0.0776 | 39.6 | 0.0758 | 33.9 | Not Tested | 23.7 ± 0.17 |
| 163 | Am | 5, 4' | H | 0.0034 | 2.86 | 0.0466 | 1.91 | Not Tested | 0.99 ± 0.35 |
| 164 | iPrAm | 5, 4' | H | 0.1246 | >198 | 0.0730 | >198 | Not Tested | 1.58 ± 1.09 |
| 165 | Im | 5, 4' | H | 0.1893 | 4.56 | 0.0012 | 39.7 | Not Tested | 20.8 ± 11.0 |
| 169 | Am | 6, 3' | H | 0.0210 | Not Tested | 0.0035 | 131 | Not Tested | 14.4 |
| 170 | iPrAm | 6, 3' | H | 0.5336 | Not Tested | 0.0586 | >200 | Not Tested | 24.4 ± 0.10 |
| 171 | Im | 6, 3' | H | 0.3325 | Not Tested | 0.2050 | 12.8 | Not Tested | >100 |
| 172 | Am | 6, 4' | H | 0.0069 | Not Tested | 0.0031 | 0.83 | Not Tested | 3.13 ± 0.15 |
| 173 | iPrAm | 6, 4' | H | 0.1479 | Not Tested | 0.0145 | >199 | Not Tested | 11.8 ± 1.28 |
| 174 | Im | 6, 4' | H | 0.3190 | Not Tested | 0.1089 | 4.52 | Not Tested | >50 |
| 175 | Am | 5, 4' | OCH$_3$ | 0.0060 | Not Tested | 0.0056 | 30.7 | Not Tested | 3.00 ± 0.56 |
| 177 | Im | 5, 4' | OCH$_3$ | 0.1243 | Not Tested | 0.0323 | 19.9 | Not Tested | 4.45 ± 0.36 |
| 178 | AmOH | 5, 4' | H | 23.56 | >235 | 0.7828 | >235 | 4.50 | >100 |
| 179 | AmOCH$_3$ | 5, 4' | H | 75.37 | >219 | 2.502 | >219 | Not Tested | >100 |
| 180 | AmOH | 6, 3' | H | 37.81 | Not Tested | 1.848 | 13.8 | Not Tested | 68.5 ± 6.16 |
| 181 | AmOH | 6, 4' | H | 3.105 | Not Tested | 0.6094 | >222 | Not Tested | >100 |

The invention claimed is:
1. A compound of Formula (I):

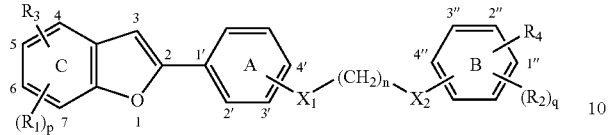

wherein:
n is an integer from 1 to 8;
p and q are integers from 0 to 3;
$X_1$ and $X_2$ are each;
$X_1$ is at one of the 3'-position and 4'-position of ring A;
$X_2$ is at the 4"-position of ring B;
$R_1$ and $R_2$ are each alkyl;
$R_3$ is one of the 5-position and 6-position of ring C;
$R_4$ is at the 1"-position of ring B; and
$R_3$ and $R_4$ are each:

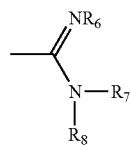

wherein:
$R_6$, $R_7$, and $R_8$ are each independently selected from the group consisting of H, alkyl, cycloalkyl, aryl, aralkyl, hydroxyl, alkoxyl, hydroxyalkyl, hydroxycycloalkyl, alkoxycycloalkyl, aminoalkyl, acyloxyl, alkylaminoalkyl, and alkoxycarbonyl; or
$R_6$ and $R_7$ together represent a $C_2$ to $C_{10}$ alkyl, $C_2$ to $C_{10}$ hydroxyalkyl, or $C_2$ to $C_{10}$ alkylene.

2. The compound of claim 1, wherein:
n is an integer from 3 to 6; and
$R_3$ and $R_4$ are each

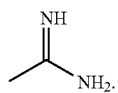

3. The compound of claim 1, wherein:
n is an integer from 3 to 6; and
$R_3$ and $R_4$ are each

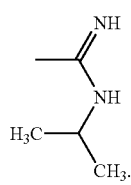

4. The compound of claim 1, wherein:
n is an integer from 3 to 6; and
$R_3$ and $R_4$ are each

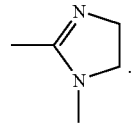

5. The compound of claim 1, wherein:
n is an integer from 3 to 6; and
$R_3$ and $R_4$ are each

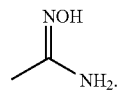

6. The compound of claim 1, wherein:
n is an integer from 3 to 6; and
$R_3$ and $R_4$ are each

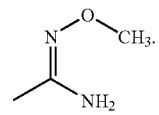

7. A compound selected from the group consisting of:
2-(3-(3-(4-Carbamimidoylphenoxy)propoxy)phenyl)benzofuran-5-carboxamidine;
2-(3-(3-(4-(N-Isopropylcarbamimidoyl)phenoxy)propoxy)phenyl)-N-isopropylbenzofuran-5-carboxamidine;
2-(2-(3-(3-(4-(4,5-Dihydro-1H-imidazol-2-yl)phenoxy)propoxy)phenyl)benzofuran-5-yl)-4,5-dihydro-1H-imidazole;
2-(3-(4-(4-Carbamimidoylphenoxy)butoxy)phenyl)benzofuran-5-carboxamidine;
2-(3-(4-(4-(N-Isopropylcarbamimidoyl)phenoxy)butoxy)phenyl)-N-isopropylbenzofuran-5-carboxamidine;
2-(2-(3-(4-(4-(4,5-Dihydro-1H-imidazol-2-yl)phenoxy)butoxy)phenyl)benzofuran-5-yl)-4,5-dihydro-1H-imidazole;
2-(3-(5-(4-Carbamimidoylphenoxy)pentyloxy)phenyl)benzofuran-5-carboxamidine;
2-(3-(5-(4-(N-Isopropylcarbamimidoyl)phenoxy)pentyloxy)phenyl)-N-isopropylbenzofuran-5-carboxamidine;
2-(2-(3-(5-(4-(4,5-Dihydro-1H-imidazol-2-yl)phenoxy)pentyloxy)phenyl)benzofuran-5-yl)-4,5-dihydro-1H-imidazole;
2-(3-(6-(4-Carbamimidoylphenoxy)hexyloxy)phenyl)benzofuran-5-carboxamidine;
2-(3-(6-(4-(N-Isopropylcarbamimidoyl)phenoxy)hexyloxy)phenyl)-N-isopropylbenzofuran-5-carboxamidine;
2-(2-(3-(6-(4-(4,5-Dihydro-1H-imidazol-2-yl)phenoxy)hexyloxy)phenyl)benxofuran-5-yl)-4,5-dihydro-1H-imidazole;
2-(4-(3-(4-Carbamimidoylphenoxy)propoxy)phenyl)benzofuran-5-carboxamidine;
2-(4-(3-(4-(N-Isopropylcarbamimidoyl)phenoxy)propoxy)phenyl)-N-isopropylbenzofuran-5-carboxamidine;

2-(2-(4-(3-(4-(4,5-Dihydro-1H-imidazol-2-yl)phenoxy)propoxy)phenyl)benzofuran-5-yl)-4,5-dihydro-1H-imidazole;
2-(4-(4-(4-Carbamimidoylphenoxy)butoxy)phenyl)benzofuran-5-carboxamidine;
2-(4-(4-(4-(N-Isopropylcarbamimidoyl)phenoxy)butoxy)phenyl)-N-isopropylbenzofuran-5-carboxamidine;
2-(2-(4-(4-(4-(4,5-Dihydro-1H-imidazol-2-yl)phenoxy)butoxy)phenyl)benzofuran-5-yl)-4,5-dihydro-1H-imidazole;
2-(4-(5-(4-Carbamimidoylphenoxy)pentyloxy)phenyl)benzofuran-5-carboxamidine;
2-(4-(5-(4-(N-Isopropylcarbamimidoyl)phenoxy)pentyloxy)phenyl)-N-isopropylbenzofuran-5-carboxamidine;
2-(2-(4-(5-(4-(4,5-Dihydro-1H-imidazol-2-yl)phenoxy)pentyloxy)phenyl)benzofuran-5-yl)-4,5-dihydro-1H-imidazole;
2-(4-(6-(4-Carbamimidoylphenoxy)hexyloxy)phenyl)benzofuran-5-carboxamidine;
2-(4-(6-(4-(N-Isopropylcarbamimidoyl)phenoxy)hexyloxy)phenyl)-N-isopropylbenzofuran-5-carboxamidine;
2-(2-(4-(6-(4-(4,5-Dihydro-1H-imidazol-2-yl)phenoxy)hexyloxy)phenyl)benzofuran-5-yl)-4,5-dihydro-1H-imidazole;
2-(3-(3-(4-Carbamimidoylphenoxy)propoxy)phenyl)benzofuran-6-carboxamidine;
2-(3-(3-(4-(N-Isopropylcarbamimidoyl)phenoxy)propoxy)phenyl)-N-isopropylbenzofuran-6-carboxamidine;
2-(2-(3-(3-(4-(4,5-Dihydro-1H-imidazol-2-yl)phenoxy)propoxy)phenyl)benzofuran-6-yl)-4,5-dihydro-1H-imidazole;
2-(3-(4-(4-Carbamimidoylphenoxy)butoxy)phenyl)benzofuran-6-carboxamidine;
2-(3-(4-(4-(N-Isopropylcarbamimidoyl)phenoxy)butoxy)phenyl)-N-isopropylbenzofuran-6-carboxamidine;
2-(2-(3-(4-(4-(4,5-Dihydro-1H-imidazol-2-yl)phenoxy)butoxy)phenyl)benzofuran-6-yl)-4,5-dihydro-1H-imidazole;
2-(3-(5-(4-Carbamimidoylphenoxy)pentyloxy)phenyl)benzofuran-6-carboxamidine;
2-(3-(5-(4-(N-Isopropylcarbamimidoyl)phenoxy)pentyloxy)phenyl)-N-isopropylbenzofuran-6-carboxamidine;
2-(2-(3-(5-(4-(4,5-Dihydro-1H-imidazol-2-yl)phenoxy)pentyloxy)phenyl)benzofuran-6-yl)-4,5-dihydro-1H-imidazole;
2-(3-(6-(4-Carbamimidoylphenoxy)hexyloxy)phenyl)benzofuran-6-carboxamidine;
2-(3-(6-(4-(N-Isopropylcarbamimidoyl)phenoxy)hexyloxy)phenyl)-N-isopropylbenzofuran-6-carboxamidine;
2-(2-(3-(6-(4-(4,5-Dihydro-1H-imidazol-2-yl)phenoxy)hexyloxy)phenyl)benzofuran-6-yl)-4,5-dihydro-1H-imidazole;
2-(4-(3-(4-Carbamimidoylphenoxy)propoxy)phenyl)benzofuran-6-carboxamidine;
2-(4-(3-(4-(N-Isopropylcarbamimidoyl)phenoxy)propoxy)phenyl)-N-isopropylbenzofuran-6-carboxamidine;
2-(2-(4-(3-(4-(4,5-Dihydro-1H-imidazol-2-yl)phenoxy)propoxy)phenyl)benzofuran-6-yl)-4,5-dihydro-1H-imidazole;
2-(4-(4-(4-Carbamimidoylphenoxy)butoxy)phenyl)benzofuran-6-carboxamidine;
2-(4-(4-(4-(N-Isopropylcarbamimidoyl)phenoxy)butoxy)phenyl)-N-isopropylbenzofuran-6-carboxamidine;
2-(2-(4-(4-(4-(4,5-Dihydro-1H-imidazol-2-yl)phenoxy)butoxy)phenyl)benzofuran-6-yl)-4,5-dihydro-1H-imidazole;
2-(4-(5-(4-Carbamimidoylphenoxy)pentyloxy)phenyl)benzofuran-6-carboxamidine;
2-(4-(5-(4-(N-Isopropylcarbamimidoyl)phenoxy)pentyloxy)phenyl)-N-isopropylbenzofuran-6-carboxamidine;
2-(2-(4-(5-(4-(4,5-Dihydro-1H-imidazol-2-yl)phenoxy)pentyloxy)phenyl)benzofuran-6-yl)-4,5-dihydro-1H-imidazole;
2-(4-(6-(4-Carbamimidoylphenoxy)hexyloxy)phenyl)benzofuran-6-carboxamidine;
2-(4-(6-(4-(N-Isopropylcarbamimidoyl)phenoxy)hexyloxy)phenyl)-N-isopropylbenzofuran-6-carboxamidine;
2-(2-(4-(6-(4-(4,5-Dihydro-1H-imidazol-2-yl)phenoxy)hexyloxy)phenyl)benzofuran-6-yl)-4,5-dihydro-1H-imidazole;
2-(4-(3-(4-(N-hydroxycarbamimidoyl)phenoxy)propoxy)phenyl)-N-hydroxybenzofuran-5-carboxamidine; and
2-(4-(5-(4-(N-hydroxycarbamimidoyl)phenoxy)pentyloxy)phenyl)-N-hydroxybenzofuran-5-carboxamidine.

8. A pharmaceutically acceptable salt of a compound of claim 1.

9. The pharmaceutically acceptable salt of claim 8, wherein the salt is a hydrochloride salt.

10. The compound of claim 1 wherein p and q are each 0.

11. A pharmaceutical formulation comprising:
(a) a compound of Formula (I):

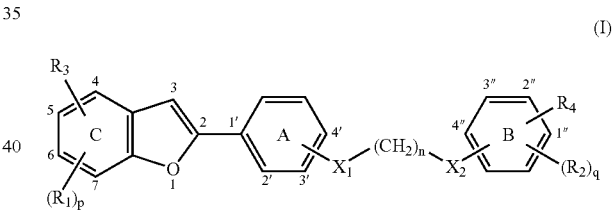

(I)

wherein:
n is an integer from 1 to 8;
p and q are integers from 0 to 3;
$X_1$ and $X_2$ are each O;
$X_1$ is at one of the 3'-position and 4'-position of ring A;
$X_2$ is at the 4"-position of ring B;
$R_1$ and $R_2$ are each alkyl;
$R_3$ is at one of the 5-position and 6-position of ring C;
$R_4$ is at the 1"-position of ring B; and
$R_3$ and $R_4$ are each:

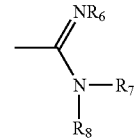

wherein:
$R_6$, $R_7$, and $R_8$ are each independently selected from the group consisting of H, alkyl, cycloalkyl, aryl, aralkyl, hydroxyl, alkoxyl, hydroxyalkyl, hydroxycycloalkyl, alkoxycycloalkyl, aminoalkyl, acyloxyl, alkylaminoalkyl, and alkoxycarbonyl; or $R_6$ and $R_7$ together represent a $C_2$ to $C_{10}$ alkyl, $C_2$ to $C_{10}$ hydroxyalkyl, or $C_2$ to $C_{10}$ alkylene; and (b) a pharmaceutically acceptable carrier.

12. A method of treating a microbial infection in a subject in need thereof, the method comprising administering to the subject an effective amount of a compound of Formula (I):

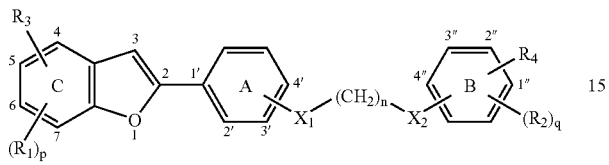
(I)

wherein:
n is an integer from 1 to 8;
p and q are each independently integers from 0 to 3;
$X_1$ and $X_2$ are each;
$X_1$ is at one of the 3'-position and 4'-position of ring A;
$X_2$ is at the 4"-position of ring B;
$R_1$ and $R_2$ are each alkyl;
$R_3$ is at one of the 5-position and 6-position of ring C;
$R_4$ is at the 1"-position of ring B; and
$R_3$ and $R_4$ are each:

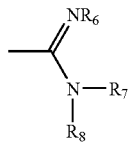

wherein:
$R_6$, $R_7$, and $R_8$ are each independently selected from the group consisting of H, alkyl, cycloalkyl, aryl, aralkyl, hydroxyl, alkoxyl, hydroxyalkyl, hydroxycycloalkyl, alkoxycycloalkyl, aminoalkyl, acyloxyl, alkylaminoalkyl, and alkoxycarbonyl; or
$R_6$ and $R_7$ together represent a $C_2$ to $C_{10}$ alkyl, $C_2$ to $C_{10}$ hydroxyalkyl, or $C_2$ to $C_{10}$ alkylene.

13. The method of claim 1, wherein the microbial infection is selected for the group consisting of a *Mycobacterium tuberculosis* infection, a *Leishmania donovani* infection, a *Trypanosoma brucei rhodesiense* infection, a *Trypanosoma cruzi* infection, a *Plasmodium falciparum* infection, a *Candida albicans* infection, an *Aspergillus fumigatus* infection, and a *Cryptococcus neoformans* infection.

14. The method of claim 1, wherein:
n is an integer from 3 to 6; and
$R_3$ and $R_4$ are each

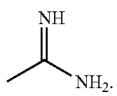

15. The method of claim 1, wherein:
n is an integer from 3 to 6; and
$R_3$ and $R_4$ are each

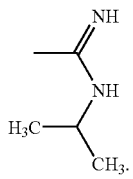

16. The method of claim 1, wherein:
n is an integer from 3 to 6; and
$R_3$ and $R_4$ are each

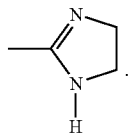

17. The method of claim 1, wherein:
n is an integer from 3 to 6; and
$R_3$ and $R_4$ are each

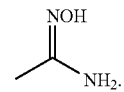

18. The method of claim 1, wherein:
n is an integer from 3 to 6; and
$R_3$ and $R_4$ are each

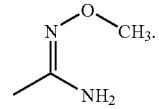

19. The method of claim 1, wherein the compound is selected from the group consisting of:
2-(3-(3-(4-Carbamimidoylphenoxy)propoxy)phenyl)benzofuran-5-carboxamidine;
2-(3-(3-(4-(N-Isopropylcarbamimidoyl)phenoxy)propoxy)phenyl)-N-isopropylbenzofuran-5-carboxamidine;
2-(2-(3-(3-(4-(4,5-Dihydro-1H-imidazol-2-yl)phenoxy)propoxy)phenyl)benzofuran-5-yl)-4,5-dihydro-1H-imidazole;
2-(3-(4-(4-Carbamimidoylphenoxy)butoxy)phenyl)benzofuran-5-carboxamidine;
2-(3-(4-(4-(N-Isopropylcarbamimidoyl)phenoxy)butoxy)phenyl)-N-isopropylbenzofuran-5-carboxamidine;
2-(2-(3-(4-(4-(4,5-Dihydro-1H-imidazol-2-yl)phenoxy)butoxy)phenyl)benzofuran-5-yl)-4,5-dihydro-1H-imidazole;
2-(3-(5-(4-Carbamimidoylphenoxy)pentyloxy)phenyl)benzofuran-5-carboxamidine;
2-(3-(5-(4-(N-Isopropylcarbamimidoyl)phenoxy)pentyloxy)phenyl)-N-isopropylbenzofuran-5-carboxamidine;
2-(2-(3-(5-(4-(4,5-Dihydro-1H-imidazol-2-yl)phenoxy)pentyloxy)phenyl)benzofuran-5-yl)-4,5-dihydro-1H-imidazole;

2-(3-(6-(4-Carbamimidoylphenoxy)hexyloxy)phenyl)benzofuran-5-carboxamidine;
2-(3-(6-(4-(N-Isopropylcarbamimidoyl)phenoxy)hexyloxy)phenyl)-N-isopropylbenzofuran-5-carboxamidine;
2-(2-(3-(6-(4-(4,5-Dihydro-1H-imidazol-2-yl)phenoxy)hexyloxy)phenyl)benzofuran-5-yl)-4,5-dihydro-1H-imidazole;
2-(4-(3-(4-Carbamimidoylphenoxy)propoxy)phenyl)benzofuran-5-carboxamidine;
2-(4-(3-(4-(N-Isopropylcarbamimidoyl)phenoxy)propoxy)phenyl)-N-isopropylbenzofuran-5-carboxamidine;
2-(2-(4-(3-(4-(4,5-Dihydro-1H-imidazol-2-yl)phenoxy)propoxy)phenyl)benzofuran-5-yl)-4,5-dihydro-1H-imidazole;
2-(4-(4-(4-Carbamimidoylphenoxy)butoxy)phenyl)benzofuran-5-carboxamidine;
2-(4-(4-(4-(N-Isopropylcarbamimidoyl)phenoxy)butoxy)phenyl)-N-isopropylbenzofuran-5-carboxamidine;
2-(2-(4-(4-(4-(4,5-Dihydro-1H-imidazol-2-yl)phenoxy)butoxy)phenyl)benzofuran-5-yl)-4,5-dihydro-1H-imidazole;
2-(4-(5-(4-Carbamimidoylphenoxy)pentyloxy)phenyl)benzofuran-5-carboxamidine;
2-(4-(5-(4-(N-Isopropylcarbamimidoyl)phenoxy)pentyloxy)phenyl)-N-isopropylbenzofuran-5-carboxamidine;
2-(2-(4-(5-(4-(4,5-Dihydro-1H-imidazol-2-yl)phenoxy)pentyloxy)phenyl)benzofuran-5-yl)-4,5-dihydro-1H-imidazole;
2-(4-(6-(4-Carbamimidoylphenoxy)hexyloxy)phenyl)benzofuran-5-carboxamidine;
2-(4-(6-(4-(N-Isopropylcarbamimidoyl)phenoxy)hexyloxy)phenyl)-N-isopropylbenzofuran-5-carboxamidine;
2-(2-(4-(6-(4-(4,5-Dihydro-1H-imidazol-2-yl)phenoxy)hexyloxy)phenyl)benzofuran-5-yl)-4,5-dihydro-1H-imidazole;
2-(3-(3-(4-Carbamimidoylphenoxy)propoxy)phenyl)benzofuran-6-carboxamidine;
2-(3-(3-(4-(N-Isopropylcarbamimidoyl)phenoxy)propoxy)phenyl)-N-isopropylbenzofuran-6-carboxamidine;
2-(2-(3-(3-(4-(4,5-Dihydro-1H-imidazol-2-yl)phenoxy)propoxy)phenyl)benzofuran-6-yl)-4,5-dihydro-1H-imidazole;
2-(3-(4-(4-Carbamimidoylphenoxy)butoxy)phenyl)benzofuran-6-carboxamidine;
2-(3-(4-(4-(N-Isopropylcarbamimidoyl)phenoxy)butoxy)phenyl)-N-isopropylbenzofuran-6-carboxamidine;
2-(2-(3-(4-(4-(4,5-Dihydro-1H-imidazol-2-yl)phenoxy)butoxy)phenyl)benzofuran-6-yl)-4,5-dihydro-1H-imidazole;
2-(3-(5-(4-Carbamimidoylphenoxy)pentyloxy)phenyl)benzofuran-6-carboxamidine;
2-(3-(5-(4-(N-Isopropylcarbamimidoyl)phenoxy)pentyloxy)phenyl)-N-isopropylbenzofuran-6-carboxamidine;
2-(2-(3-(5-(4-(4,5-Dihydro-1H-imidazol-2-yl)phenoxy)pentyloxy)phenyl)benzofuran-6-yl)-4,5-dihydro-1H-imidazole;
2-(3-(6-(4-Carbamimidoylphenoxy)hexyloxy)phenyl)benzofuran-6-carboxamidine;
2-(3-(6-(4-(N-Isopropylcarbamimidoyl)phenoxy)hexyloxy)phenyl)-N-isopropylbenzofuran-6-carboxamidine;
2-(2-(3-(6-(4-(4,5-Dihydro-1H-imidazol-2-yl)phenoxy)hexyloxy)phenyl)benzofuran-6-yl)-4,5-dihydro-1H-imidazole;
2-(4-(3-(4-Carbamimidoylphenoxy)propoxy)phenyl)benzofuran-6-carboxamidine;
2-(4-(3-(4-(N-Isopropylcarbamimidoyl)phenoxy)propoxy)phenyl)-N-isopropylbenzofuran-6-carboxamidine;
2-(2-(4-(3-(4-(4,5-Dihydro-1H-imidazol-2-yl)phenoxy)propoxy)phenyl)benzofuran-6-yl)-4,5-dihydro-1H-imidazole;
2-(4-(4-(4-Carbamimidoylphenoxy)butoxy)phenyl)benzofuran-6-carboxamidine;
2-(4-(4-(4-(N-Isopropylcarbamimidoyl)phenoxy)butoxy)phenyl)-N-isopropylbenzofuran-6-carboxamidine;
2-(2-(4-(4-(4-(4,5-Dihydro-1H-imidazol-2-yl)phenoxy)butoxy)phenyl)benzofuran-6-yl)-4,5-dihydro-1H-imidazole;
2-(4-(5-(4-Carbamimidoylphenoxy)pentyloxy)phenyl)benzofuran-6-carboxamidine;
2-(4-(5-(4-(N-Isopropylcarbamimidoyl)phenoxy)pentyloxy)phenyl)-N-isopropylbenzofuran-6-carboxamidine;
2-(2-(4-(5-(4-(4,5-Dihydro-1H-imidazol-2-yl)phenoxy)pentyloxy)phenyl)benzofuran-6-yl)-4,5-dihydro-1H-imidazole;
2-(4-(6-(4-Carbamimidoylphenoxy)hexyloxy)phenyl)benzofuran-6-carboxamidine;
2-(4-(6-(4-(N-Isopropylcarbamimidoyl)phenoxy)hexyloxy)phenyl)-N-isopropylbenzofuran-6-carboxamidine;
2-(2-(4-(6-(4-(4,5-Dihydro-1H-imidazol-2-yl)phenoxy)hexyloxy)phenyl)benzofuran-6-yl)-4,5-dihydro-1H-imidazole;
2-(4-(3-(4-(N-hydroxycarbamimidoyl)phenoxy)propoxy)phenyl)-N-hydroxybenzofuran-5-carboxamidine; and
2-(4-(5-(4-(N-hydroxycarbamimidoyl)phenoxy)pentyloxy)phenyl)-N-hydroxybenzofuran-5-carboxamidine.

20. The method of claim 1, wherein the compound of Formula I is administered in the form of a pharmaceutically acceptable salt.

21. The method of claim 19, wherein the pharmaceutically acceptable salt is a hydrochloride salt.

\* \* \* \* \*